(12) United States Patent
Sato et al.

(10) Patent No.: US 10,508,272 B2
(45) Date of Patent: Dec. 17, 2019

(54) RECOMBINANT YEAST HAVING ENHANCED XYLOSE FERMENTATION CAPABILITIES AND METHODS OF USE

(71) Applicant: Wisconsin Alumni Research Foundation, Madison, WI (US)

(72) Inventors: Trey Kyle Sato, Madison, WI (US); Jeff Scott Piotrowski, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 155 days.

(21) Appl. No.: 14/683,724

(22) Filed: Apr. 10, 2015

(65) Prior Publication Data

US 2015/0307872 A1    Oct. 29, 2015

Related U.S. Application Data

(60) Provisional application No. 61/978,585, filed on Apr. 11, 2014.

(51) Int. Cl.
| | |
|---|---|
| C12N 1/19 | (2006.01) |
| C12N 9/04 | (2006.01) |
| C07K 14/395 | (2006.01) |
| C12P 7/10 | (2006.01) |
| C12N 9/12 | (2006.01) |
| C12N 15/10 | (2006.01) |
| C12N 9/24 | (2006.01) |
| C12N 9/10 | (2006.01) |
| C12N 9/92 | (2006.01) |

(52) U.S. Cl.
CPC ........ *C12N 15/1024* (2013.01); *C07K 14/395* (2013.01); *C12N 9/0006* (2013.01); *C12N 9/1022* (2013.01); *C12N 9/1205* (2013.01); *C12N 9/2482* (2013.01); *C12N 9/92* (2013.01); *C12P 7/10* (2013.01)

(58) Field of Classification Search
None
See application file for complete search history.

(56) References Cited

U.S. PATENT DOCUMENTS 9,920,312 B2 *   3/2018   Froehlich ................. C12N 9/92

OTHER PUBLICATIONS

Kotter et al., Xylose fermentation by *Saccharomyces cerevisiae*, Appl. Microbiol. Biotechnol., 1993, 38, 776-83.*
Gerber et al., The Yeast Scaffold Proteins Isu1p and Isu2p Are Required inside Mitochondria for Maturation of Cytosolic Fe/S Proteins, Mol. Cell. Biol., 2004, 24, 4848-57.*
Zhou et al., Xylose isomerase overexpression along with engineering of the pentose phosphate pathway and evolutionary engineering enable rapid xylose utilization and ethanol production by *Saccharomyces cerevisiae*, Metabolic Eng., 2012, 14, 611-22.*
Sato et al., Directed Evolution Reveals Unexpected Epistatic Interactions That Alter Metabolic Regulation and Enable Anaerobic Xylose Use by *Saccharomyces cerevisiae*, PLoS Genet., 2016, 12, e1006372.*
Parreiras et al., Engineering and Two-Stage Evolution of a Lignocellulosic Hydrolysate-Tolerant *Saccharomyces cerevisiae* Strain for Anaerobic Fermentation of Xylose from AFEX Pretreated Corn Stover, PLoS One, Sep. 2014, 9, e107499.*

* cited by examiner

*Primary Examiner* — Robert B Mondesi
*Assistant Examiner* — Todd M Epstein
(74) *Attorney, Agent, or Firm* — Boyle Fredrickson S.C.

(57) ABSTRACT

The present invention relates to the production of biofuels and chemical feedstocks. The present invention provides recombinant yeast having enhanced xylose fermentation capabilities. Methods of using such recombinant yeast for improved biofuel and chemical feedstock production are also provided.

22 Claims, 16 Drawing Sheets
(15 of 16 Drawing Sheet(s) Filed in Color)
Specification includes a Sequence Listing.

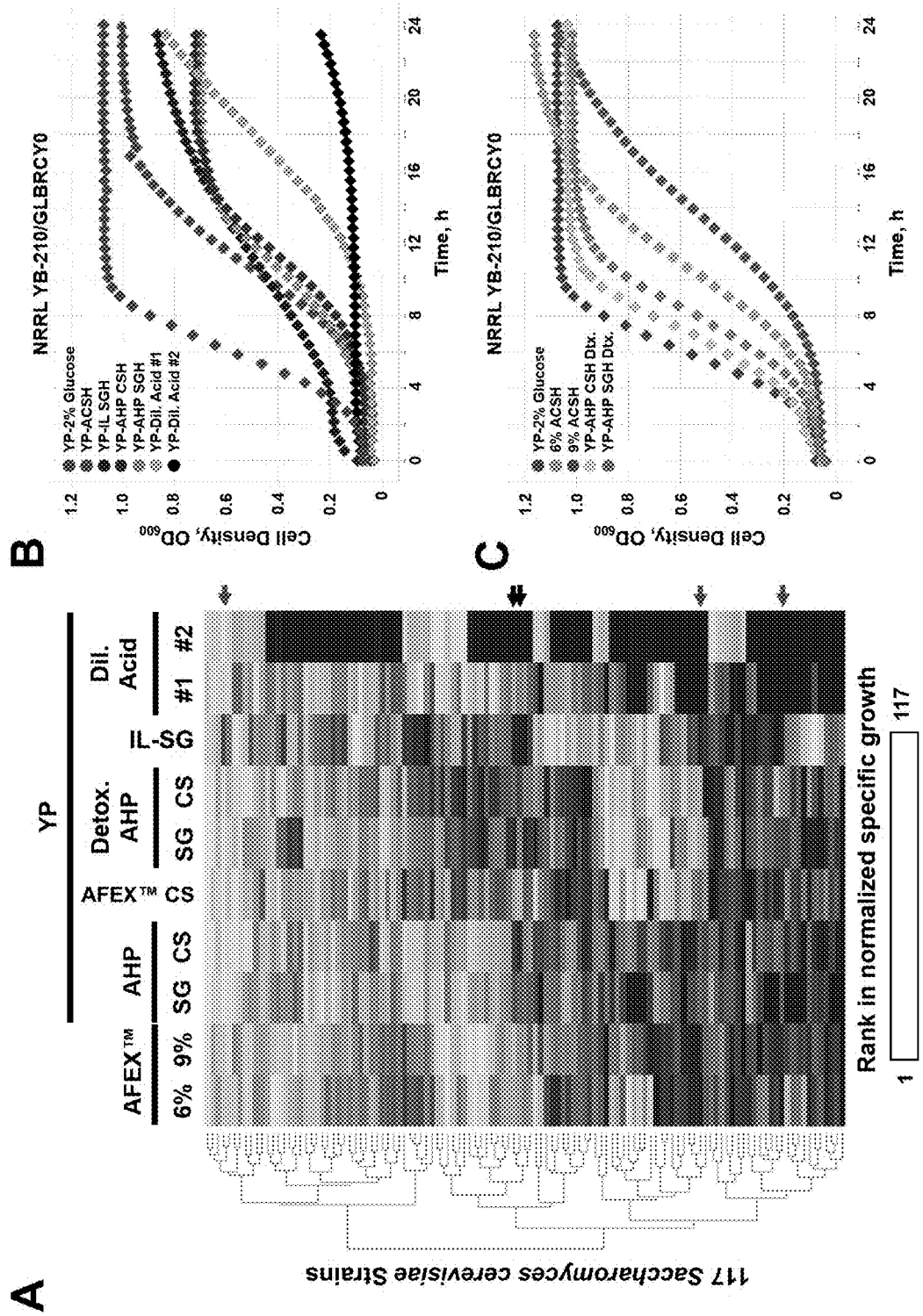
FIG. 2A-C

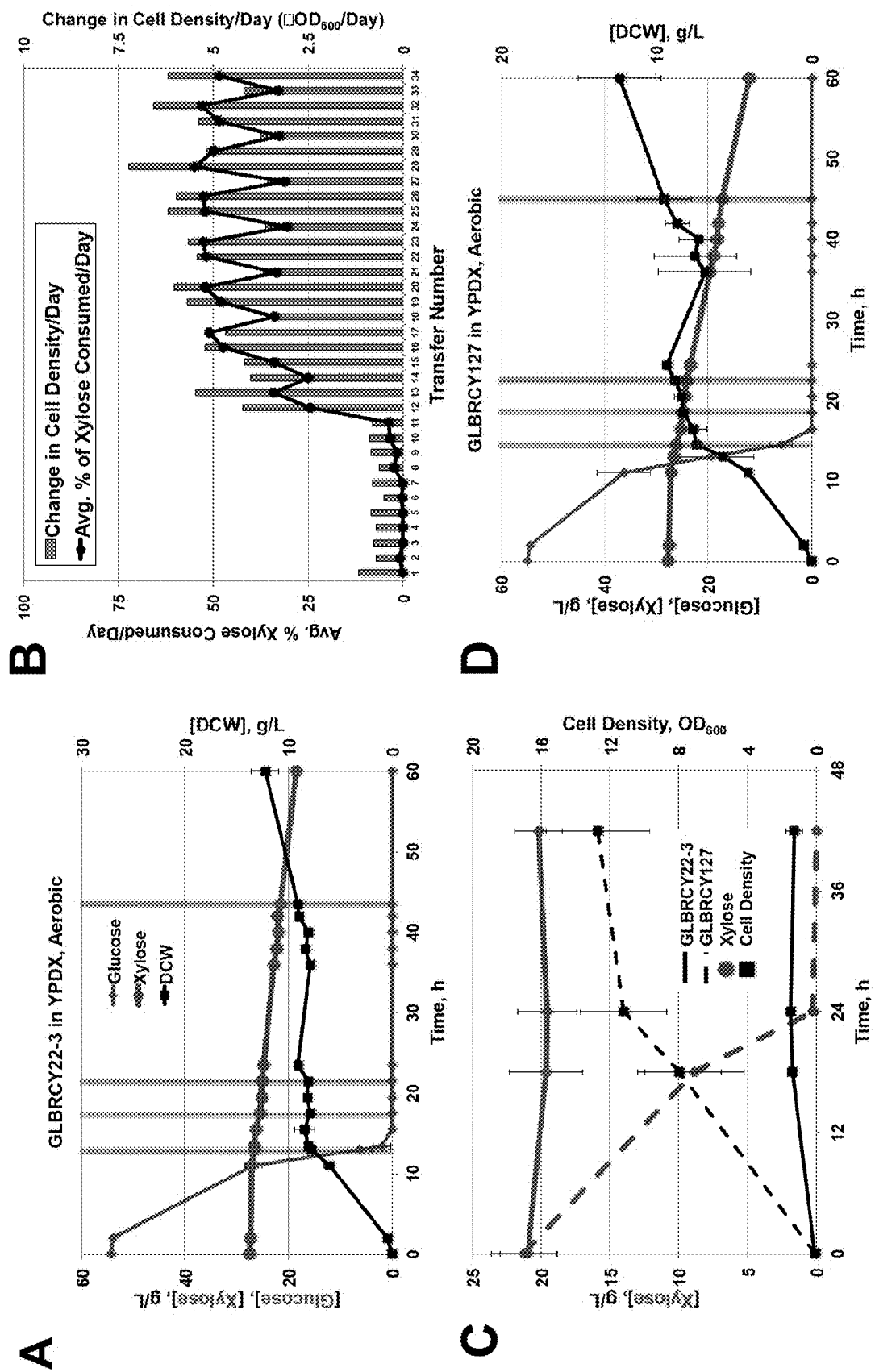
FIG. 3A-D

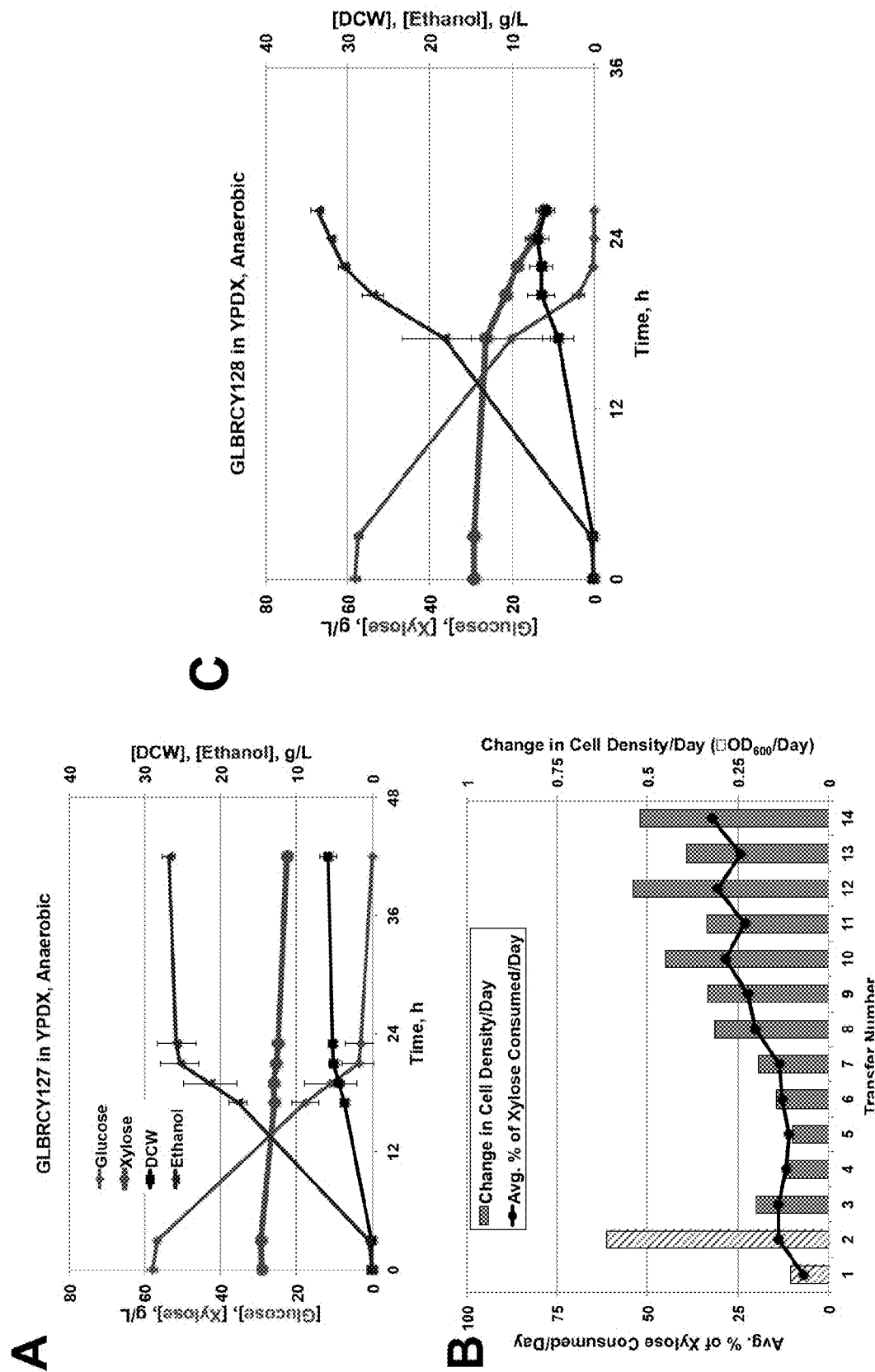
FIG. 4A-C

FIG. 5A-C
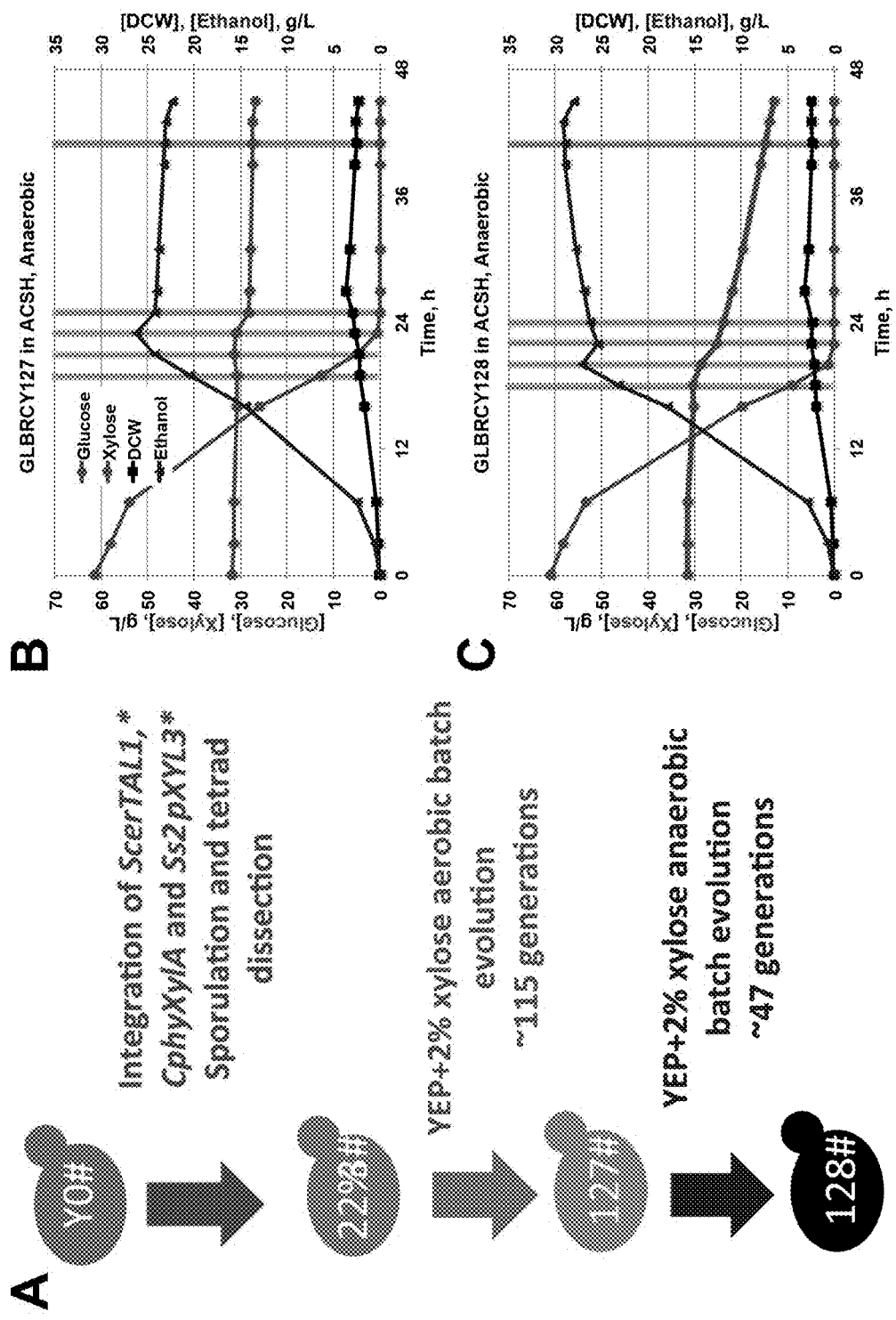

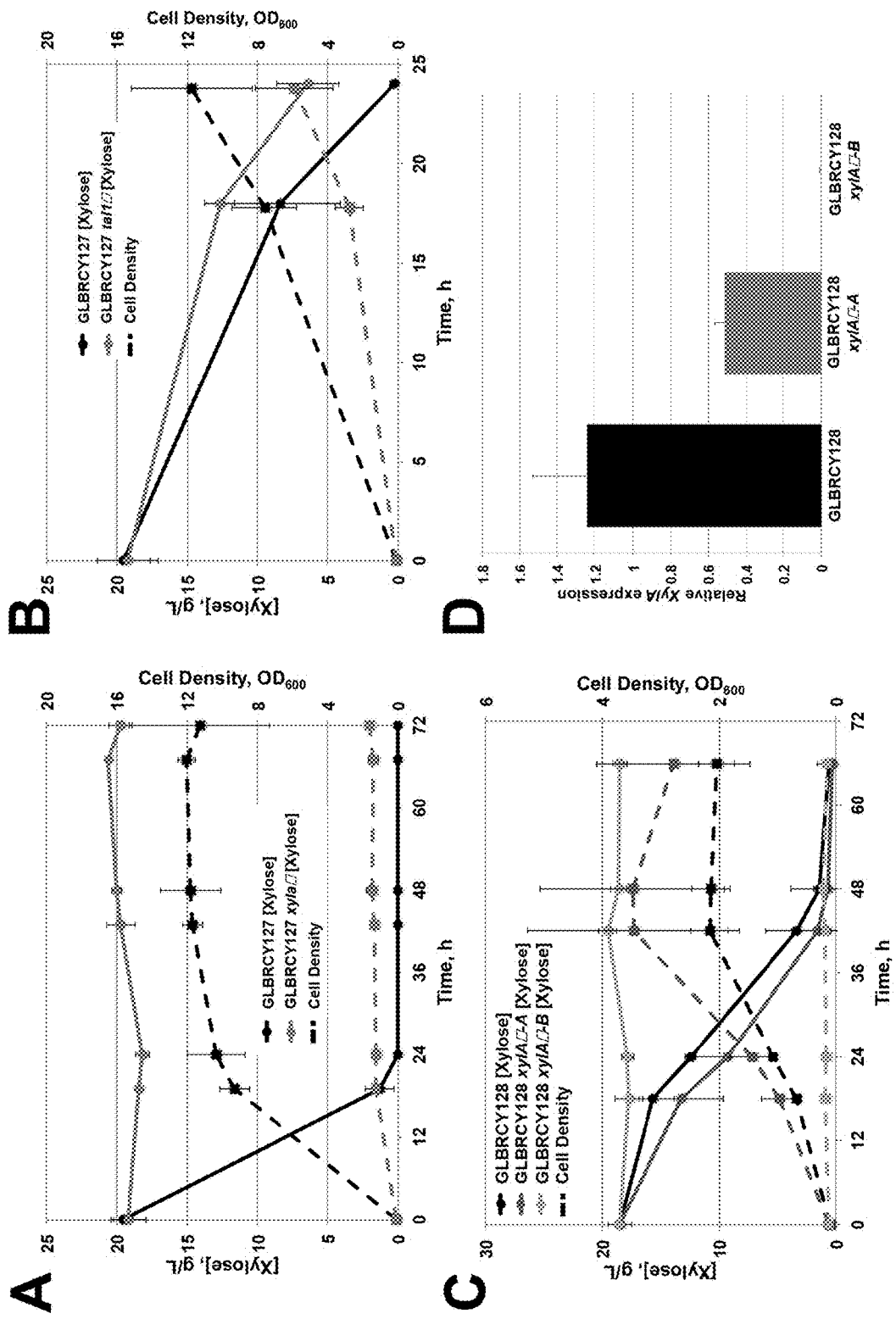
FIG. 6A-D

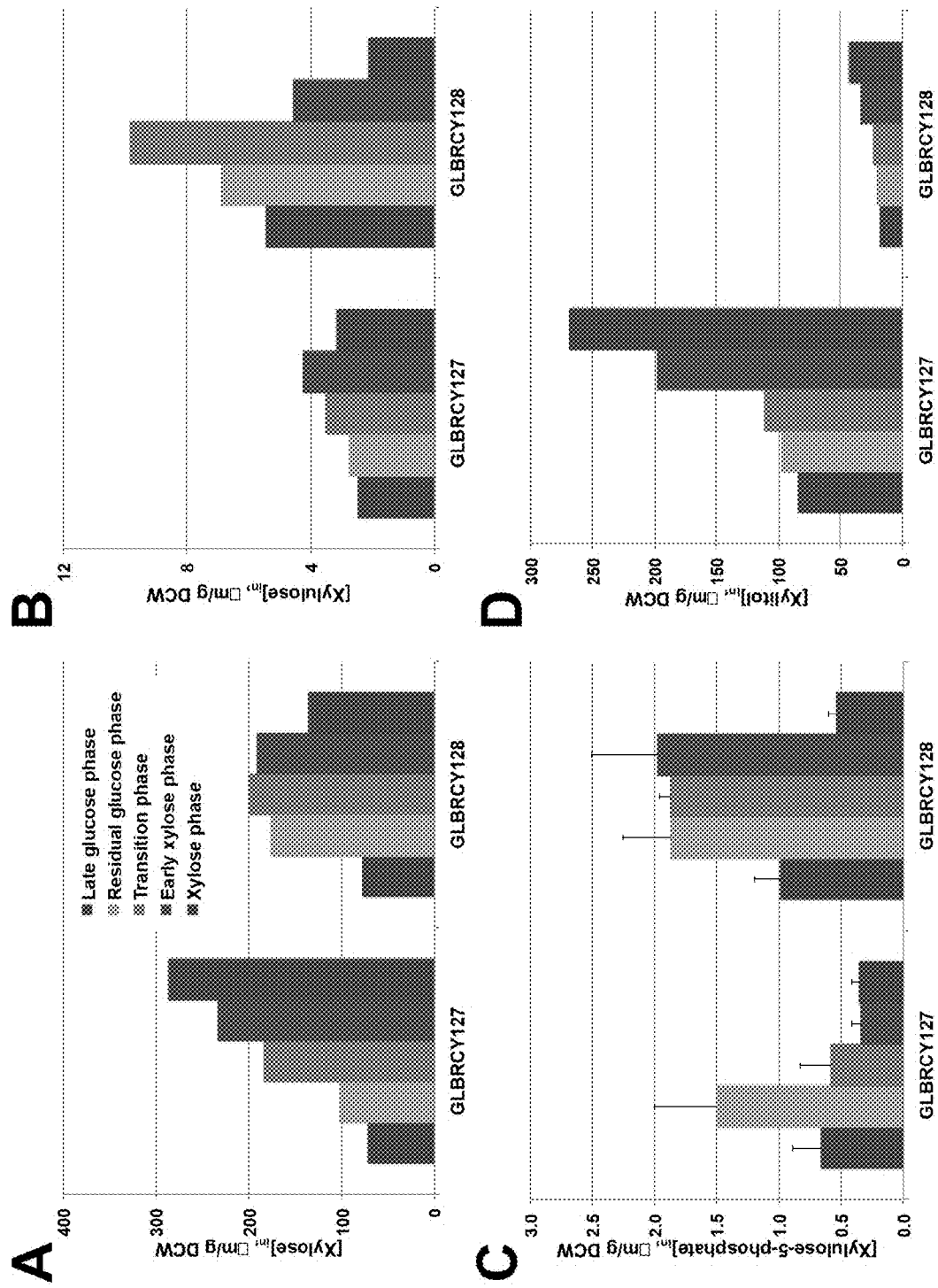
FIG. 7A-D

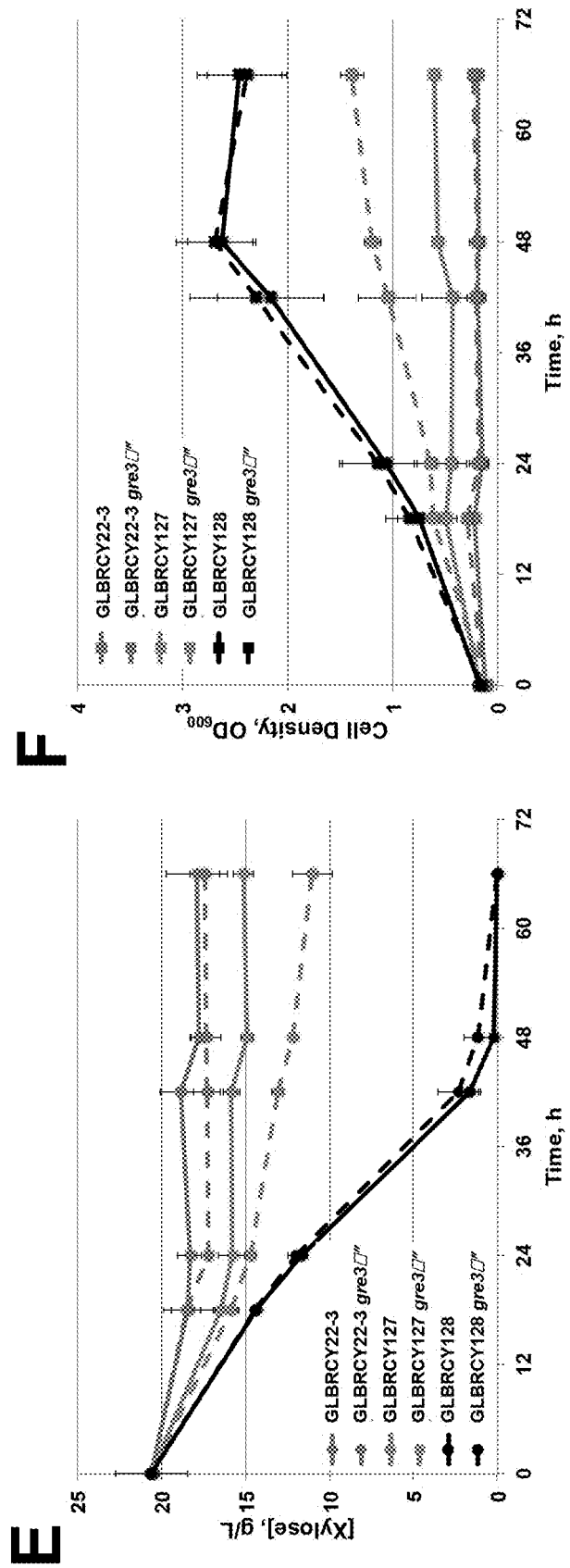
FIG. 7, CONTINUED
FIG. 7E-F

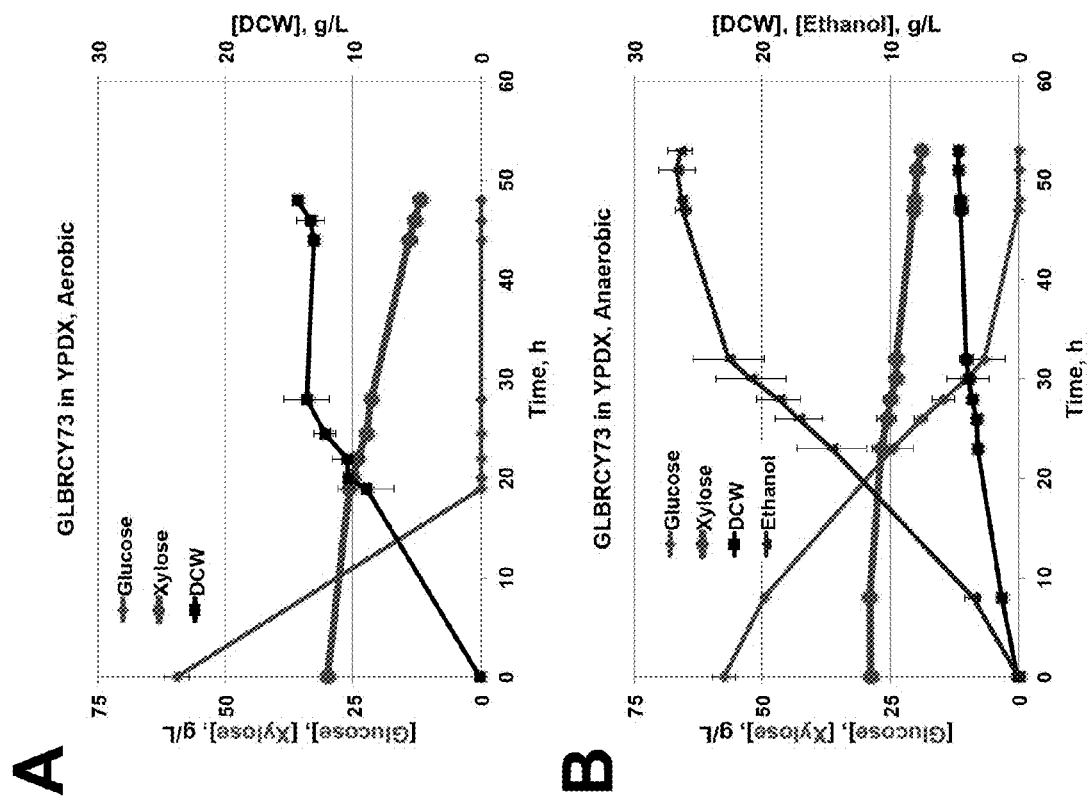
FIG. 8A-B

FIG. 8, CONTINUED

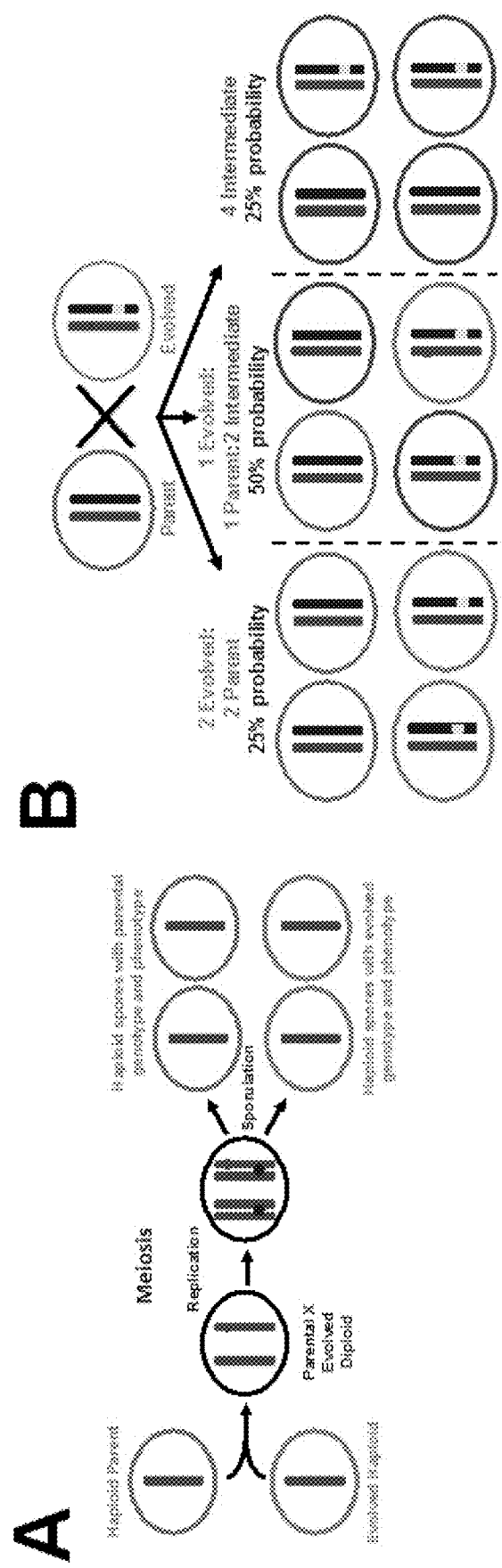
FIG. 9A-B

FIG. 9, CONTINUED
FIG. 9C-F
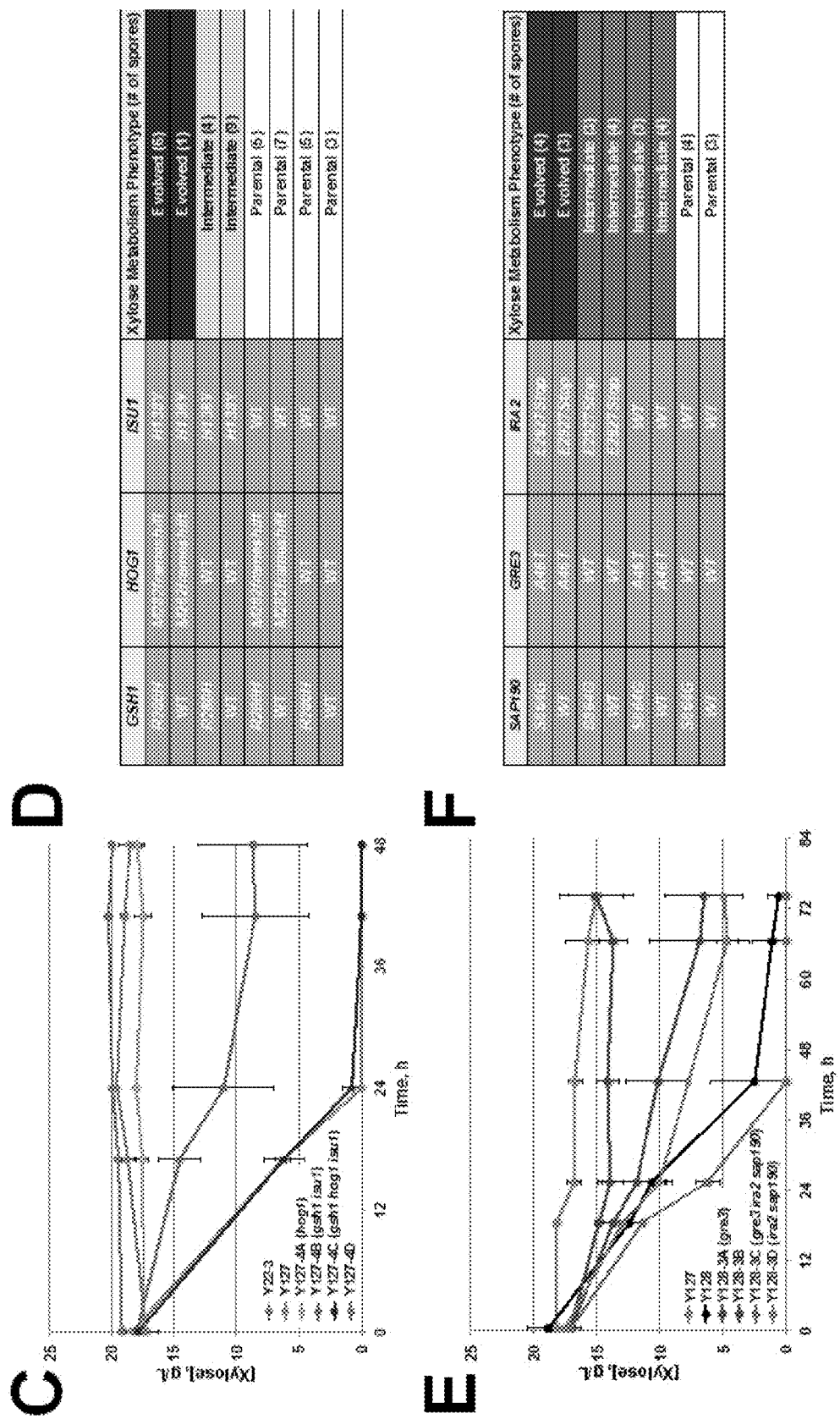

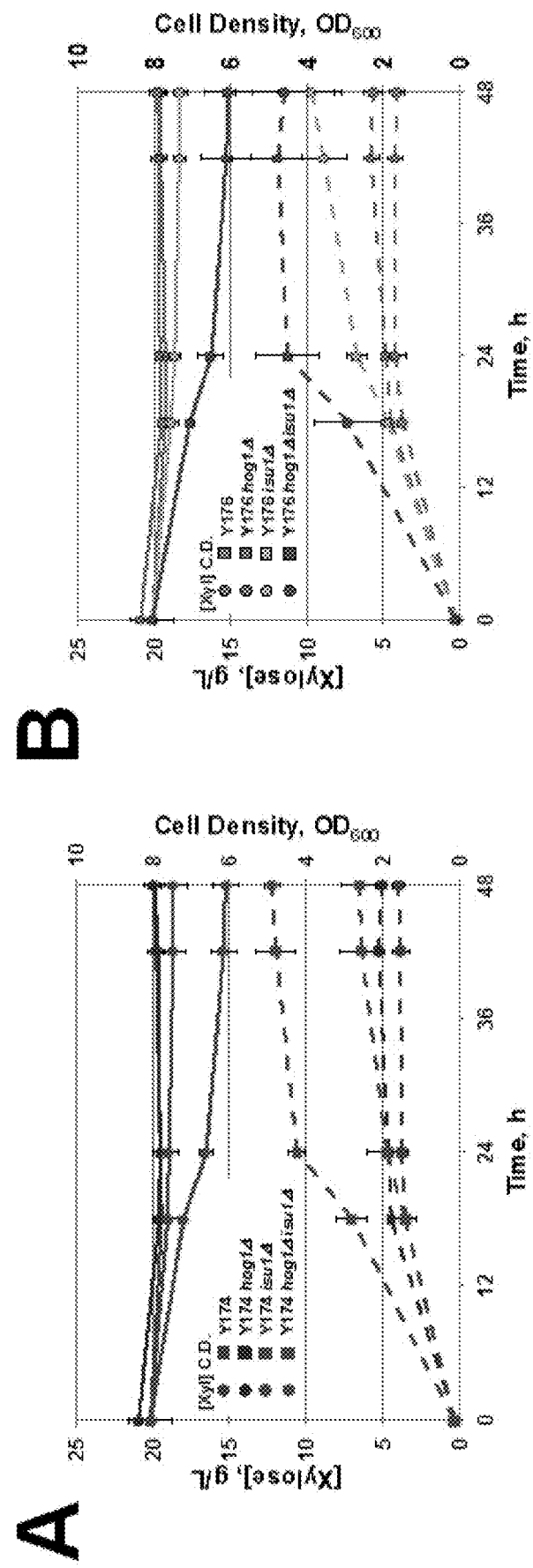
FIG. 10A-B

FIG. 11A-B
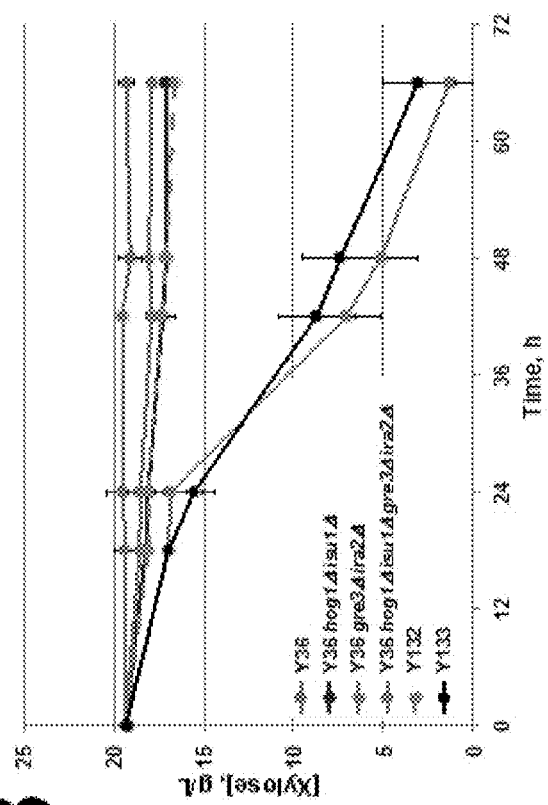
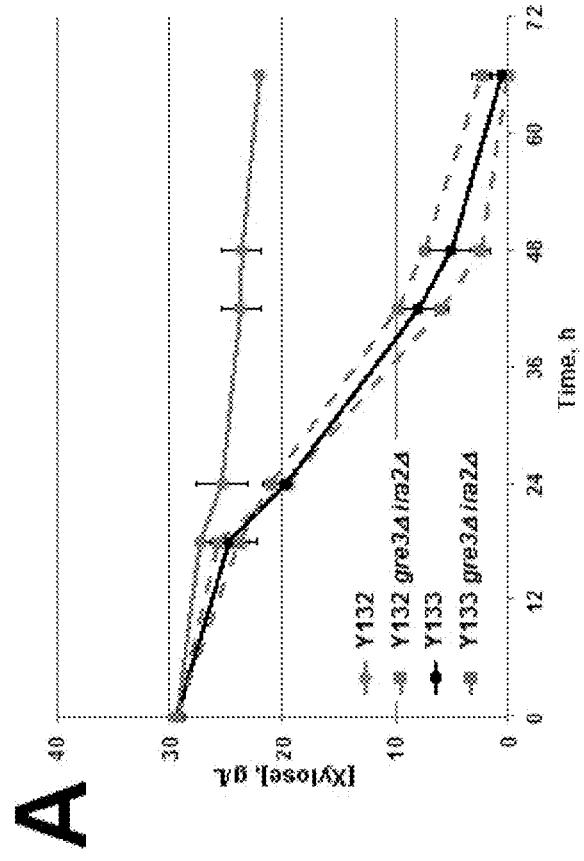

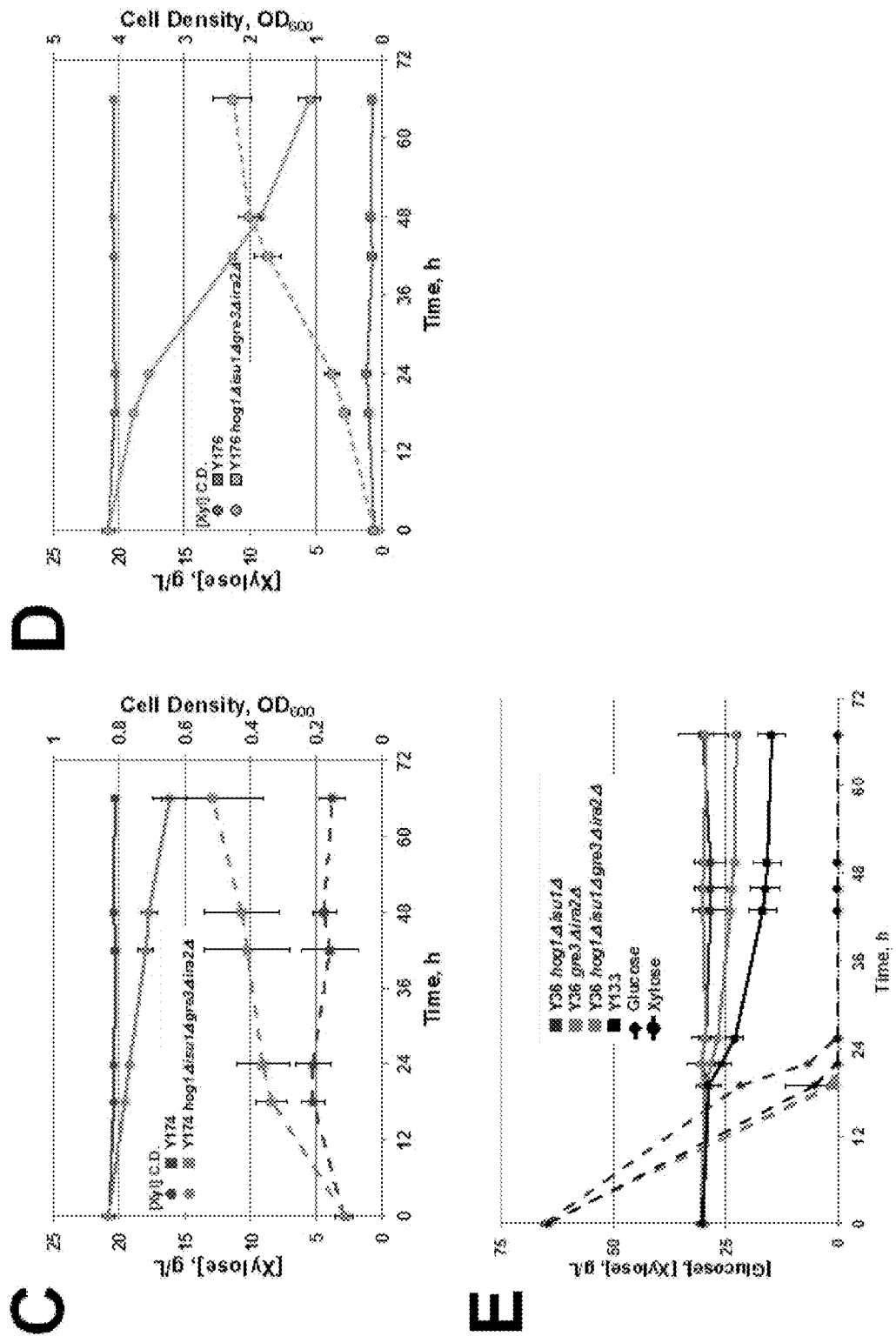
FIG. 11, CONTINUED
FIG. 11C-E

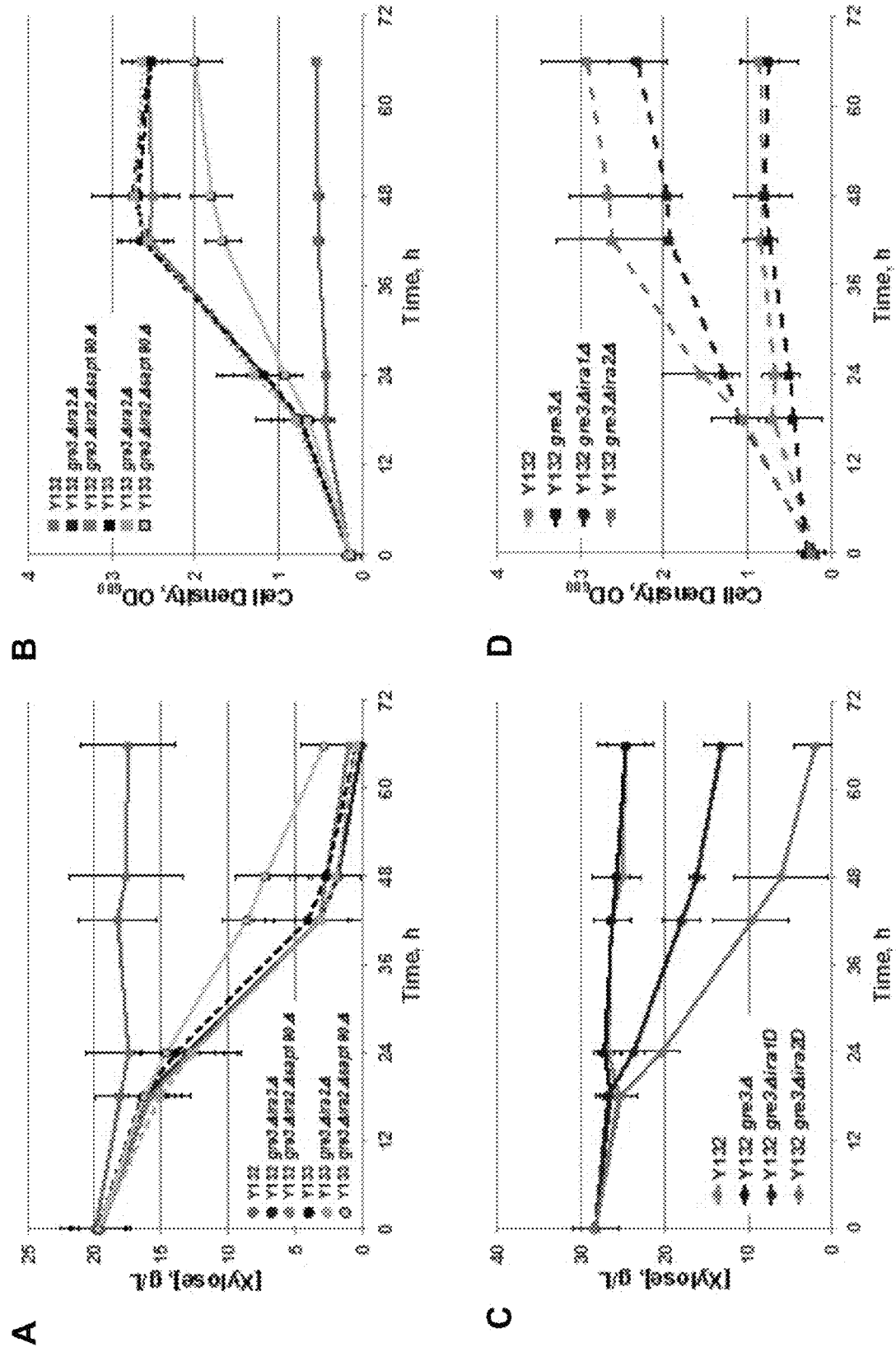
FIG. 12A-D

RECOMBINANT YEAST HAVING ENHANCED XYLOSE FERMENTATION CAPABILITIES AND METHODS OF USE

CROSS-REFERENCE TO RELATED APPLICATIONS

This application claims the benefit of U.S. Provisional Patent Application No. 61/978,585, filed Apr. 11, 2014; which is incorporated herein by reference as if set forth in its entirety.

STATEMENT REGARDING FEDERALLY SPONSORED RESEARCH OR DEVELOPMENT

This invention was made with government support under DE-FC02-07ER64494 awarded by the U.S. Department of Energy. The government has certain rights in the invention.

FIELD OF THE INVENTION

Broadly, the present invention relates to materials and methods for the production of biofuels and other industrially relevant products from plant materials such as chemical feedstocks. In particular, the present invention relates to genetically modified yeast strains useful for xylose fermentation and, more specifically, to strains of *Saccharomyces cerevisiae* genetically engineered for enhanced xylose fermentation capabilities and methods of using the same for improved fermentation of cellulosic materials comprising pentose sugars and for industrial-scale production of biofuels and plant-derived chemical feedstocks.

BACKGROUND

Cellulosic biomass is a vast source of renewable energy and an abundant substrate for biofuel production. As an alternative to corn-based ethanol, bioethanol can be generated from lignocellulosic (LC) sugars derived from cellulosic biomass of renewable and sustainable plant feedstocks. Energy of cellulosic biomass is primarily stored as the recalcitrant polysaccharide cellulose, which is difficult to hydrolyze because of the highly crystalline structure, and in hemicellulose, which presents challenges because of its structural diversity and complexity. Many microbes cannot natively ferment pentose sugars (e.g., xylose) from complex lignocellulosic biomass, which is composed of cellulose, hemicellulose and lignin fractions. Even when engineered to express the minimal enzymes from native pentose sugar-metabolizing organisms, *S. cerevisiae* cannot ferment xylose from innocuous lab media at industrially-acceptable rates. Laluce et al., *Applied Microbiol. Biotech.* 166:1908 (2012); Almeida et al., *Biotech. J.* 6:286 (2011). Xylose is a prevalent sugar in both woody and herbaceous plants and a major component of hemicelluloses. Bioconversion of both xylose and glucose is required for the production of cellulosic biofuels. To further complicate matters, plant biomass must be chemically, mechanically, or thermally pretreated prior to enzymatic hydrolysis ex situ in order to produce fermentable glucose and xylose monomers. Such pretreatment processes generate a diverse array of degradation products derived from plant cell walls, such as hemicellulose and lignin-derived acetate and aromatic molecules, many of which inhibit cellular metabolism in *S. cerevisiae* and induce microbial stress during hydrolysate fermentation. Taylor et al., *Biotechnology J.* 7:1169 (2012); Liu, *Applied Microbiol. Biotech.* 90:809 (2011). At present, little is known about how such inhibitors impact xylose fermentation, particularly under strict industrially relevant, anaerobic conditions where ethanol production is maximized.

In view of the current state of the biofuel industry, particularly ethanol production based on xylose-containing feedstocks, it can be appreciated that identifying genes related to enhanced biofuel production is a substantial challenge in the field. Accordingly, a need exists in the field to identify additional genes that influence biofuel production in yeast, and consequently engineer recombinant strains of yeast capable of increased biofuel yields from commonly-available feedstocks, including xylose-containing feedstocks.

SUMMARY OF THE INVENTION

The present invention is largely related the inventors' research efforts to better understand xylose utilization for microbial engineering. The invention relates generally to methods and compositions for digesting lignocellulosic material and more particularly to methods that involve exposing the material to *S. cerevisiae* variants having enhanced capacities for anaerobic and aerobic xylose fermentation in industrially relevant lignocellulosic hydrolysates.

In a first aspect, provided herein is a recombinant yeast that has been genetically engineered to exhibit reduced amounts of functional Isu1 polypeptide. The genetically engineered recombinant yeast is capable of increased aerobic xylose fermentation relative to a wild-type yeast or another recombinant yeast not exhibiting reduced amounts of functional Isu1 polypeptide. The recombinant yeast can comprise a disabling mutation in a gene encoding Isu1 polypeptide. The disabling mutation can comprise a substitution of a tyrosine for the histidine at amino acid residue position 138 of SEQ ID NO:6. The recombinant yeast can further comprise a disabling mutation in a gene encoding Hog1 polypeptide and exhibiting reduced amounts of functional Hog1 polypeptide. The disabling mutation in a gene encoding Isu1 can comprise a substitution of a tyrosine for the histidine at amino acid residue position 138 of SEQ ID NO:6, and the disabling mutation in the gene encoding Hog1 can comprise a deletion of the adenine at nucleotide position 844 of SEQ ID NO:7. The recombinant yeast can be of the genus *Saccharomyces*. The recombinant yeast can be of the species *Saccharomyces cerevisiae*. A portion of an extrachromosomal vector stably maintained in the recombinant yeast can comprise the disabling mutation. A nucleic acid sequence comprising the disabling mutation can be integrated into a chromosome of the recombinant yeast.

In another aspect, provided herein is a yeast inoculum comprising a recombinant yeast as provided herein and a culture medium.

In a further aspect, provided herein is a recombinant yeast that has been genetically engineered to exhibit reduced amounts of functional Isu1 and Hog1 polypeptides, and at least one of functional Gre3, Ira1, and Ira2 polypeptides. The recombinant yeast can be capable of increased anaerobic xylose fermentation relative to a wild-type yeast or another recombinant yeast not exhibiting reduced amounts of functional Isu1 and Hog1 polypeptides, and at least one of functional Gre3, Ira1, and Ira2 polypeptides. The recombinant yeast can comprise a disabling mutation in a gene encoding Isu1, a disabling mutation in a gene encoding Hog1, and at least one of a disabling mutation in a gene encoding Gre3, a disabling mutation in a gene encoding Ira1, and a disabling mutation in a gene encoding Ira2. The recombinant yeast can exhibit reduced amounts of functional Isu1, Hog1, Gre3, and Ira2 polypeptides and can be capable of increased anaerobic xylose fermentation relative to a wild-type yeast or another recombinant yeast not exhibiting reduced amounts of functional Isu1, Hog1, Gre3, and Ira2 polypeptides. The disabling mutation in the gene encoding Isu1 can comprise a substitution of a tyrosine for the histidine at amino acid residue position 138 of SEQ ID NO:6; a disabling mutation in the gene encoding Hog1 can comprise a deletion of the adenine at nucleotide position 844 of SEQ ID NO:7; a disabling mutation in the gene encoding Gre3 can comprise a substitution of a threonine for the alanine at amino acid residue position 46 of SEQ ID NO:4; and a disabling mutation in the gene encoding Ira2 can comprise a substitution of a stop codon for the glutamate at amino acid residue at position 2927 of SEQ ID NO:2. The recombinant yeast can be of the genus *Saccharomyces*. The recombinant yeast can be of the species *Saccharomyces cerevisiae*. A portion of an extrachromosomal vector stably maintained in the recombinant yeast can comprise the disabling mutations. A nucleic acid sequence comprising the disabling mutations can be integrated into a chromosome of the recombinant yeast.

In another aspect, provided herein is a yeast inoculum comprising a recombinant yeast as provided herein and a culture medium.

In a further aspect, provided herein is a method of fermenting cellulosic material into ethanol. The method can comprise contacting under ethanol-producing conditions a recombinant yeast provided herein to cellulosic material for a period of time sufficient to allow fermentation of at least a portion of the cellulosic material into ethanol. The method can further comprise separating the ethanol from fermented cellulosic material. The method can further comprise hydrolyzing the cellulosic material to produce a hydrolysate comprising xylose; and contacting the recombinant yeast to the hydrolysate under conditions that permit fermentation. The cellulosic material can comprise a lignocellulosic biomass. The lignocellulosic biomass can comprise at least one material selected from the group consisting of agricultural residues, wood, municipal solid wastes, paper and pulp industry wastes, and herbaceous crops.

As can be appreciated, the present invention contemplates the use of recombinant yeast as described herein, including certain exemplary recombinant *Saccharomyces cerevisiae* strains specifically identified herein, for use in the fermentation of xylose-containing cellulosic materials and for production of ethanol.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

The patent or application file contains at least one drawing executed in color. Copies of this patent or patent application publication with color drawings(s) will be provided by the Office upon request and payment of the necessary fee.

FIG. 2 demonstrates that phenotypic screening of wild and domesticated *S. cerevisiae* strains identified NRRL YB-210 as tolerant to a variety of pretreated lignocellulosic hydrolysates. In FIG. 2A, 117 *S. cerevisiae* strains (including some in duplicate) were cultured in 96-well plates and monitored for changes in cell density and growth rates. All strains in each condition were then ranked from 1 (highest growth rate in yellow) to 117 (lowest growth rate, or no growth, in blue) and hierarchically clustered. Arrows indicate clustered rows for BY4741 (green), CEN.PK2 (black) in duplicate microtiter wells, and NRRL YB-210/GLBRCY0 (red). Representative growth data for the YB-210/GLBRCY0 strain in the indicated media from FIG. 2A are plotted (FIGS. 2B-C). YP: Yeast Extract and Peptone supplementation; 6%: 6% glucan loading ACSH; 9%: 9% glucan loading ACSH; Dtx: Detoxified.

FIG. 3 demonstrates rapid aerobic xylose consumption by the GLBRCY127 strain, developed by directed engineering with xylose isomerase coupled with batch evolution. Average sugar consumption and cell growth of unevolved GLBRCY22-3 strain engineered with ScTAL1, CpXylA and SsXYL3 cultured in bioreactors containing YPDX media and sparged with air from biological duplicates is shown (FIG. 3A). Indicated components were quantified from media samples at times from initial inoculation. In FIG. 3B, the average percentage of xylose consumed and change in cell density per day are plotted for each transfer during the adaption of the Y22-3 strain in YP media containing 0.1% glucose and 2% xylose. The pattern of lower % of xylose consumed and change in cell density per day during every third transfer is due to reaching saturated growth prior to transfer. Average extracellular xylose concentrations and cell density measurements from parental GLBRCY22-3 and evolved Y127 strains grown aerobically in culture tubes with YPX media from three independent biological replicates are plotted in FIG. 3C. In FIG. 3D, evolved isolate GLBRCY127 was cultured in the same conditions as in FIG. 3A, and sample measurements were taken in an identical manner. Vertical bars indicate time points for metabolomic sampling described in FIG. 7.

FIG. 4 depicts second stage anaerobic adaptation on xylose for rapid xylose fermentation by GLBRCY128. A representative experiment (of two biological reps) of the GLBRCY127 strain cultured in bioreactors containing YPDX media and sparged with nitrogen is shown (FIG. 4A). Indicated components were quantified from media samples at times from initial inoculation. In FIG. 4B, the percentage of xylose consumed and change in cell density per day is plotted for each transfer during the anaerobic adaptation of the Y127 strain in YP media containing 0.1% glucose and 2% xylose. In the first two transfers (hatched bars), Tween-80 and ergosterol were added to the media. In FIG. 4C, evolved isolate GLBRCY128 was cultured in the same conditions as in FIG. 4A, and samples measurements taken in an identical manner.

FIG. 5 depicts the ability of GLBRCY128 to anaerobically ferment xylose from ACSH. A diagram summarizing the engineering and evolution of the GLBRCY0 strain to the evolved Y128 strain is provided in (FIG. 5A). Representative experiments (of two biological reps) of the Y127 (FIG. 5B) and Y128 (FIG. 5C) strains cultured in bioreactors containing ACSH and sparged with nitrogen are shown. Indicated components were quantified from media samples at times from initial inoculation. Vertical bars indicate time-points at which samples were taken for metabolomic analysis described in FIG. 7B.

FIG. 6 demonstrates that xylose consumption phenotypes of the evolved Y127 and Y128 strains are dependent upon CpXylA and ScTALJ. Extracellular xylose concentrations (solid lines) and cell density (dashed lines) were measured by YSI instrument and optical density 600 readings, respectively, from cultures containing (FIG. 6A) GLBRCY127 and GLBRCY127 xylAΔ or (FIG. 6B) Y127 and Y127 tal1Δ strains inoculated in aerobic YPX media. In FIG. 6C, extracellular xylose concentrations (solid lines) and cell density (dashed lines) were measured as in FIGS. 6A-B for GLBRCY128 and two independent GLBRCY128 xylAΔ strains inoculated in anaerobic YPX media. These Y128 strains were cultured in YPD media and total RNA isolated from a single timepoint. Expression of CpXylA was then quantified and normalized to ScERV25 RNA levels by qPCR. The bar graph in FIG. 6D displays the average values and standard deviations for CpXylA RNA from three independent biological replicates.

FIG. 7 demonstrates reduced xylitol production and improved anaerobic xylose fermentation in a variant (GLBRCY128) comprising a mutation in GRE3. Fermentation samples were taken at the indicated timepoints marked by vertical bars in FIGS. 5B-C. Cells were filter-captured, briefly washed and then intracellular metabolites extracted by solvent. Identification and concentrations of xylose (FIG. 7A), xylulose (FIG. 7B), xylulose-5-phosphate (FIG. 7C), and xylitol (FIG. 7D) were determined by reverse phase ion pairing HPLC-ESI coupled with MS/MS or gas chromatography (see Example 3). Average concentrations and standard deviations are based on two biological replicates. Y22-3, Y127, and Y128 strains (with or without deletion of GRE3) were cultured under anaerobic conditions. Samples were taken at the indicated time-points to measure xylose concentrations (FIG. 7E) or cell density (FIG. 7F). Average values and standard deviations were calculated from biological triplicates.

FIG. 9 presents a schematic and data demonstrating co-segregation two mutations co-segregate with the evolved xylose metabolism phenotypes. Schematic diagrams summarizing the segregation of genotypes and phenotypes in the progeny from a parent×evolved backcross for one (FIG. 9A) or two (FIG. 9B) unlinked driver mutations (green or yellow boxes) on chromosomes (red or blue rectangles). In FIG. 9B, progeny with a single evolved mutation have intermediate phenotypes; however, driver mutations can also have parental-like phenotypes. Probabilities for progeny genotypes are indicated based on random chromosomal segregation. Haploid progeny isolated from a backcross between parental Y22-3 and aerobically evolved Y127 (FIGS. 9C, D) or between parental Y127 and anaerobically evolved Y128 (FIGS. 9E, F) were genotyped and phenotyped for aerobic or anaerobic xylose consumption, respectively. Data in (FIG. 9C) and (FIG. 9E) are representative examples for progeny from the Y22-3×Y127 and Y127×Y128 backcrosses, respectively. Tables in (FIG. 9D) and (FIG. 9F) summarize the genotypes of analyzed spores and qualitative comparison of xylose consumption phenotype relative to the Parental and Evolved strains. Strains that consumed xylose at rates intermediate of the Parent and Evolved were designated with "Intermediate" phenotypes. Xylose consumption phenotypes were determined from the average of biological duplicates.

FIG. 10 presents data demonstrating that identical mutations in lab strain backgrounds phenocopy anaerobic xylose metabolism. BY4741 (FIG. 10A) and CEN.PK113-5D (FIG. 10B) lab strains engineered to express xylose metabolism enzymes (Y174 and Y176, respectively) were engineered with null mutations in the indicated gene. Strains were cultured either aerobically in YPX media, with cell densities and xylose concentrations sampled at the indicated times. Averages and standard deviations of biological triplicates are shown.

FIG. 11 demonstrates that null mutations in HOG1, ISU GRE3, and IRA2 are sufficient for anaerobic xylose consumption. Combinations of hog1, isu1, gre3 and ira2 null mutations were introduced into the Y132, Y133 (FIG. 11A) or Y36 (FIGS. 11B and C) strain backgrounds. The resulting strains were cultured in YPX media under anaerobic conditions. Specific xylose consumption rates (g xylose consumed $h^{-1}$ cell mass$^{-1}$ in g DCW or $OD_{600}$ units) were calculated from biological triplicates. In FIG. 11B, statistically significant differences ($p<0.05$) by paired t-test are indicated (*) between Y36 isu1Δhog1Δira2Δ or Y36 isu1Δhog1Δ gre3Δ ira2Δ compared to Y36 hog1Δisu1Δ or Y36 gre3Δ ira2Δ.

FIG. 12 demonstrates that activation of PKA signaling by deletion of IRA genes confers capacity for anaerobic xylose fermentation. Strains harboring various null mutations in GRE3, IRA2, along with SAP190 (FIGS. 12A-B) or IRA1 (FIGS. 12C-D) within the Y132 or Y133 strain backgrounds were phenotyped by anaerobic xylose metabolism in YPX media. Average cell densities and xylose concentrations, as well as standard deviations, from independent biological duplicates sampled at the indicated times are shown.

Figure 1:
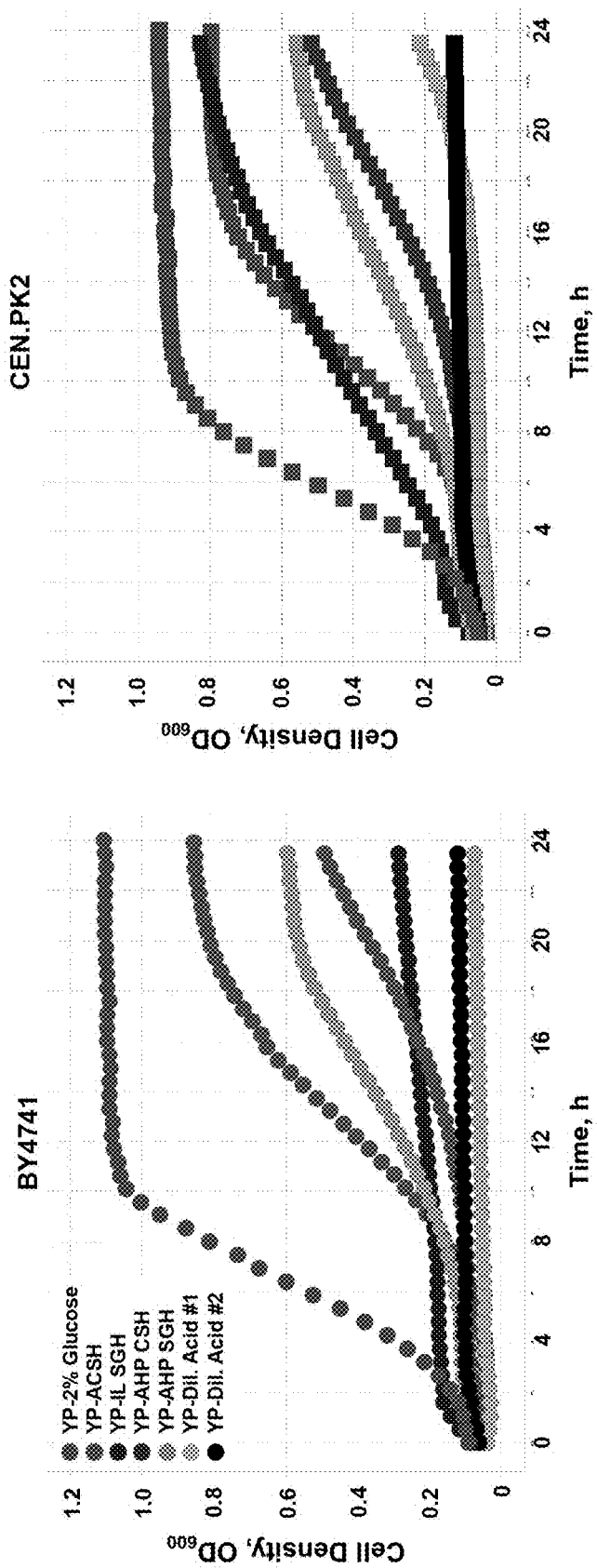
FIG. 1 presents data demonstrating xylose consumption in lab strain backgrounds. ACSH; 6% glucan loading AFEX™ pretreated corn stover hydrolysate, AHP; Alkaline Hydrogen Peroxide pretreatment, IL; Ionic Liquid ([$C_2$mim][OAc]) pretreated, Dil. Acid; Dilute Acid pretreated hydrolysate, SGH; switchgrass hydrolysate, CSH; corn stover hydrolysate.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION OF THE INVENTION

All publications, including but not limited to patents and patent applications, cited in this specification are herein incorporated by reference as though set forth in their entirety in the present application.

Compositions of the Invention

Efficient fermentation of cellulosic feedstock is an essential step in the production of biofuel from plant materials. While *S. cerevisiae* excels at fermentation of glucose from corn and sugar cane, the fermentation of renewable lignocellulosic biomass presents a significant challenge. Xylose, which is a pentose sugar and a major component of hemicellulose, can comprise almost 30% of total cell wall carbohydrate in grasses. Its conversion, along with glucose, into ethanol is critical for any economically-viable cellulosic biofuel process. However, native *S. cerevisiae* cannot efficiently ferment xylose, as most strains have either lost or downregulated the activities of xylose catabolism proteins. Even when engineered to express the minimal enzymes from native xylose metabolizing organisms, *S. cerevisiae* is still unable ferment xylose from innocuous lab media at industrially-acceptable rates. However, several Ascomycete yeasts that both ferment and assimilate xylose have been identified, including *Pichia stipitis*, whose genome has recently been sequenced. The present invention is based, at least in part, on the Inventors' discovery of genetic modifications that permit substantially faster xylose fermentation under anaerobic conditions—conditions preferred for industrial ethanol production from plant biomass.

Accordingly, one aspect of the present invention relates to strains genetically engineered to be xylose-utilizing and ethanol-producing yeast strains. In particular, the present invention provides further genetic modifications to eukaryotic host cells that have been engineered to express xylose metabolism enzymes. Such further genetic modifications improve the efficiency of xylose metabolism in such host cells. In exemplary embodiments, modified host cells of the present invention are yeasts that have been additionally genetically engineered for enhanced anaerobic and/or aerobic xylose fermentation and increased ethanol production. The modified host cells of the present invention are well-suited for producing a variety of fermentation products, including ethanol, in fermentation processes that use xylose or a combination of xylose and glucose as carbon sources.

As used herein, a "host cell" is a cell which has been transformed or transfected, or is capable of transformation or transfection by an exogenous polynucleotide sequence. A host cell that has been transformed or transfected may be more specifically referred to as a "recombinant host cell." A preferred host cell is a host cell that is naturally capable of alcoholic fermentation, preferably, anaerobic alcoholic fermentation. Host cells may also exhibit a high tolerance to ethanol, low pH, organic acids, and/or elevated temperatures. Such characteristics or activities of the host cell may be naturally present in the host cell or may be introduced or modified by genetic modification.

Preferred host cells for the present invention include yeast cells, particularly yeast cells of the genus *Saccharomyces*. Preferred yeast species as host cells include *Saccharomyces cerevisiae, S. bulderi, S. barnetti, S. exiguus, S. uvarum, S. diastaticus, K. lactis, K. marxianus*, and *K fragilis*, of which yeast cells of the genus *Saccharomyces* and yeast cells of the species *Saccharomyces cerevisiae* are preferred. Yeasts of the genus *Saccharomyces* posses both a metabolic pathway and a fermentative pathway for respiration.

"Yeasts" are eukaryotic micro-organisms classified in the kingdom Fungi. Most reproduce asexually by budding, although some yeasts undergo sexual reproduction by meiosis. Yeasts are unicellular, although some species with yeast forms may become multi-cellular through the formation of a string of connected budding cells known as pseudohyphae, or false hyphae, as seen in most molds. Yeasts do not form a single taxonomic or phylogenetic grouping. The term "yeast" is often taken as a synonym for *Saccharomyces cerevisiae*, but the phylogenetic diversity of yeasts is illustrated by their assignment to two taxonomic classes of fungi, the ascomycetes and the basidiomycetes. As used herein, wild type yeast refers to a yeast strain designated GLBRCY0 (YB-210). GLBRCY0/YB-210 is a strain of *S. cerevisiae* that can be obtained from the ARS Culture Collection, National Center for Agricultural Utilization Research, Peoria, Ill., USA; under NRRL YB-210.

A suitable host yeast cell contains at least one native gene (a "xylose isomerase gene") that produces an active xylose isomerase enzyme that is capable of catalyzing the interconversion of D-xylose to D-xylulose. Xylose isomerase can also catalyze the interconversion of D-ribose to D-ribulose and D-glucose to D-fructose. The enzyme can be specific to the reduction of xylose or non-specific (i.e., capable of catalyzing the conversion of a range of pentose sugars). In some cases, a suitable host yeast cell is genetically engineered to contain an expression cassette containing *Clostridium phytofermentans* xylose isomerase (CphytoXylA), which can confer anaerobic xylose fermentation by *S. cerevisiae* with additional genetic modifications (see Brat et al., *Applied Environmental Microbiol.* 75:2304 (2009)), driven by the ScerTDH3 promoter. In exemplary embodiments, the expression cassette further comprises ScerTAL1, a Pentose Phosphate Pathway transaldolase enzyme that can improve xylose metabolism when overexpressed (see Ni et al., *Applied Environmental Microbiol.* 73:2061 (2007); Walfridsson et al., *Applied Environmental Microbiol.* 61:4184 (1995)), and SstipXYL3 driven by the ScerPGK1 and ScerTEF2 promoters, respectively. For example, the host yeast cell can comprise a TAL1-XylA-XYL3 gene expression cassette.

Recombinant yeast of the present invention can further comprise genetic modifications intended to delete or disrupt genes encoding certain polypeptides. By "delete or disrupt", it is meant that the entire coding region of the gene is eliminated (deletion), or the gene or its promoter and/or terminator region is modified (such as by deletion, insertion, or mutation) so that the gene no longer produces an active enzyme, or produces an enzyme with severely reduced activity. The deletion or disruption can be accomplished by genetic engineering methods, forced evolution or mutagenesis, and/or selection or screening.

Recombinant yeast of the present invention can comprise genetic modifications that cause reduced levels of functional Isu1, Gre3, Ira2, Ira1, and Hog1 polypeptides. Isu1 is a polypeptide required for mitochondrial iron-sulfur (Fe—S) protein biogenesis. Gre3 is an aldolase enzyme. Hog1 is a mitogen-activated protein (MAP) kinase involved in osmoregulation. Ira1 and Ira2 are Ras GTPase activating proteins that act as a negative regulators of cyclic AMP (cAMP) signaling. Consistent with their role as negative regulators of the Ras-cAMP pathway, disruption of either IRA2 or IRA1 decreases the rate at which Ras proteins hydrolyze GTP to GDP and increases intracellular cAMP levels (Tanaka et al., *Mol Cell Biol* 9(2):757-68 (1990)). The nucleotide and amino acid sequences of IRA2 (NCBI Gene ID: 854073) are set forth as SEQ ID NO:1 and SEQ ID NO:2, respectively. The nucleotide and amino acid sequences of GRE3 (NCBI Gene ID: 856504) are set forth as SEQ ID NO:3 and SEQ ID NO:4, respectively. The nucleotide and amino acid sequences of ISU1 (NCBI Gene ID: 855968) are set forth as SEQ ID NO:5 and SEQ ID NO:6, respectively. The nucleotide and amino acid sequences of HOG1 (NCBI Gene ID: 850803) are set forth as SEQ ID NO:7 and SEQ ID NO:8, respectively. The nucleotide and amino acid sequences of IRA1 (NCBI Gene ID: 852437) are set forth as SEQ ID NO:9 and SEQ ID NO:10, respectively.

In some cases, a recombinant yeast of the present invention can comprise a disabling mutation that substitutes a threonine amino acid residue for the alanine located amino acid residue position 46 of SEQ ID NO:4, whereby the yeast exhibits a reduced amount of functional Gre3 polypeptide. In other cases, a recombinant yeast of the present invention can comprise a disabling mutation that substitutes a stop codon for the glutamate at amino acid residue at position 2927 of SEQ ID NO:2, whereby the yeast exhibits a reduced amount of functional Ira2 polypeptide. Alternatively, a recombinant yeast comprises a disabling mutation in SEQ ID NO:9, whereby the recombinant yeast exhibits a reduced amount of functional Ira1. In other cases, a recombinant yeast of the present invention can comprise a disabling mutation that substitutes a tyrosine for the histidine at amino acid residue position 138 of SEQ ID NO:6, whereby the yeast exhibits a reduced amount of functional Isu1 polypeptide. In further cases, a recombinant yeast of the present invention can comprise a disabling mutation that deletes an adenine nitrogenous base at nucleotide position 844 of SEQ ID NO:7, whereby the deletion causes a codon frame-shift and the yeast exhibits a reduced amount of functional Hog1 polypeptide.

In exemplary embodiments, a recombinant yeast of the invention comprises a disabling mutation at each of loci isu1, gre3, hog1, and ira2, whereby the mutations result in reduced amounts of functional Isu1, Gre3, Hog1, and Ira2 polypeptides, respectively. In some cases, the disabling mutations include a missense mutation in the S. cerevisiae gene encoding Isu1, a missense mutation in the gene encoding Gre3, an aldolase enzyme, a missense mutation in the gene encoding Ire2, and a codon frame-shift mutation in the gene encoding Hog1. Deletion of GRE3 was previously shown to improve xylose fermentation in xylose isomerase-engineered S. cerevisiae strains (Traff et al., Applied and Environmental Microbiol. 67:5668 (2001)). In exemplary embodiments, a recombinant yeast of the present invention comprises a disabling mutation at the GRE3 locus that substitutes a threonine for the alanine at amino acid residue position 46 of SEQ ID NO:4; a disabling mutation at the IRA2 locus that substitutes a stop codon for the glutamate at amino acid residue at position 2927 of SEQ ID NO:2; a disabling mutation at the ISU1 locus that substitutes a tyrosine for the histidine at amino acid residue position 138 of SEQ ID NO:6; and a disabling mutation at the HOG1 locus that deletes an adenine nitrogenous base at nucleotide position 844 of SEQ ID NO:7.

Genetically modified yeasts of the present invention containing genetic modifications that reduce or disrupt expression of one or more of Isu1, Hog1, Gre3, Ira2, and Ira1 polypeptides are useful to ferment xylose pentose sugars to desirable fermentation products such as ethanol. As set forth in Table 4 of the Examples, genetically engineered yeast comprising disabling mutations at three loci (e.g., isu1Δhog1Δgre3Δ; isu1Δhog1Δira2Δ; isu1Δhog1Δira1Δ) or four loci (e.g., isu1Δhog1Δgre3Δ, and either ira1Δ or ira2Δ) exhibit substantially faster anaerobic xylose fermentation relative to controls. Anaerobic xylose fermentation was fastest for genetically engineered yeast comprising mutations in four loci (isu1Δhog1Δgre3Δ, and either ira1Δ or ira2Δ). Recombinant yeast described herein may not comprise null mutations at an IRA1 locus and an IRA2 locus since the double mutation is lethal. For aerobic xylose metabolism, a genetically engineered yeast comprises genetic modifications that reduces or disrupt Isu1 polypeptide expression. Such a genetically engineered yeast may have mutations at additional loci.

It is contemplated that certain additional genetic modifications may be necessary to produce other desirable characteristics and/or to enable the yeast cell to produce certain products at industrially-acceptable levels.

Genetic modification of the host cell can be accomplished in one or more steps via the design and construction of appropriate vectors and transformation of the host cell with those vectors. Nucleic acid constructs useful in the invention may be prepared in conventional ways, by isolating the desired genes from an appropriate host, by synthesizing all or a portion of the genes, or combinations thereof. Similarly, the regulatory signals, the transcriptional and translational initiation and termination regions, may be isolated from a natural source, be synthesized, or combinations thereof. The various fragments may be subjected to endonuclease digestion (restriction), ligation, sequencing, in vitro mutagenesis, primer repair, or the like. The various manipulations are well known in the literature and will be employed to achieve specific purposes.

The various nucleic acids and/or fragments thereof may be combined, cloned, isolated and sequenced in accordance with conventional ways. Standard techniques of molecular biology, microbiology, recombinant DNA, and immunology, which are within the skill of the art, are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

The nucleotides which occur in the various nucleotide sequences appearing herein have their usual single-letter designations (A, G, T, C or U) used routinely in the art. In the present specification and claims, references to Greek letters may either be written out as alpha, beta, etc. or the corresponding Greek letter symbols (e.g., α, β, etc.) may sometimes be used.

The term "isolated nucleic acid" used in the specification and claims means a nucleic acid isolated from its natural environment or prepared using synthetic methods such as those known to one of ordinary skill in the art. Complete purification is not required in either case. The nucleic acids of the invention can be isolated and purified from normally associated material in conventional ways such that in the purified preparation the nucleic acid is the predominant species in the preparation. At the very least, the degree of purification is such that the extraneous material in the preparation does not interfere with use of the nucleic acid of the invention in the manner disclosed herein. The nucleic acid is preferably at least about 85% pure, more preferably at least about 95% pure and most preferably at least about 99% pure.

Further, an isolated nucleic acid has a structure that is not identical to that of any naturally occurring nucleic acid or to that of any fragment of a naturally occurring genomic nucleic acid spanning more than three separate genes. An isolated nucleic acid also includes, without limitation, (a) a nucleic acid having a sequence of a naturally occurring genomic or extrachromosomal nucleic acid molecule but which is not flanked by the coding sequences that flank the sequence in its natural position; (b) a nucleic acid incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene. Specifically excluded from this definition are nucleic acids present in mixtures of clones, e.g., as those occurring in a DNA library such as a cDNA or genomic DNA library. An isolated nucleic acid can be modified or unmodified DNA or RNA, whether fully or partially single-stranded or double-stranded or even triple-stranded. A nucleic acid can be chemically or enzymatically modified and can include so-called non-standard bases such as inosine, as described in a preceding definition.

After each manipulation, the DNA fragment or combination of fragments (polynucleotides) may be inserted into the cloning vector, the vector transformed into a cloning host, e.g., E. coli, the cloning host grown up, lysed, the plasmid isolated and the fragment analyzed by restriction analysis, sequencing, combinations thereof, or the like. "Polynucleotide(s)" generally refers to any polyribonucleotide or polydeoxyribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

Targeted integration can be accomplished by designing a vector having regions that are homologous to the upstream (5'-) and downstream (3'-) flanks of the target gene. Either of both of these regions may include a portion of the coding region of the target gene. The gene cassette (including associated promoters and terminators if different from those of the target gene) and selection markers (with associated promoters and terminators as may be needed) can reside on a vector between the regions that are homologous to the upstream and downstream flanks of the target gene. Targeted cassette insertion can be verified by any appropriate method such as, for example, PCR. A host cell may be transformed according to conventional methods that are known to practitioners in the art. Electroporation and/or chemical (such as calcium chloride- or lithium acetate-based) transformation methods can be used. The DNA used in the transformations can either be cut with particular restriction enzymes or used as circular DNA. Methods for transforming yeast strains are described in WO 99/14335, WO 00/71738, WO 02/42471, WO 03/102201, WO 03/102152 and WO 03/049525; these methods are generally applicable for transforming host cells in accordance with this invention. Other methods for transforming eukaryotic host cells are well known in the art such as from standard handbooks, such as Sambrook and Russel (2001) "Molecular Cloning: A Laboratory Manual (3rd edition)," Cold Spring Harbor Laboratory, Cold Spring Harbor Laboratory Press, or F. Ausubel et al., eds., "Current protocols in molecular biology," Green Publishing and Wiley Interscience, New York (1987).

In another aspect, compositions of the present invention further include yeast inoculums comprising recombinant yeast as provided herein. A yeast inoculum of the present invention can comprise a recombinant yeast as provided herein and (b) a culture medium. In exemplary embodiments, the recombinant yeast is S. cerevisiae and the culture medium is a liquid culture medium. Yeast inocula of the present invention include large-scale preparations of sufficient quantities of viable yeast cells for use in, for example, xylose fermentation and other industrial ethanol-producing methods. A yeast inoculum of the present invention can be contacted to cellulosic material for xylose fermentation.

Methods of the Invention

The methods provided by the present invention involve the discovery and incorporation of genetic modifications into genes encoding certain polypeptides into a single host organism and the use of those organisms to convert xylose to ethanol. In particular, the present invention provides methods of fermenting cellulosic material comprising the 5-carbon sugar xylose under anaerobic or aerobic conditions, where the method comprises use of a recombinant yeast.

In exemplary embodiments, recombinant yeast of the present invention are used to make a useful fuel (e.g., ethanol) or plant material-derived chemical feedstock by converting xylose and other sugars under appropriate fermentation conditions. The sugars can come from a variety of sources including, but not limited to, cellulosic material. The cellulosic material can be lignocellulosic biomass. As used herein, the term "lignocellulosic biomass" refers to any materials comprising cellulose, hemicellulose, and lignin, wherein the carbohydrate polymers (cellulose and hemicelluloses) are tightly bound to the lignin. Generally, lignocellulosic material for making ethanol is feedstock such as corn stover, which consists of the stems, cobs, and leaves from the corn plants (i.e., the non-grain material). Corn stover is typically shredded by mechanical means and incorporated by tillage into topsoil for decomposition. In addition to lignocellulosic ethanol production from corn stover, other feedstocks such as sorghum, wheat, or another grain can be used. In some cases, lignocellulosic biomass comprises material selected from the group consisting of materials that comprise at least 75% cellulose, cellulose/hemicelluloses, xylose, biomass, and chitin. In other cases, the lignocellulosic biomass comprises at least one material selected from the group consisting of agricultural residues, wood, municipal solid wastes, paper and pulp industry wastes, and herbaceous crops. As used herein, the term "biomass" refers to a renewable energy source, is biological material from living or recently living organisms. As an energy source, biomass can either be used directly, or converted into other energy products such as biofuel. Biomass includes plant or animal matter that can be converted into fibers or other industrial chemicals, including biofuels. Industrial biomass can be grown from numerous types of plants, including *miscanthus*, switchgrass, hemp, corn, poplar, willow, sorghum, sugarcane, bamboo, and a variety of tree species, ranging from *eucalyptus* to oil palm (palm oil). Thus, biomass can include wood biomass and non-wood biomass.

In some cases, cellulosic material is contacted with one or more of the genetically engineered yeasts disclosed herein (e.g., a yeast strain genetically modified to exhibit reduced amounts of functional ISU1, GRE3, HOG1, IRA1, and/or IRA2 polypeptides) under anaerobic or aerobic conditions. For example, a method of fermenting cellulosic material can comprise contacting under anaerobic conditions a recombinant yeast as provided herein to cellulosic material for a period of time sufficient to allow fermentation of at least a portion of the cellulosic material. In exemplary embodiments, a recombinant yeast used according to the methods provided herein is *Saccharomyces cerevisiae*.

The fermentation process may be an aerobic or an anaerobic fermentation process. Anaerobic fermentation is herein defined as a fermentation process run in the absence of oxygen or in which substantially no oxygen is consumed, preferably less than 5, 2.5 or 1 mmol/L/h, more preferably 0 mmol/L/h is consumed (i.e., oxygen consumption is not detectable), and where organic molecules serve as both electron donor and electron acceptors. In the absence of oxygen, NADH produced in glycolysis and biomass formation cannot be oxidized by oxidative phosphorylation.

In some cases, the method can include a first hydrolyzation step. For example, when cellulosic material is used in the methods disclosed herein, the material can be hydrolyzed to produce a hydrolysate comprising xylose, which is subsequently contacted to one or more recombinant yeasts of the present invention. As used herein, the term "hydrolysate" refers to a fermentable sugar-containing product produced from cellulosic material (e.g., biomass), typically through pretreatment and saccharification processes. In general, cellulosic material is pretreated using thermal, physical, and/or chemical treatments, and saccharified enzymatically. Physical and chemical treatments may include grinding, milling, cutting, base treatment such as with ammonia or NaOH, and acid treatment. In some cases, plant biomass can be pretreated using AFEX™. While highly effective at pretreating grasses for enzymatic hydrolysis, AFEX™ pretreament generates diverse inhibitory compounds from corn stover that impair xylose fermentation (Schwalbach et al., *Applied Environ. Microbiol.* 78:3442 (2012); Koppram et al., *Biotechnol. Biofuels* 5:32 (2012); Lau & Dale, *PNAS USA* 106:1368 (2009)). The inhibitory compounds are degradation products derived from plant cell walls such as hemicellulose and lignin-derived acetate and aromatic molecules.

Enzymatic saccharification typically makes use of an enzyme composition or blend to break down cellulose and/or hemicellulose and to produce a hydrolysate containing 6-carbon sugars (e.g., glucose) and 5-carbon sugars (e.g., xylose, arabinose). For review of saccharification enzymes, see Lynd et al., *Microbiol. Mol. Biol. Rev.* 66:506-577 (2002). Saccharification enzymes may be obtained commercially. In some cases, saccharification enzymes may be produced using recombinant microorganisms that have been engineered to express one or more saccharifying enzymes.

In some cases, methods of the present invention further comprise an ethanol separation or extraction step. Following conversion of sugars into ethanol, the ethanol can be separated from a fermentation culture using, for example, a standard distillation method or by filtration using membranes or membrane systems known in the art. Methods of separating or extracting are not restricted to those disclosed herein.

Methods of the present invention can be conducted continuously, batch-wise, or some combination thereof.

In another aspect, provided herein are methods for producing fuels and chemical feedstocks from glycerol (or glycerin). Glycerol is a by-product of biodiesel production, which, using a recombinant yeast of the present invention, could be further converted to a fuel or chemical feedstock such as, for example, ethanol, lactic acid, isobutanol, and propanediol. In some cases, a method of converting glycerol to ethanol can comprise contacting glycerol to one or more of the genetically engineered yeasts disclosed herein (e.g., a yeast strain genetically modified to exhibit reduced amounts of functional ISU1, GRE3, HOG1, IRA1, and IRA2 polypeptides) under appropriate fermentation conditions. In exemplary embodiments, methods are provided for producing lactic acid from glycerol. In such cases, the method comprises contacting under anaerobic conditions a recombinant yeast provided herein to glycerol for a period of time sufficient to allow fermentation of at least a portion of the glycerol into lactic acid. Lactic acid is in high demand as a chemical feedstock for the biodegradable plastic known as polylactic acid (PLA), a biopolymer that is useful in a variety of applications including packaging material and medical devices (e.g., surgical sutures, orthopedic implants). The raw materials required to manufacture lactic acid are expensive and limit use of PLA. In other cases, the method of converting glycerol into a useful fuel comprises contacting under anaerobic conditions a recombinant yeast as provided herein to glycerol for a period of time sufficient to allow fermentation of at least a portion of the glycerol into ethanol or butanol.

In exemplary embodiments, a recombinant yeast used according to the methods provided herein is *Saccharomyces cerevisiae* (*S. cerevisiae*). Following conversion of glycerol into ethanol, the fuel or chemical feedstock can be separated from a fermentation culture using, for example, a standard distillation method or by filtration using membranes or membrane systems known in the art. Methods of separating or extracting are not restricted to those disclosed or exemplified herein.

Articles of Manufacture

In a further aspect, the present invention provides an article of manufacture containing any one or more of the recombinant yeasts disclosed herein is provided. An article of manufacture can contain one of the microorganisms disclosed herein (e.g., one or more of the yeast strains), or an article of manufacture can contain two or more of the microorganisms disclosed herein. Articles of manufacture disclosed herein also can include, for example, components necessary for growth of the particular microorganism(s).

It is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be limited only by the appended claims.

It must be noted that as used herein and in the appended claims, the singular forms "a," "an," and "the" include plural reference unless the context clearly dictates otherwise. As well, the terms "a" (or "an"), "one or more" and "at least one" can be used interchangeably herein. It is also to be noted that the terms "comprising," "including," and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The present invention will be more fully understood upon consideration of the following non-limiting Examples.

EXAMPLES

Example 1—Genetic Engineering and Two-Stage Directed Evolution of a S. cerevisiae Strain Tolerant to Pretreated Lignocellulosic Hydrolysates The primary goal of this research was to develop and characterize a S. cerevisiase strain that can effectively ferment xylose anaerobically from AFEX™-pretreated lignocellulosic biomass. First, two well-characterized laboratory strains, BY4741 and CEN.PK2 (Entian K D & Kötter P (2007) Yeast Genetic Strain and Plasmid Collections. (Academic Press, Amsterdam)), were evaluated for their potential to serve as starting points for this research by evaluating their general growth tolerance in lignocellulosic hydrolysates (LCHs) generated from a range of established pretreatments and feedstocks. While both strains reached saturated cell density within 8 hours after inoculation in YPD media, they grew at substantially slower growth rates and reached lower cell densities in the pretreated lignocellulosic hydrolysates (FIGS. 1A-B), even though glucose concentrations were significantly higher. These results are consistent previous studies reporting profound differences in xylose consumption between S. cerevisiae strains grown either in lab media and pretreated lignocellulosic hydrolysates (Koppram et al., Biotech. for Biofuels 5:32 (2012); Lau et al., PNAS 106(5):1368-73 (2009); Jin et al., Biotech. for Biofuels (2013); Sato et al., Applied and Environ. Microbiology 80:540 (2014)), which was largely due to inhibitory compounds generated from lignocellulose pretreatment. Moreover, these results indicate that both BY4741 and CEN.PK2 strains would not be sufficiently tolerant for fermentation of inhibitor-laden hydrolysates.

Based on these observations, we surmised that an alternative strain background with tolerance to these inhibitors would be necessary to achieve adequate xylose fermentation. To find such strain, we performed comprehensive phenotyping of a collection of publicly-available, wild and domesticated S. cerevisiae strains obtained from a variety of locations and environments grown in multiple pretreated lignocellulosic hydrolysates. Individual strains were inoculated into 96-well plates containing 6 or 9% glucan loading AFEX™ pretreated corn stover (ACS), raw or detoxified alkaline hydrogen peroxide (AHP) pretreated corn stover (CS) or switchgrass (SG), [C2mim][OAc]-pretreated SG, or two different proprietary dilute acid pretreated biomass, including supplementation with yeast extract and peptone (YP). Cell densities were continuously measured for 24-48 hours, from which specific growth rates for each strain in every media condition were calculated and normalized relative to their growth rate in YPD media. Each strain was then ranked from fastest to slowest relative growth rate and hierarchically clustered (FIG. 2A). Individual strain growth ranked similarly in ACSH and AHP SG and CS hydrolysates, which were generated by alkaline-based pretreatments. In contrast, the distinctive growth rank signatures in Ionic Liquid (IL) and dilute acid pretreated lignocellulosic hydrolysates were observed, with most strains unable to grow in dilute acid pretreated LCH #2. Given our interest in understanding the genetic determinants of xylose fermentation from AFEX™-pretreated LCHs, we identified strains that were broadly tolerant to most of the pretreated LCHs with a particular interest in those that ranked highest in growth rate in alkaline pretreatments. One strain that fit this description, NRRL YB-210 (YB-210) and previously named GLBRCY0, was found to grow robustly in AFEX™, AHP, and dilute acid pretreated hydrolysates, and to a slightly lesser extent in IL pretreated hydrolysate (FIGS. 2B-C). Furthermore, we independently determined that YB-210 display tolerance to ethanol stress (D. J. Wohlbach, J. A. Lewis and A. P. Gasch, unpublished observations), elevated temperature (Jin et al., Biotech for Biofuels (2013)) and inhibitors found in AHP pretreated LCHs (Sato et al., Applied Environ. Microbiol. 80:540 (2014)). Therefore, the YB-210 strain background was selected for metabolic engineering and evolution of anaerobic xylose fermentation.

TABLE 1

S. cerevisiae Strains

| Strain name | Genotype | Reference |
|---|---|---|
| GLBRCY22-3 | NRRL YB-210 MATa spore HOΔ::ScTAL1-CpxylA-SsXYL3-loxP-KanMX-loxP | Parreiras et al., PloS one 9(9):e107499 (2014). |
| GLBRCY127 | GLBRCY22-3 MATa, aerobically evolved isolate on YPDX | Parreiras et al. (2014) |
| GLBRCY128 | GLBRCY127 MATa, anaerobically evolved isolate on YPDX | Parreiras et al. (2014) |

TABLE 1-continued

S. cerevisiae Strains

| Strain name | Genotype | Reference |
|---|---|---|
| GLBRCY36 | GLBRCY22-3 with loxP-KanMX-loxP marker excised by Cre | Parreiras et al. (2014) |
| GLBRCY132 | GLBRCY127 with loxP-KanMX-loxP marker excised by Cre | Parreiras et al. (2014) |
| GLBRCY133 | GLBRCY128 with loxP-KanMX-loxP marker excised by Cre | Parreiras et al. (2014) |
| GLBRCY156 | GLBRCY127 MATα | This study |
| GLBRCY310 | GLBRCY36 hog1Δ::KanMX | This study |
| GLBRCY235 | GLBRCY36 isu1Δ::loxP | This study |
| GLBRCY263 | GLBRCY36 isu1Δ::loxP hog1Δ::KanMX | This study |
| GLBRCY174 | BY4741 HOΔ::ScTAL1-CpxylA-SsXYL3-loxP | This study |
| GLBCY176 | CEN.PK113-5D HOΔ::ScTAL1-CpxylA-SsXYL3-loxP | This study |
| GLBRCY319 | GLBRCY174 hog1Δ::KanMX | This study |
| GLBRCY187 | GLBRCY174 isu1Δ::loxP-HygMX-loxP | This study |
| GLBRCY274 | GLBRCY174 hog1Δ::KanMX isu1Δ::loxP-HygMX-loxP | This study |
| GLBRCY271 | GLBRCY176 hog1Δ::KanMX | This study |
| GLBRCY188 | GLBRCY176 isu1Δ::loxP-HygMX-loxP | This study |
| GLBRCY272 | GLBRCY176 hog1Δ::KanMX isu1Δ::loxP-HygMX-loxP | This study |
| GLBRCY276 | GLBRCY174 isu1Δ::loxP hog1Δ::KanMX gre3Δ::loxP ira2Δ::loxP | This study |
| GLBRCY278 | GLBRCY176 isu1Δ::loxP hog1Δ::KanMX gre3Δ::loxP ira2Δ::loxP | This study |
| GLBRCY302 | GLBRCY36 isu1Δ::loxP-HygMX-loxP hog1Δ::KanMX gre3Δ::loxP | This study |
| GLBRCY283 | GLBRCY36 isu1Δ::loxP hog1Δ::KanMX ira2Δ::loxP-HygMX-loxP | This study |
| GLBRCY286 | GLBRCY36 isu1Δ::loxP hog1Δ::KanMX gre3Δ::loxP ira2Δ::loxP | This study |
| GLBRCY132 xylAΔ | GLBRCY132 xylAΔ::loxP-KanMX-loxP | Parreiras et al. (2014) |
| GLBRCY132 tal1Δ | GLBRCY132 synthetic tal1Δ::loxP-KanMX- loxP | Parreras et al. (2014) |
| GLBRCY133 xylAΔ-A | GLBRCY133 xylAΔ::loxP-KanMX-loxP transformant A | Parreiras et al. (2014) |
| GLBRCY133 xylAΔ-B | GLBRCY133 xylAΔ::loxP-KanMX-loxP transformant B | Parreiras et al. (2014) |
| GLBRCY36 gre3Δ | GLBRCY36 gre3Δ::loxP-KanMX-loxP | Parreiras et al. (2014) |
| GLBRCY132 gre3Δ | GLBRCY132 gre3Δ::loxP-KanMX-loxP | Parreiras et al. (2014) |
| GLBRCY133 gre3Δ | GLBRCY132 gre3Δ::loxP-KanMX-loxP | Parreiras et al. (2014) |

Figure 8C:
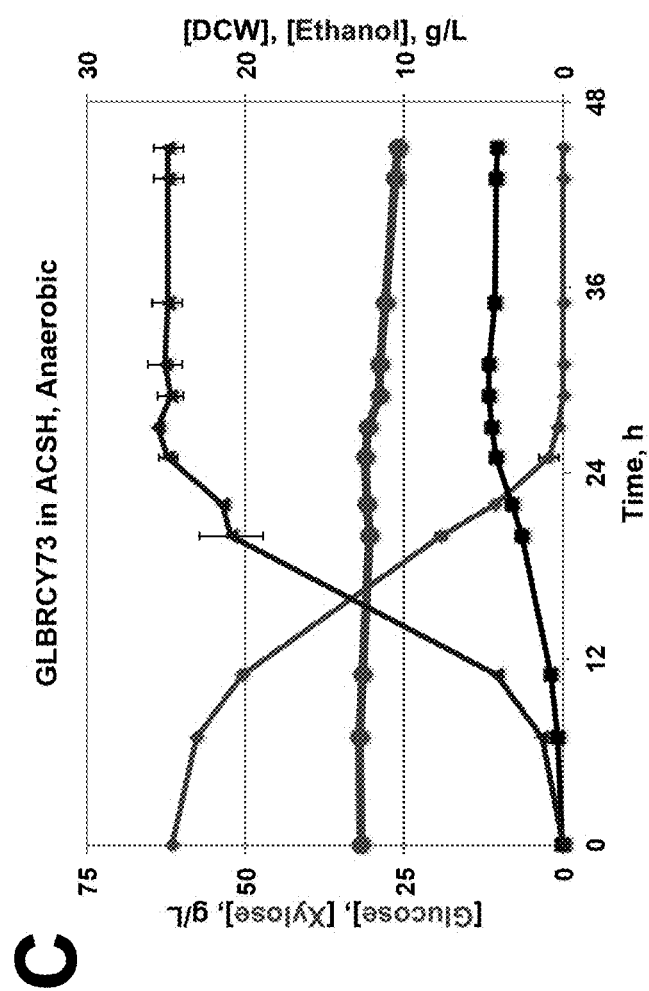
FIG. 8 demonstrates that a hydrolysate-tolerant YB-210/GLBRCY0 engineered with XR/XDH and evolved for aerobic xylose metabolism cannot ferment xylose anaerobically. The YB-210/Y0 strain engineered with XYL1, 2 and 3 genes from *S. stipitis* and aerobically-evolved (GLBRCY73) was cultured in bioreactors and evaluated for consumption of xylose in aerobic YPXD (FIG. 8A), anaerobic YPXD (FIG. 8B), and anaerobic ACSH (FIG. 8C) media as described in Materials and Methods (see Examples). Results displayed are from two independent biological replicates. Concentrations (g/L) of glucose (green circle), xylose (red circle), dry cell weight (black square), and ethanol (blue triangle) measured from representative experiments performed in duplicate are indicated.

After preliminary observations revealed the stress tolerant properties of the YB-210/Y0 strain, we first opted to engineer the strain for xylose metabolism by inserting an expression cassette containing the XYLJ (xylose reductase, XR), XYL2 (xylitol dehydrogenase, XDH), and XYL3 (xylulokinase) genes from *Scheffersomyces stipitis*. Wohlbach et al., *PNAS USA* 108:13212 (2011). While stable genomic insertion of these genes into the YB-210 background conferred detectable consumption of xylose in lab media (Wohlbach et al., *PNAS USA* 108:13212 (2011)), the engineered strain (named GLBRCY2A or Y2A) displayed severe reductions in xylose consumption rates when fermenting AHP CS hydrolysate (AHP CSH) (Sato et al., *Applied Environ. Microbiol.* 80:540 (2014)). To improve xylose metabolism, the Y2A strain was subjected to aerobic batch adaptation on xylose, from which a single clone was isolated (GLBRCY73; Y73) having improved xylose consumption rates in both lab media (FIG. 8A) and AHP SG hydrolysate (AHP SGH). See also Sato et al., *Applied Environ. Microbiol.* 80:540 (2014). We further examined the ability of Y73 to ferment xylose under controlled anaerobic conditions in $N_2$-sparged bioreactors containing YP, 6% glucose and 3% xylose (YPXD) in lab media (FIG. 8B) or ACSH (FIG. 8C). While the Y73 strain could aerobically consume approximately 50% of the xylose in approximately 48 hours, it fermented <20% and <5% of the total xylose anaerobically from YPXD and ACSH, respectively, within the same time period. These results indicated that the Y73 strain was severely impaired for anaerobic fermentation of xylose, particularly in ACSH, relative to aerobic culturing and suggest that this strain would not be useful in our goals to better understand anaerobic xylose fermentation. Attempts to further improve the Y73 by anaerobic adaption on xylose did not yield any improved clones.

Similar to what we observed with the GLBRCY73 strain, others have reported reduced anaerobic xylose consumption rates from *S. cerevisiae* strains also expressing *S. stipitis* XR-XDH enzymes. This limitation is likely due to redox cofactor imbalance; heterologous engineering of *S. stipitis* XYL1, which primarily utilizes NADPH as its reducing cofactor, and XYL2, which uses NAD as its oxidizing cofactor, introduces incomplete cycles in *S. cerevisiae* that are rapidly imbalanced in the absence of oxygen (Jeffries et al., *Applied Microbiol. Biotechnol.* 63:495 (2004)). To circumvent this problem, alternative XRs and XDHs, either from other species (Krahulec et al., *Biotechnology J.* 4:684 (2009)) or through mutagenesis (Bengtsson et al., *Biotechnol. Biofuels* 2:9 (2009); Matsushika et al., *Applied Microbiol. Biotechnol.* 81:243 (2008)), that utilize NADH and NADP respectively, or xylose isomerase (Brat et al., *Applied Environmental Microbiol.* 75:2304 (2004); Karhumaa et al., *Yeast* 22:359 (2005); Kuyper et al., *FEMS Yeast Research* 4:655 (2004)), which catalyzes the conversion of xylose into xylulose without cofactors, have been engineered into *S.* cerevisiae. In an alternative approach, we re-engineered the diploid NRRL YB-210 strain with an expression cassette containing *Clostridium phytofermentans* xylose isomerase (CphytoXylA), which can confer anaerobic xylose fermentation by *S. cerevisiae* with additional genetic modifications (Brat et al., *Applied Environ. Microbiol.* 81:243 (2009)), driven by the ScerTDH3 promoter. In addition, the cassette included ScerTAL1, a Pentose Phosphate Pathway transaldolase enzyme that can improve xylose metabolism when overexpressed (Ni et al., *Applied Environmental Microbiol.* 73:2061 (2007); Walfridsson et al., *Applied Environmental Microbiol.* 61:4184 (1995)) and SstipXYL3 driven by the ScerPGK1 and ScerTEF2 promoters, respectively. Finally, in order to simplify future genomic resequencing of evolved descendants, as well as rapidly uncover beneficial recessive traits during directed evolution, we sporulated and dissected tetrads of the engineered diploid strain, and isolated one haploid spore, named GLBRCY22-3 (Y22-3), that maintained the TAL1-XylA-XYL3 gene expression cassette.

To assess whether the engineered Y22-3 strain could metabolize xylose, we aerobically cultured the strain in YPXD media and monitored extracellular glucose, xylose, and dry cell weight concentrations (FIG. 3A). The Y22-3 strain consumed less than half of the xylose within 64 hours, which was significantly less than the Y73 strain. Thus, the Y22-3 strain was subjected to aerobic batch selection in YP media containing 0.1% glucose and 2% xylose and without exogenous mutagens. For the first seven transfers, which took place over 3-4 day periods, the culture grew at rates of ~1 generation per day with limited xylose depletion detected in the media (FIG. 3B), suggesting that most of the growth was from glucose. Over the eighth to eleventh transfer, slightly greater xylose consumption was observed, however this did not result in substantially faster cell growth rates. By the twelfth transfer and beyond, the culture adapted to xylose, consuming all of the sugar within the 2-4 day passaging cycle and reaching saturated growth. After the 34th transfer, the culture was plated and single clones were screened for growth on xylose. One clone, named GLBRCY127 (Y127), displayed rapid aerobic growth in YPX by 96-well plate assay and was evaluated for aerobic xylose consumption in culture tubes containing YPX media (FIG. 3C) or bioreactors containing YPXD media (FIG. 3D). Consistent with the growth phenotype in 96-well plates, the Y127 strain displayed faster xylose consumption rates than the parental Y22-3 strain (FIGS. 3A, C, D; Table 1). These results indicate that the Y127 isolate evolved from Y22-3 with properties allowing faster aerobic xylose consumption.

We next assessed the ability of the Y127 strain to anaerobically ferment xylose in bioreactors sparged with nitrogen. Similar to that for the XR-XDH engineered Y73 strain (FIG. 8B), the aerobically evolved Y127 strain displayed limited xylose fermentation from YPXD media, consuming less than 30% of the total xylose within 42 hours and did not appear to convert any xylose into ethanol (FIG. 4A). This suggested that, like Y73, the Y127 strain was not capable of effectively fermenting xylose in the absence of oxygen. In an attempt to overcome this barrier, we performed a second round of batch selection of the Y127 strain cultured in YP media containing 0.1% glucose and 2% xylose under completely anaerobic conditions (FIG. 4B). During the first two transfers, 40 μg/L ergosterol and 4 g/L Tween-80 were added to support anaerobic growth, but then omitted for all proceeding transfers. For the first six transfers, the cell population doubled approximately twice per week. After the sixth transfer, the culture began to grow faster and consume a greater percentage of the total xylose per day. After reaching 33 generations at the 10th transfer, the culture appeared to plateau in anaerobic growth and xylose consumption rate. After the 14th transfer, the culture was plated and colonies screened for fastest growth rate in YPX media by 96-well plate assay. One clone (GLBRCY128) displaying rapid anaerobic growth on xylose was then evaluated in bioreactors containing YPXD media sparged with nitrogen (FIG. 4C). In contrast to GLBRCY127 (FIG. 4A), the GLBRCY128 strain fermented xylose rapidly in the absence of oxygen and glucose, during which time the extracellular ethanol concentration increased. Indeed, the GLBRCY128 strain exhibited higher absolute and specific xylose consumption rates in anaerobic YPXD media than the Y127 strain (Table 2). These results indicate that the two-stage directed evolution yielded Y127 and Y128 strains with faster growth from enhanced aerobic and anaerobic xylose metabolism, respectively.

Within a relatively small number of generations without exogenous mutagens, our two-stage evolution yielded a XylA-engineered *S. cerevisiae* strain with the ability to anaerobically consume xylose from lab media (see FIG. 5A). Although the Y128 genetic background originated from a wild hydrolysate-tolerant strain, Y128 could have lost stress tolerant traits during the course of xylose evolution. In such case, Y128 may not be able to anaerobically convert of xylose from pretreated lignocellulose into ethanol, which was our stated goal of this work. Previous studies have shown that yeast strains that can ferment xylose rapidly in lab media are severely impaired in pretreated LCHs. Jin et al., *Biotech. for Biofuels* (2013). Therefore, we assessed the abilities of the Y127 and Y128 strains to anaerobically ferment sugars from ACSH in bioreactors sparged with nitrogen. Similar to what was observed in YP lab media, both Y127 and Y128 strains fermented glucose rapidly. However, only the Y128 strain appeared to consume most of the xylose (approximately 50% of the xylose within approximately 44 hours) once glucose was depleted from the ACSH. Indeed the absolute and specific xylose consumption rates for Y128 were approximately 10-fold higher than Y127 (Table 2). Because Y128 ferments more xylose than Y127 anaerobically, this resulted in a higher ethanol titer for Y128 (FIGS. 5B, C). Thus, despite the evolution on xylose occurred with lab media that lacks the inhibitors found in pretreated hydrolysates, the Y128 strain could effectively ferment xylose from a model industrial pretreated hydrolysate in the absence of oxygen.

TABLE 2

Xylose Consumption Rates and Product Yields for Bioreactor Fermentation in Lab Medium and ACSH

| | Aerobic YPXD | | | Anaerobic YPDX | | | Anaerobic ACSH | | |
|---|---|---|---|---|---|---|---|---|---|
| | Y73 | Y22-3 | Y127 | Y73 | Y127 | Y128 | Y73 | Y127 | Y128 |
| Absolute xylose consumption rate (grams xylose consumed/L/hr) | 0.47 ± 0.02 | 0.170 ± 0.003 | 0.310 ± 0.01 | 0.30 ± 0.02 | 0.094 ± 0.031 | 1.68 ± 0.06 | 0.28 ± 0.01 | 0.04 ± 0.03 | 0.52 ± 0.01 |

TABLE 2-continued

Xylose Consumption Rates and Product Yields for Bioreactor Fermentation in Lab Medium and ACSH

| | Aerobic YPXD | | | Anaerobic YPDX | | | Anaerobic ACSH | | |
|---|---|---|---|---|---|---|---|---|---|
| | Y73 | Y22-3 | Y127 | Y73 | Y127 | Y128 | Y73 | Y127 | Y128 |
| Specific xylose consumption rate (grams xylose consumed/d/h/g DCW) | 0.039 ± 0.001 | 0.019 ± 0.000 | 0.036 ± 0.01 | 0.066 ± 0.010 | 0.0165 ± 0.007 | 0.27 ± 0.06 | 0.059 ± 0.01 | 0.013 ± 0.01 | 0.18 ± 0.02 |
| % of theoretical yield for consumed sugars | ND | ND | ND | 80.1 ± 1.4 | 86.0 ± 2.5 | 87.5 ± 1.1 | 72.1 ± 10.4 | 78.9 ± 14.3 | 77.2 ± 6.4 |
| $Y_{x/glc}$ | ND | ND | ND | 0.079 ± 0.000 | 0.093 ± 0.001 | 0.11 ± 0.02 | 0.066 ± 0.012 | 0.045 ± 0.004 | 0.05 ± 0.01 |
| $Y_{gly/glc}$ | ND | ND | ND | 0.101 ± 0.001 | 0.068 ± 0.002 | 0.076 ± 0.007 | 0.051 ± 0.002 | 0.038 ± 0.006 | 0.04 ± 0.00 |

ND = no data available

Example 2—Assessing Xylose Consumption by GLBRCY127 and Y128

After clearly establishing the xylose consumption phenotypes of the Y127 and Y128 strains, we next wanted to better understand the potential genetic mechanisms by which these strains could have evolved. One possibility would be through mutations in the engineered genes XylA, TAL1, and XKS1 that increase their expression or activities. However, when the engineered gene cassette was sequenced, no DNA sequence differences were identified. An alternative possibility is that the Y127 or Y128 strains obtained gain-of-function mutations in native genes that code for xylose metabolism enzymes, which are normally expressed at low levels or lack sufficient activities rapid flux into the pentose phosphate pathway (Jeffries et al., *Applied microbiol. and biotechnol.* 63:495 (2004)). The *S. cerevisiae* genome contains a number of putative enzymes with xylose reductase activities, most notably the aldolase GRE3, which convert xylose into xylitol, and xylitol dehydrogenases, including an ineffective XYL2 homolog and most recently, XDH1, which is present in some wild *S. cerevisiae* strains and is necessary and sufficient for detectable xylose consumption (Wenger et al., *PLoS genetics* 6:e1000942 (2010)). Thus, one possible model for the evolution of Y127 and Y128 is that genetic changes in one or more of these genes allowed for improved xylose consumption independent of XylA and TAL1 We examined this possibility first by deleting XylA from the Y127 genome and assessed its ability to consume xylose aerobically. Indeed, the Y127 xylAΔ strain was completely ablated of its ability consume or produce any cell biomass from xylose (FIG. 6A). In contrast, deletion of TAL1 from Y127 reduced the rate of xylose metabolism (FIG. 6B), suggesting that the additional copy of TAL1 was important for determining the rate of xylose consumption but was not absolutely essential. In addition, we identified two independent Y128 xylAΔ candidates that were verified by PCR. Consistent with the Y127 xylAΔ strain, the Y128 xylaΔ-B strain could consume xylose aerobically (data not shown) or anaerobically (FIG. 6C). Interestingly, the Y128 xylaΔ-A strain fermented xylose at a rate comparable rate to that of the Y128 strain. This suggested the possibility that the XylA gene was duplicated in cis, which could account for why the replacement of XylA with the KanMX deletion cassette verified by PCR. Indeed, when we compared XylA RNA expression in the two Y128 xylAΔ strains with the Y128 strain by quantitative PCR (qPCR), we observed that the Y128 xylaΔ-A cells express half as much XylA as Y128, while no XylA RNA was detected in the Y128 xylaΔ-B strain (FIG. 6D). While this does not rule out the possibility of genetic changes in an endogenous xylose metabolizing enzyme, these results together suggest that the evolved xylose consumption phenotypes in Y127 and Y128 are dependent upon the engineered XylA and TAL1 genes.

The data presented thus far implicates the Y128 strain with an evolved ability to ferment xylose anaerobically in lab media (FIGS. 3C, D) and ACSH (FIG. 5C). As additional means to better understand how the evolved strains anaerobically ferment xylose, we analyzed the intracellular concentrations of metabolic intermediates of xylose catabolism. During the anaerobic fermentation of ACSH by the Y127 and Y128 strains (FIGS. 5A, C), culture samples were removed from the bioreactors at 5 different time-points spanning the glucose and xylose consumption phases: two samples were taken when glucose was detected in the hydrolysate (depicted by horizontal lines in shades of green), one during the transition to xylose after glucose was undetected (grey horizontal line), and two final samples when xylose consumption (horizontal lines in shades of red) was evident. Samples for Y127 and Y128 fermentations were taken at comparable sugar concentrations, while the last two samples were taken at the equivalent amount of time after the transition time-point. Cells were captured and washed on filters, and then placed in 40% acetonitrile:40% methanol:20% water:0.1% formic acid solvent to stabilize and extract intracellular metabolites. Intracellular concentrations of xylose, xylitol, and xylulose were then quantified using gas chromatography. Xylulose-5-phosphate levels were quantified by reverse phase anion exchange liquid chromatography and electrospray ionization couple with tandem mass spectrometry. Interestingly, the Y128 accumulated higher concentrations of intermediates from the engineered xylose metabolism pathway than Y127 (FIGS. 7A-C). In particular, intracellular xylose, xylulose (the product of xylose isomerase from xylose), and xylulose-5-phosphate, which is generated from phosphorylation of xylulose by Xks1p, levels were higher in Y128 than Y127 at the transition stage and the two time-points during xylose metabolism.

In addition to quantifying intermediates of our engineered xylose metabolism pathway, we also quantified intracellular levels of xylitol. A common phenotype in engineered strains is the production of xylitol, which is then exported out of the cell. Strikingly, we observed a severe reduction in intracellular xylitol levels for Y128 at all time-points, where as Y127 appeared to accumulate xylitol over time (FIG. 7D). Early biochemical work has shown that bacterial xylose isomerase is inhibited by xylitol (Yamanaka, *Archives Biotech. & Biophys.* 131(2):502-506, 1969), and more recent studies on *S. cerevisiae* engineered with xylose isomerase has shown that deletion of GRE3, which encodes an enzyme that can convert xylose into xylitol, can improve xylose fermentation (Traff et al., *Appl. Environ. Microbiol.* 67(12): 5668-5674, 2001). This suggested that one difference between the Y127 and Y128 could be a mutation that alters GRE3 activity or expression. Thus, we sequenced the GRE3 open reading frames of the Y22-3, Y127, and Y128 strains and found a single nucleotide polymorphism (SNP) in the Y128 strain harbored a G to A mutation relative to both Y22-3 and Y127, which changed the alanine at amino acid residue 46 to threonine (A46T). This residue is conserved amongst other *S. cerevisiae* strains, as well as many other yeast species, including *Saccharomyces arboricola* and *kudriavzevii, Candida* and *Kluyveromyces* species, and resides within the aldo-ketoreductase catalytic domain, suggesting that this mutation likely impacts Gre3p activity.

Taken together, our results suggest that the gre3$^{446T}$ mutation in Y128 causes a partial or complete loss of Gre3p function, which in turn reduces inhibition of CphytoXylA by xylitol. For additional confirmation that loss of Gre3p activity improves anaerobic xylose fermentation in our strain background, we deleted GRE3 in the Y22-3, Y127, and Y128 strains and compared their abilities to ferment xylose in the absence of oxygen. Indeed, we found that the Y127 gre3Δ strain could anaerobically consume xylose (FIG. 7E) and grow (FIG. 7F) faster than the parental Y127 strain, but not nearly as fast as Y128. This suggests that the Y128 strain contains mutations other than gre3$^{446T}$ that help in anaerobic xylose fermentation. Consistent with our conclusion that the gre3$^{446T}$ mutation is a loss of function, there were no differences in the xylose consumption or growth rates between the Y128 and Y128 gre3Δ strains. Finally, deletion of GRE3 in the Y22-3 parental strain had no effect, further indicating that loss of GRE3 alone cannot confer anaerobic xylose fermentation, and that mutations acquired by Y127 from aerobic evolution on xylose are important for anaerobic consumption of xylose. Together, these results indicate that the Y128 strain evolved a loss-of-function mutation in GRE3, improving xylose utilization by reducing the production of inhibitory xylitol.

Example 3—Mutations in ISU1, HOG1, GRE3, and IRA2 Co-Segregate With Evolved Phenotypes Our phenotypic analyses of GLBRCY22-3, GLBRCY127, and GLBRCY128 strains indicates that each have differential abilities to metabolize xylose under aerobic and anaerobic conditions (2). Furthermore, metabolite analyses and targeted DNA sequencing further determined that a loss-of-function mutation in GRE3 that emerged during the evolution of Y128 was critical for its ability to ferment xylose anaerobically. However, deletion of GRE3 alone in the Y127 strain could not phenocopy Y128 for xylose fermentation, suggesting that additional mutations were necessary. To better understand the genetic mutations that confer xylose metabolism, we applied a combination of long and short read genome resequencing to identify the evolved mutations in Y127 and Y128. From these approaches, we first assembled and annotated the complete Y22-3 genome sequence. We then utilized the Genome Analysis Toolkit (GATK) to identify single nucleotide polymorphisms (SNPs) and DNA insertions and deletions (indels) found in Y127 and Y128 relative to the Y22-3 reference genome.

From our sequence analyses, we identified three mutations in the evolved Y127 genome sequence that were not present in the Y22-3 parent strain, including missense mutations in ISU1 and GSH1, and a single base pair "A" deletion in HOG1, which resulted in a frame-shift of its coding sequence (Table 3). ISU1 encodes a mitochondrial protein involved in assembling iron-sulfur (Fe—S) clusters (18, 19), which are used as co-factors in recipient proteins for electron transfer, enzymatic reactions, and oxygen sensing. GSH1 encodes γ-glutamylcysteine synthetase that catalyzes the first step in glutathione biosynthesis by converting glutamate into γ-glutamylcysteine (20), while the Hog1p Mitogen-Activated Protein Kinase (MAPK) is a key component of the high osmolarity glycerol (HOG) pathway that regulates responses to hyperosmotic stress (reviewed recently in (21)). Importantly, the genome sequence of Y128, which was evolved from Y127, contained the expected isu1, gsh1 and hog1 mutations, as well as the previously identified missense mutation in GRE3 (2). In addition, Y128 contained an additional nonsense mutation in IRA2, which negatively regulates cAMP-Protein Kinase A signaling (22), and missense mutation in SAP190 (Table 3). The evolved nonsense mutation in IRA2 causes truncation of the carboxy-terminal 152 amino acids, a region previously shown to be important for Ira2p stability (23). All six mutations were independently verified by PCR and Sanger sequencing, indicating that at least three mutations emerged during the aerobic and anaerobic evolution of Y22-3 and Y127 on xylose, respectively.

TABLE 3

Genetic Differences Between Parental and Evolved Strains

| Evolved Strain | Parental Strain | Gene | Functional Gene Annotation[1] | Nucleotide Difference[2] | Amino Acid Difference[3] |
|---|---|---|---|---|---|
| Y127 | Y22-3 | ISU1 | Fe—S cluster assembly | C412T | H138Y |
| Y127 | Y22-3 | HOG1 | MAP kinase signaling | A844del | M282frame-shift[4] |
| Y127 | Y22-3 | GSH1 | Glutathione biosynthesis | G839A | R280H |
| Y128 | Y127 | GRE3 | Aldose reductase | G136A[5] | A46T |
| Y128 | Y127 | IRA2 | Inhibitor of RAS | G8782T | E2928Stop |

TABLE 3-continued

Genetic Differences Between Parental and Evolved Strains

| Evolved Strain | Parental Strain | Gene | Functional Gene Annotation[1] | Nucleotide Difference[2] | Amino Acid Difference[3] |
|---|---|---|---|---|---|
| Y128 | Y127 | SAP190 | Component of Sit4p phosphatase complex | A2590G | S864G |

[1]*Saccharomyces* Genome Database (www.yeastgenome.org/on the World Wide Web).
[2]Nucleotide and position in parent to evolved mutation.
[3]Amino acid and position in parent to evolved amino acid.
[4]Deletion mutation caused a codon shift in the reading frame.
[5]Published in *Parreiras* et al., 2014 (incorporated herein by reference as if set forth in its entirety).

Since mutations occur randomly during DNA replication, mutations with neutral or minimal impact on selective growth (so called "hitchhiker" mutations; (24)) can be carried along with beneficial "driver" mutations during experimental directed evolution. Thus, all six identified mutations may be not important for the evolved phenotypes. To identify the "driver" mutations, we phenotyped and genotyped the haploid progeny derived from backcrosses between the evolved strains and their parental strains (FIG. 9). If the phenotype was driven by a single mutation, the haploid progeny would display a 2:2 segregation in evolved::parental phenotype, and should co-segregate with the genotype (FIG. 9A). If, however, the mutation involves two (FIG. 9B) or more mutations that cause the phenotype, then the phenotypic segregation involves a number of possible combinations. From the Y22-3×Y127 backcross, 40 viable spores derived from 10 tetrad sets were genotyped by PCR and Sanger sequencing. As expected, the hog1, isu1 and gsh1 mutations segregated with 2:2 (mutant:parental sequences) ratio in the resulting haploid progeny. We then assessed the abilities of the genotyped progeny to metabolize xylose under aerobic conditions. The six individual progeny harboring all three mutations metabolized xylose at rates comparable to the evolved Y127 strain, as did one spore containing only hog1 and isu1 mutations (FIGS. 9C-D). The haploid progeny containing the isu1 mutation with (n=4) or without (n=9) the gsh1 mutation consumed xylose at a rate intermediate to the evolved Y127 and parental Y22-3 strains. Interestingly, progeny containing the hog1 mutation along with (n=5) or without (n=7) the gsh1 mutation displayed an inability to metabolize xylose similar to the Y22-3 parent, as did progeny with the gsh1 mutation (n=5) alone. These results suggest that the isu1 mutation is necessary for aerobic xylose metabolism in the Y127 strain, while the hog1 mutation enhances the rate of xylose consumption only in the presence of isu1. The gsh1 mutation may be a hitchhiker, or subtly influence xylose metabolism.

It was next determined which mutations in Y128 were responsible for its ability to ferment xylose anaerobically. As done with Y127, the Y128 strain was backcrossed to the Y127 MAT parental strain (thus, all progeny from this cross maintained the hog1, isu1 and gsh1 mutations) and the resulting 28 haploid progeny from 7 tetrads were genotyped and phenotyped. The ira2, gre3 and sap190 mutations segregated 2:2 mutant::parent in the tetrad progeny (FIG. 9E). We then evaluated each of the haploid descendants for their abilities to consume xylose anaerobically. As expected, strains harboring all three ira2, gre3 and sap190 mutations fermented xylose similarly to that of Y128, as did progeny containing mutant ira2 and gre3, but parental SAP190 (FIGS. 9E-F). Interestingly, descendants with ira2 or gre3 mutations alone displayed intermediate rates of anaerobic xylose consumption. In contrast, there were no differences in xylose fermentation for haploids containing parental or mutant versions of SAP190, suggesting that the gre3 and ira2 mutations are the major drivers in the Y128 phenotype, while sap190Δ is a hitchhiker mutation.

We next sought to determine whether the deletion of the evolved gene targets were sufficient to recapitulate the ability to aerobically metabolize xylose. The isu1$^{H138Y}$ mutation results in a histidine-to-tyrosine substitution at a position adjacent to a conserved PVK domain, which binds to HSP70 Ssq1p for assembly of Fe—S clusters (25). The hog1 frame-shift mutation was predicted to alter 123 of the 435 total amino acids in Hog1p. Thus, we surmised that these mutations significantly reduce Isu1p and Hog1p functions, and hypothesized that null mutations in ISU1 and HOG1 would phenocopy the evolved mutations. We tested this hypothesis by deleting HOG1 and ISU1 individually or in combination from the Y22-3 parent strain lacking the KanMX resistance marker (GLBRCY36) and assessed the resulting mutant strains for the ability to metabolize xylose aerobically. Consistent with spores harboring only the hog1 evolved frame-shift mutation, the Y36 hog1Δ mutant did not metabolize significant amounts of xylose, akin to the parental Y36 strain (FIG. 10A). In contrast, the Y36 hog1Δ isu1Δ double mutant metabolized xylose at a rate equivalent to the Y127 marker-rescued strain (GLBRCY132), while the Y36 isu1Δ strain metabolized xylose at a slightly slower rate.

We further assessed the sufficiency for deletion of HOG1 and ISU1 in aerobic xylose metabolism by examining the effect of these mutations in distinct *S. cerevisiae* strain backgrounds. First, we engineered the identical DNA cassette as Y22-3 for the expression of bacterial xylose isomerase, fungal XYL3 and yeast TAL1 (2) into the lab strains BY4741 (renamed GLBRCY174), which was derived from S288c (3), and CEN.PK113-5D (4) (renamed GLBRCY176), and then HOG1 or ISU1 were deleted from their genomes. As shown in FIG. 10, aerobic xylose consumption assays revealed that both Y174 and Y176 hog1Δ isu1Δ double mutants consumed xylose significantly faster than the Y174 and Y176 parental strains. However, both double mutant strains did not consume xylose at rates comparable to Y132 or the Y36 hog1Δ isu1Δ mutant, and the isu1Δ single mutants did not metabolize significant amounts of xylose. While these results indicate that the effectiveness of these mutations on xylose metabolism have some dependence upon strain background, they support the notion that epistatic interactions between HOG1 and ISU1 negatively regulate xylose metabolism and that deletion of both genes are sufficient to confer aerobic xylose consumption.

Previously, we determined that deletion of GRE3 was sufficient for increasing the rate of xylose fermentation in the antibiotic resistance marker-rescued Y127 strain (referred to herein as GLBRCY133) (2). See FIGS. 7E-F. However, the Y132 gre3Δ strain did not phenocopy the anaerobic xylose consumption trait of Y133, prompting us to conclude that at least one additional mutation was needed. Therefore, we generated and compared Y132 ira2Δ and Y132 gre3Δ ira2Δ mutant strains for their abilities ferment xylose anaerobically. Similar to what was observed in our backcross studies, the Y132 ira2Δ strain displayed an intermediate rate of anaerobic xylose consumption (FIG. 11A), while the Y132 gre3Δ ira2Δ double mutant phenocopied Y133 for xylose consumption rate. Moreover, the xylose consumption phenotypes of the Y133 and Y133 gre3Δ ira2Δ strains were nearly identical, further suggesting that the evolved gre3 and ira2 point mutations cause losses in gene function.

Together, our genotypic and phenotypic studies implicate loss-of-function mutations in HOG1, ISU1, GRE3, and IRA2 for enhancing xylose metabolism. As additional evidence, we deleted various combinations of the four genes from the initial Y36 parent strain that lacks the ability metabolize xylose aerobically or anaerobically (see FIG. 11; Table 4). These strains were then assessed for the ability to convert xylose anaerobically into ethanol. Notably, the Y36 hog1Δ isu1Δ gre3Δ ira2Δ quadruple knockout strain consumed xylose and produced ethanol at similar rates to the evolved Y133 strain (FIGS. 11A-B). Interestingly, neither Y36 hog1Δ isu1Δ nor Y36 gre3Δ ira2Δ double mutants (FIGS. 11A-B) consumed significant amounts of xylose anaerobically, suggesting that the aerobically evolved hog1 and isu1 mutations in Y127 were necessary for the evolution of Y128 in anaerobic xylose media. Deletion of all four genes in the Y176 CEN.PK strain background conferred faster rates of anaerobic xylose consumption compared to the unmodified parent strains (FIG. 11C). Taken together, these data provide evidence for epistatic interactions between the hog1, isu1, gre3 and ira2 mutations that confer the rapid anaerobic xylose consumption phenotype by Y133.

Given that the primary goal of this work was to identify genetic modifications in S. cerevisiae that will allow anaerobic consumption of xylose from lignocellulosic biomass, we compared the abilities of the Y36 quadruple deletion strain with the evolved Y133 strain to convert xylose from AFEX-pretreated corn stover hydrolysate (ACSH) in the absence of oxygen (FIG. 11A). Under anaerobic conditions, strains containing deletion mutations in HOG1 and ISU1, or GRE3 and IRA2, did not consume significant amounts of xylose. In contrast, the Y36 hog1Δ isu1Δgre3Δ ira2Δ strain displayed consumed xylose at a faster rate than the double mutants, albeit not as fast as the Y133 mutant strain. These results indicate that deletion of HOG1, ISU1, GRE3 and IRA2 together permits anaerobic xylose fermentation in an industrially relevant lignocellulosic hydrolysate.

Further assays revealed that deletion of either ira1 or ira2 can confer capacity for anaerobic xylose fermentation to recombinant yeast having the null mutation. Strains harboring various null mutations in GRE3, IRA2, along with SAP190 (FIGS. 12A-B) or IRA1 (FIGS. 12C-D) within the Y132 or Y133 strain backgrounds were phenotyped by anaerobic xylose metabolism in YPX media.

Further assays revealed that deletion of either ira1 or ira2 can confer capacity for anaerobic xylose fermentation to recombinant yeast having the null mutation. Strains harboring various null mutations in GRE3, IRA2, along with SAP190 (FIGS. 12A-B) or IRA1 (FIGS. 12C-D) within the Y132 or Y133 strain backgrounds were phenotyped by anaerobic xylose metabolism in YPX media. These results demonstrate that deletion of SAP190 does not impact anaerobic consumption of xylose, and that deletion of IRA1 confers moderate, but significant, improvement in anaerobic xylose fermentation.

TABLE 4

Kinetic characteristics of engineered and evolved S. cerevisiae strains in YPX Media

| Condition | Aerobic | | Anaerobic | | | |
|---|---|---|---|---|---|---|
| Strain | $\mu^1$ | $q_{Xyl}^2$ | $\mu^1$ | $q_{Xyl}^2$ | $q_{EtOH}^3$ | $y_{EtOH}^4$ |
| Y36 | NG | 0.015 ± 0.003 | NG | 0.002 ± 0.002 | 0.003 ± 0.001 | ND* |
| Y132 | 0.23 ± 0.08 | 0.268 ± 0.035 | 0.025 ± 0.002 | 0.152 ± 0.041 | 0.060 ± 0.014 | 0.41 ± 0.02 |
| Y133 | 0.25 ± 0.13 | 0.368 ± 0.036 | 0.060 ± 0.002 | 0.419 ± 0.008 | 0.177 ± 0.011 | 0.43 ± 0.01 |
| Y36 hog1Δ | 0.03 ± 0.01 | 0.014 ± 0.008 | ND | ND | ND | ND |
| Y36 isu1Δ | 0.22 ± 0.04 | 0.189 ± 0.083 | ND | ND | ND | ND |
| Y36 hog1Δ isu1Δ | 0.27 ± 0.12 | 0.348 ± 0.048 | NG | 0.118 ± 0.057 | 0.044 ± 0.014 | 0.42 ± 0.05 |
| Y36 gre3Δ ira2Δ | 0.05 ± 0.01 | 0.035 ± 0.004 | NG | 0.125 ± 0.03 | 0.051 ± 0.009 | 0.49 ± 0.07 |
| Y36 hog1Δ isu1Δ gre3Δ | ND | ND | 0.045 ± 0.006 | 0.249 ± 0.053 | 0.106 ± 0.011 | 0.43 ± 0.02 |
| Y36 hog1Δ isu1Δ ira2Δ | ND | ND | 0.055 ± 0.008 | 0.364 ± 0.014 | 0.159 ± 0.003 | 0.44 ± 0.01 |
| Y36 hog1Δ isu1Δ gre3Δ ira2Δ | 0.29 ± 0.15 | 0.409 ± 0.055 | 0.060 ± 0.007 | 0.417 ± 0.049 | 0.179 ± 0.022 | 0.43 ± 0.01 |

ND, Not Determined for aerobic conditions; ND*, Not Determined—no ethanol produced.
NG, No Growth
[1]Growth rate, $h^{-1}$
[2]Specific Xylose Consumption Rate, g xylose consumed · g $DCW^{-1}$ · $h^{-1}$
[3]Specific Ethanol Productivity Rate, g ethanol produced · g $DCW^{-1}$ · $h^{-1}$
[4]Ethanol Yield, g ethanol produced · g xylose consumed$^{-1}$ (Max. Theoretical Yield = 0.51)

Example 4—Materials and Methods

Culture Media:

Standard undefined yeast lab medium was prepared as previous described (Sherman, *Methods in Enzymology* 350: 3-41 (2002)). Briefly, liquid and plate-based medium contained 10 g/L yeast extract and 20 g/L peptone (YP), and various sugar concentrations (X=20 or 30 g/L xylose, D=20 g/L dextrose, DX=60 g/L glucose and 30 g/L xylose). For bioreactor experiments, this YPDX medium also contained 50 mM potassium phosphate, pH 5.0.

AFEX™ Pretreated Corn Stover Hydrolysate (ACSH) Preparation:

Zea mays (Pioneer hybrid 36H56) corn stover was harvested at Field 570-C Arlington Research Station, University of Wisconsin, in 2008 (for 96-well plate phenotyping) or in 2009 (for fermentation experiments). AFEX™ pretreatment of the corn stover was performed as described previously (Balan et al., Methods Mol. Biol. 581:61 (2009)). AFEX™ pretreated corn stover was hydrolyzed at 6% or 9% glucan loading in a 1.5 L reaction volume in a 3 L Applikon fermenter (Applikon Biotechnology Inc. USA) with Spezyme CP (15 FPU/g glucan loading, DuPont Danisco), Multifect Xylanase (10% of Spezyme CP, DuPont Danisco), and Novovzyme 188 (64 pNPGU/g glucan, Sigma-Aldrich) at 50° C. for 5 days. Tetracycline (40 mg/L) was used to prevent microbial contamination and pH 4.8 was maintained during the hydrolysis process. Biomass was added to the reaction mixture in 4 batches within 4 hours from the start of hydrolysis to facilitate better mixing at 1000 rpm. After 120 hours, the hydrolysis mixture was centrifuged (2500 g for 30 min.) and sterile filtered (0.22 mm pore size; Millipore Stericup). For 6% glucan loading ACSH, the final sugar concentrations were 53.3 g/L glucose and 21.7 g/L xylose. For 9% glucan loading ACSH, the final sugar concentrations were 80 g/L glucose and 36 g/L xylose.

For bioreactor fermentations, ACSH was prepared by hydrolysis of corn stover harvested in 2009 in a 14 L bioreactor from Applikon (Applikon Biotechnology), with 12 L loading volume. Nano-pure water was added into the vessel and was autoclaved for 30 min. After vessel was cooled to 70-80° C., 30 ml undiluted HCl was added. After HCl was mixed with water, AFEX-pretreated corn stover was loaded into the vessel to 6% glucan loading. After cooling to 50° C., CTec2 and HTec2 enzymes (Novozymes) were added, with final concentrations of 24 mg/g glucan and 6 mg/g glucan respectively. After hydrolysis for 5 days at 50° C., solids were removed by centrifugation at 8,200 g for 10-12 hours at 4° C., and the supernatant was filter sterilized through 0.5 μm and then 0.2 μm filters prior to storage at 4° C. Prior to fermentation, the hydrolysate was adjusted to pH 5.0 and again filtered through a 0.2 μm filter to remove precipitates and to ensure sterility.

Alkaline Hydrogen Peroxide Pretreated Hydrolysates:

Pioneer hybrid 36H56 corn stover described above and switchgrass (Panicum virgatum cv. Cave-In-Rock) described elsewhere (Li et al., Biotechnol. Biofuels 5:38 (2012)) were milled (Circ-U-Flow model 18-7-300, Schutte-Buffalo Hammermill, LLC) to pass a 5 mm screen. AHP pretreatment was performed as reported previously (Banerjee et al., Biotechnology and Bioengineering 109:22 (2012)) at a hydrogen peroxide loading of 0.125 g $H_2O_2$/g biomass in an incubator with shaking at 150 rpm at 30° C. for 24 hours with periodic pH readjustment to 11.5 during pretreatment using 5 M NaOH. For switchgrass, pretreatment was conducted at biomass concentration of 20% w/w. For corn stover, pretreatment was conducted at biomass concentration of 15% w/w. Following pretreatment, the whole slurry was adjusted to pH 4.8 using 72% $H_2SO_4$. Accelerase 1000 (Novozymes A/S), Multifect xylanase, and Multifect pectinase (DuPont Danisco) were used at the protein ratio of 0.62:0.24:0.14 at a total protein loading was 30 mg/g glucan as assayed by the Bradford Assay. Hydrolysis was performed at 50° C. with shaking speed of 180 rpm for 24 hours. After enzymatic hydrolysis, the whole slurry was centrifuged at 18,000 g for 30 minutes. The supernatant was used as undetoxified raw hydrolysate or F hydrolysate. Activated carbon (Fisher Scientific #05-690A) was mixed with undetoxified hydrolysate at 5% concentration (5 g activated carbon with 100 mL hydrolysate) and incubated at 50° C. for 1 hour in an unbaffled shake flask at 150 rpm. After centrifugation at 18000 g for 30 min, the supernatant was used as the detoxified hydrolysate. Alt hydrolysates were filter-sterilized (0.22 mm pore size; Millipore Stericup). Final sugar concentrations for AHP hydrolysates were 29.7 g/L glucose and 19.8 g/L xylose for raw AHP corn stover hydrolysate, 34.8 g/L glucose and 23.4 g/L xylose for detoxified AHP CSH, and 26.7 g/L glucose and 19.2 g/L xylose for both raw and detoxified AHP SGH.

Dilute Acid Pretreated Lignocellulosic Hydrolysates:

Two different dilute acid pretreated wheat straw hydrolysates were acquired from an industrial collaborator. Both hydrolysates were diluted 4:5 in sterile water supplemented with yeast peptone media (YP).

Ionic Liquid Pretreated Switchgrass Hydrolysate (IL-SGH):

Switchgrass was pretreated with [C2mim][OAc] (1-ethyl-3-methylimidazolium acetate) at 15% solids loading as described elsewhere (Li et al., Biotechol. Biofuels 6:154 (2013)). IL-pretreated switchgrass was hydrolyzed with CTec2 (54 mg/g glucan) and HTec2 (6 mg/g glucan) enzymes (Novozyme) for 72 hours in a 2 L IKA bioreactor. [C2mim][OAc]-pretreated SGH was generated at Advanced Biofuels Process Demonstration Unit (batch ABPDU 110201S02). Final sugar concentrations in the IL-SGH were 41.4 g/L glucose and 9.7 g/L xylose.

Lab Media:

Standard undefined yeast lab media was used as previous described. Briefly, liquid and plate-based media contained 10 g/L yeast extract and 20 g/L peptone (YP), and various sugar concentrations (X=20 g/L xylose, D=20 g/L dextrose or glucose, XD=30 g/L xylose and 60 g/L glucose). Where indicated, hydrolysates were supplemented with 10 g/L yeast extract and 20 g/L peptone. For bioreactor experiments, this YPXD media also contained 50 mM potassium phosphate, pH 5.0.

Saccharomyces cerevisiae Strains:

Yeast strains used in this study are described in Table 1. Generation of Y22-3, Y127, and Y128 strains is described elsewhere (2). The Y174 and Y176 strains were constructed in an identical manner to Y22-3 by integrating the ScTAL1-CpxylA-SsXYL3-loxP-KanMX-loxP cassette into the HO locus of BY4741 (3) and CEN.PK113-5D (4), respectively, followed by excision of the KanMX marker by Cre recombinase (5). The Y127 MATα strain (GLBRCY156) was generated by diploidization of Y127, sporulation, tetrad dissection and mating type identification (1). For backcrossing, Y22-3 or Y128 was mated to Y156, subjected to sporulation and tetrad dissection. All tetrad spores were verified for 2:2 segregation of mating type. Deletion of GRE3, ISU1, and IRA2 were performed by integration of PCR product generated from loxP-KanMX-loxP or loxP-HygMX-loxP templates (5) and primers containing at least 40 by of homology flanking the targeted gene. For deletion of HOG1, gDNA from a hog1Δ::KanMX mutant strain (6) was used as the PCR template. PCR products were purified and transformed (7) into the appropriate strains. Cre recombinase-mediated excision of loxP-flanked antibiotic markers was carried out by as published elsewhere (5) for strains listed in Table 1 containing deletion mutations without an associated antibiotic resistance marker. Sanger sequencing of PCR products and DNA plasmids was performed by the University of Wisconsin-Madison Biotechnology Center.

96-Well Growth Assays and Hierarchical Clustering:

Native *S. cerevisiae* strains used in this study (see Table 1) were obtained from Dr. Cletus Kurtzmann (USDA ARS, Peoria, Ill.), National Collection of Yeast Cultures (Norwich, UK), and Dr. Justin Fay (Washington University, Saint Louis, Mo.). Aerobic growth assays in microtiter plates were performed as previously described (Wolbach et al., *PNAS* 108:13212 (2011); Sato et al., *Applied and Environmental Microbiol.* 80:540 (2014); Jin et al., *Biotechnol. Biofuels* 6:108 (2013)), with one exception: 10 µL of saturated culture was inoculated into 190 µL of YPD or a single type of pretreated lignocellulosic hydrolysate. Cell growth was measured by optical density at 595 nm every 10 minutes for 24 hours in Tecan F500 or M1000 multimode plate readers with an interior temperature of 30° C. Background subtracted cell density readings for each strain were analyzed by GCAT (Sato et al., *Applied and Environmental Microbiol.* 80:540 (2014)). Normalized specific growth rates for each strain from three independent biological replicates in pretreated hydrolysates normalized to their average growth rate in YPD alone, and then ranked ordered from 1 to 117 (including control strains—Y389, BY4741, CEN.PK113-5D and CEN.PK2-1D in duplicate) for highest average specific growth to lowest, respectively. For all strains with no detectable specific growth rates, strains were assigned a rank of 117. Strain ranks in each media condition were hierarchically clustered and displayed with Spotfire (TIBCO).

Long-Read Sequencing of GLBRCY22-3 Genomic DNA:

Sequencing was performed by the Medical College of Wisconsin Human and Molecular Genetics Center (Milwaukee, Wis.). Initial quantification was performed using a Quant-iT™ PicoGreen® dsDNA Assay Kit (Life Technologies, Carlsbad, Calif., USA) and a NanoDrop 2000 (Thermo Fisher Scientific Inc., Waltham, Mass., USA). Genomic DNA (gDNA) was purified and concentrated with a 0.45× AMPure PB bead wash (Pacific Biosciences, Menlo Park, Calif., USA). About 5 µg of concentrated gDNA was sheared to 10 kbase pairs using the Covaris gTube (Covaris Inc, Woburn, Mass., USA). A PacBio sequencing library, or SMRTbell™, was constructed using the SMRTbell™ Template Prep Kit 1.0 and the 10 kb Template Preparation and Sequencing with Low-Input DNA procedure (Pacific Biosciences). P4 Polymerase was coupled with the resulting SMRTbell™ library. For sequencing, the library was bound to Magbeads by incubating for 1 hour at 4° C. This was run over 8 V2 SMRT cells on the PacBio RSII using a C2 chemistry sequencing kit (Pacific Biosciences). Each SMRT cell was visualized using a 1×180 minute movie. Illumina short read sequencing was performed by the University of Wisconsin-Madison Biotechnology Center (8). In brief, libraries derived from purified gDNA were sequenced with 100 by paired end reads using an Illumina HiSeq 2000.

DNA Constructs and Strain Engineering:

Construction of the GLBRCY73 strain has been described elsewhere (Wolbach et al., *PNAS* 108:13212 (2011)). The expression cassette containing *S. cerevisiae* TAL1, *C. phytofermentans* XylA, and *S. stipitis* was generated in similar manner with some modifications. Codon-optimized versions of each gene were synthesized (GeneArt, Life Technologies) and inserted via recombination in the following promoter-open reading frame-terminator combinations: ScPGK1 promoter-ScTAL1-ScTDH3 terminator, ScTDH3 promoter-CpXYLA-ScTEF2 terminator, ScTEF2 promoter-SsXYL3-ScCYC1 terminator. This cassette, which also contains a LoxP-KanMX-LoxP selection marker (Guldener et al., *Nucleic Acids Res.* 24:2519 (1996)) was flanked by ScHO sequences (Voth et al., *Nucleic Acids Res.* 29:E59 (2001)) for targeted recombination at the genomic HO locus. The complete XI cassette was amplified by standard polymerase chain reaction (PCR) using primers that anneal to the 5' ends of the HO flanking sequences, gel purified and transformed into the NRRL YB-210 strain. Following selection on YPD plates containing 50 µg/ml Geneticin (Life Technologies) Verification of cassette insertion was determined by PCR using combinations of primers that anneal outside of the HO flanking sequence and specific to synthesized DNA cassette. The engineered YB-210 diploid strain was then subjected to sporulation and tetrad dissection. One spore, which was not derived from a tetrad that generated four viable spores, was confirmed for a single "a" mating type and subsequently named GLBRCY22-3. LoxP-KanMX-loxP marker rescue was carried out by expression of Cre recombinase as published elsewhere (Guldener et al., *Nucleic Acids Res.* 24:2519 (1996)). Deletion of engineered CpXylA and ScTAL1, and endogenous ScGRE3 were performed by integration of PCR product using a LoxP-KanMX-LoxP cassette (Guldener et al., *Nucleic Acids Res.* 24:2519 (1996)) into the marker-rescued versions of GLBRCY22-3 (GLBRCY36), GLBRCY127 (GLBRCY132) and GLBRCY128 (GLBRCY133, see Table 1).

Directed Evolution:

For aerobic adaptation, GLBRCY22-3 strain was inoculated at $OD_{600}$=0.05-0.1 in 250 mL YP media containing 2% xylose and 0.1% glucose. The first 15 transfers took place over 53 days with serial 1:10 dilutions in fresh media occurring every 3-4 days. After transfer 15, the adaptation culture was diluted every 2-3 days over the course of 44 additional days, ending after transfer 34. For anaerobic adaptation, GLBRCY127 strain was inoculated at $OD_{600}$=0.05-0.1 in a flask containing 50 mL YP media containing 2% xylose, 0.1% glucose and 50 µg/mL Geneticin, and then placed in an anaerobic chamber. For the first two anaerobic transfers, the media also contained 40 µg/L ergosterol (Sigma-Aldrich) and 4 g/L Tween-80 (Sigma-Aldrich). Anaerobic cultures were maintained in suspension using a stir bar and magnetic stir plate, and passaged every 7 days during the first 5 transfers. After the fifth transfer, the culture was passaged every 3-4 days with the final fourteenth transfer finishing 66 days since the start of the anaerobic adaptation. Xylose concentrations in the media at the end of each transfer cycle were measure by YSI 2700 Select instrument. At the end of each adaptation, the culture at 1:10,000 dilution was spread onto multiple YPD-Geneticin plates and incubated at 30° C. for 48 hours. Single clonal isolates were picked and evaluated for growth in YPX media either aerobically or anaerobically in an anaerobic chamber as described previously (Wolbach et al., *PNAS* 108:13212 (2011); Sato et al., *Applied and Environmental Microbiol.* 80:540 (2014)).

Aerobic and Anaerobic Xylose Consumption Assays:

Aerobic tube and anaerobic flask growth and sugar consumption assays were performed as previously described (2). For fermentative evaluation in industrial lignocellulosic media, strains were cultured in Minibio bioreactors (Applikon Biotechnology) with 100 mL 6% glucan loading AFEX pretreated corn stover hydrolysate. Inoculum cultures were prepared as previously described (2). Vessels were sparged with $N_2$ (150 sccm) and inoculated with a starting $OD_{600}$=0.1. Vessels were maintained at 30° C. and pH 5.0 with NaOH or HCl, and stirred at 500 rpm. Media glucose and xylose concentrations from aerobic tube and anaerobic flask experiments were determined by YSI instrument. Extracellular glucose, xylose, ethanol, glycerol, and xylitol concentrations from aerobic and anaerobic bioreactor experiments were determined by high performance liquid chromatography (HPLC) and refractive index detection RID as published elsewhere (Schwalbach et al., *Applied and Environmental Microbiol.* 78:3442 (2012)).

Quantification of Intracellular Pentose Metabolic Intermediates:

To quantify intracellular metabolites, 5 mL to 10 mL of cell culture was rapidly removed from bioreactors with a 20 cc sterile syringe and 4 mL aliquots were applied to a filtration manifold unit (Hoefer FH 225V) outfitted with sterile 25 ml nylon filters (Whatman; Nylon; 0.45 µm pore size), and the cells captured on the filters under vacuum. To reduce the background associated with metabolites present in ACSH and SynH, the cells were then rapidly washed with 5 ml of synthetic hydrolysate media (Schwalbach et al., *Applied and Environmental Microbiol.* 78:3442 (2012)) at pH5 lacking amino acids and replacing 9% sorbitol in place of 6% glucose and 3% xylose. The filters were then removed and rapidly placed in 15 mL conical tubes containing ice-cold extraction buffer [(Demke et al., *Biotechnol. Biofuels* 6:89 (2013)); acetonitrile-methanol-water, 40:40:20, 0.1% formic acid] and flash frozen in a dry ice ethanol bath.

The concentration of xylulose-5-phosphate was determined using reverse Phase Ion Pairing high performance liquid chromatography (HPLC) and electrospray ionization tandem mass spectrometry (ESI-MS/MS). Reagents and nonlabeled reference compounds were from Sigma Aldrich Co. (Saint Louis, Mo., USA). Reverse Phase Ion Pairing HPLC was carried out by an adaptation of the method of Buescher et al., and was used to quantify xylulose-5-phosphate in intracellular extracts. Compounds were separated on a Waters Acquity Ascentis HSS-T3 C18 column, 150×2.0 mm, 1.8 µm particle size. The mobile phase A consisted of 95:5 Water:methanol+10 mM TBA+15 mM acetic acid, and mobile phase B was isopropyl alcohol.

Concentrations of xylose, xylulose, xylitol, and trehalose were determined in sample extracts by methoximation/trimethylsilylation derivatization followed by gas chromatography-mass spectrometry (GC-MS) using $^{13}C$ labeled internal standards for each compound. Pyridine was anhydrous and stored over molecular sieves. 2% methoxyamine hydrochloride in pyridine (MOX reagent) and N-methyl,N-(trimethylsilyl) trifluoroacetamidewith 1% trimethylchlorosilane (MSTFA+1% TMCS) were obtained from Thermo Fisher Scientific. Xylose, xlulose, xylitol, and trehaolse reference materials, all >98% purity, (99 atom %) uniformly labeled $^{13}C_5$-xylose, $^{13}C_5$-xylitol, and $^{13}C_{12}$-trehalose, and immobilized xylose isomerase, were obtained from Sigma Aldrich. Briefly, 50 µL aliquots of extract were transferred to 2.5 mL centrifuge tubes to which 20 µL were added of a solution containing U—$^{13}C_5$-xylitol, U—$^{13}C_{12}$-trehalose, U—$^{13}C_5$-xylose, and U—$^{13}C_5$ Xylulose. Samples were evaporated to dryness under reduced pressure in a Savant SPD 131A rotary evaporator with cryogenic cold trap for 3-4 hours. Dried samples were then treated with 30 µL 2% methoxyamine hydrochloride in pyridine at 60° C. for 45 minutes, followed by addition of 70 µL MSTFA+1% TMCS and incubation at 60° C. for an additional 30 minutes. The derivatized samples and standards were then analyzed by GC-MS on an Agilent 5975 MSD with a Combi PAL1 autosampler (CTC analytics) and a 6890A GC oven equipped with a 30 m×0.25 mm ID×0.25µ df HP5-MS (5% phenyl polydimethylsiloxane) capillary column. The inlet was held at 250° C. and operated in split mode with a ratio of 10:1 with a glass wool packed single bevel split liner. The flow rate of helium through the analytical column was 1.2 mL per minute. The oven temperature was held at 174° C. for 18 minutes then increased linearly at 30° C. per minute to a final temperature of 280° C. and held for 3 minutes before returning to starting conditions with a 30 second equilibration time prior to starting the next injection sequence. Standards used to construct a calibration curve were prepared by the same procedure using 20 µL of the same internal standard mixture added to known amounts of reference compounds to obtain eight (8) concentration levels ranging from 1 to 500 µM in the final 100 µL volume of derivatization reagents.

The mass spectrometer was operated in SIM mode divided into time segments so that only the relevant masses were monitored over the times when each target compound eluted, allowing optimal dwell times of 150 ms while still recording at least 20 points over the width of a peak. SIM masses were selected corresponding to fragments ($M^{+/-}-15$) containing all 5-$^{13}C$ atoms for the labeled internal standards of xylose and xylulose (m/z 457), and xylitol (m/z 427) and a 6-$^{13}C$ fragment (m/z 361) for trehalose to allow detection without interference from the isotopic masses of the coeluting natural abundance compounds. The natural $^{12}C$ compounds were monitored with the corresponding $^{12}C$ ions except for xylulose which was monitored with a much more abundant m/z 263 ion that was found to be free of interference from the labeled internal standard.

Results were calculated from relative peak areas of analytes to their corresponding internal standards interpolated with a calibration curve of relative natural standard/$^{13}C$ internal standard peak areas versus relative standard/$^{13}C$ internal standard concentrations. The $^{13}C$ xylulose and $^{13}C$ xylose internal standards were found to contain approximately a 3:1 ratio of $^{13}C$ xylose:$^{13}C$ xylulose based on GC-MS TIC peak areas. All aspects of instrument operation, data collection, and calculation of results were handled by Agilent MassHunter for GC software VB.07.00 and Mass Hunter Workstation Quantitative Analysis v.B.06.00.

REFERENCES

1. Sherman F (2002) Getting started with yeast. *Methods in enzymology* 350:3-41.
2. Parreiras L S, et al. (2014) Engineering and two-stage evolution of a lignocellulosic hydrolysate-tolerant *Saccharomyces cerevisiae* strain for anaerobic fermentation of xylose from AFEX pretreated corn stover. *PloS one* 9(9):e107499.
3. Brachmann C B, et al. (1998) Designer deletion strains derived from *Saccharomyces cerevisiae* S288C: a useful set of strains and plasmids for PCR-mediated gene disruption and other applications. *Yeast* 14(2):115-132.
4. Entian K D & Kotter P (2007) *Yeast Genetic Strain and Plasmid Collections*. (Academic Press, Amsterdam).
5. Guldener U, Heck S, Fielder T, Beinhauer J, & Hegemann J H (1996) A new efficient gene disruption cassette for repeated use in budding yeast. *Nucleic acids research* 24(13):2519-2524.
6. Winzeler E A, et al. (1999) Functional characterization of the *S. cerevisiae* genome by gene deletion and parallel analysis. *Science* 285(5429):901-906.
7. Gietz R D & Schiestl R H (2007) High-efficiency yeast transformation using the LiAc/SS carrier DNA/PEG method. *Nature protocols* 2(1):31-34.

8. Haft R J, et al. (2014) Correcting direct effects of ethanol on translation and transcription machinery confers ethanol tolerance in bacteria. *Proceedings of the National Academy of Sciences of the United States of America* 111(25):E2576-2585.
9. Chin C S, et al. (2013) Nonhybrid, finished microbial genome assemblies from long-read SMRT sequencing data. *Nature methods* 10(6):563-569.
10. Proux-Wera E, Armisen D, Byrne K P, & Wolfe K H (2012) A pipeline for automated annotation of yeast genome sequences by a conserved-synteny approach. *BMC bioinformatics* 13:237.
11. Boratyn G M, et al. (2013) BLAST: a more efficient report with usability improvements. *Nucleic acids research* 41(Web Server issue):W29-33.
12. Bonfield J K & Whitwham A (2010) Gap5—editing the billion fragment sequence assembly. *Bioinformatics* 26(14):1699-1703.
13. Bankevich A, et al. (2012) SPAdes: a new genome assembly algorithm and its applications to single-cell sequencing. *Journal of computational biology: a journal of computational molecular cell biology* 19(5):455-477.
14. McKenna A, et al. (2010) The Genome Analysis Toolkit: a MapReduce framework for analyzing next-generation DNA sequencing data. *Genome research* 20(9):1297-1303.
15. Hinrichs A S, et al. (2006) The UCSC Genome Browser Database: update 2006. *Nucleic acids research* 34(Database issue):D590-598.
16. Wohlbach D J, et al. (2011) Comparative genomics of xylose-fermenting fungi for enhanced biofuel production. *Proceedings of the National Academy of Sciences of the United States of America* 108(32):13212-13217.
17. Schwalbach M S, et al. (2012) Complex physiology and compound stress responses during fermentation of alkali-pretreated corn stover hydrolysate by an *Escherichia coli* ethanologen. *Applied and environmental microbiology* 78(9):3442-3457.
18. Lill R (2009) Function and biogenesis of iron-sulphur proteins. *Nature* 460(7257):831-838.
19. Schilke B, Voisine C, Beinert H, & Craig E (1999) Evidence for a conserved system for iron metabolism in the mitochondria of *Saccharomyces cerevisiae*. *Proceedings of the National Academy of Sciences of the United States of America* 96(18):10206-10211.
20. Ohtake Y & Yabuuchi S (1991) Molecular cloning of the gamma-glutamylcysteine synthetase gene of *Saccharomyces cerevisiae*. *Yeast* 7(9):953-961.
21. Saito H & Posas F (2012) Response to hyperosmotic stress. *Genetics* 192(2):289-318.
22. Tanaka K, et al. (1990) IRA2, a second gene of *Saccharomyces cerevisiae* that encodes a protein with a domain homologous to mammalian ras GTPase-activating protein. *Molecular and cellular biology* 10(8):4303-4313.
23. Harashima T, Anderson S, Yates J R, 3rd, & Heitman J (2006) The kelch proteins Gpb1 and Gpb2 inhibit Ras activity via association with the yeast RasGAP neurofibromin homologs Ira1 and Ira2. *Molecular cell* 22(6):819-830.
24. Lang G I, et al. (2013) Pervasive genetic hitchhiking and clonal interference in forty evolving yeast populations. *Nature* 500(7464):571-574.
25. Dutkiewicz R, et al. (2004) Sequence-specific interaction between mitochondrial Fe—S scaffold protein Isu and Hsp70 Ssq1 is essential for their in vivo function. *The Journal of biological chemistry* 279(28):29167-29174.

We claim:

1. A recombinant yeast that has been genetically engineered to: (a) include non-native genes that facilitate xylose fermentation, (b) exhibit reduced amounts of functional Isu1 polypeptide, (c) include a disabling mutation in a gene encoding Isu1 polypeptide, and (d) include a disabling mutation in a gene encoding Hog1 polypeptide and exhibiting reduced amounts of functional Hog1 polypeptide,
    wherein the genetically engineered recombinant yeast is capable of increased aerobic xylose fermentation relative to a recombinant yeast having the same genetic background of non-native genes that facilitate xylose fermentation but not exhibiting said reduced amounts of functional Isu1 polypeptide.

2. The recombinant yeast of claim 1, wherein the disabling mutation in the gene encoding Isu1 comprises a substitution of a tyrosine for the histidine at amino acid residue position 138 of SEQ ID NO:6.

3. The recombinant yeast of claim 1, wherein the disabling mutation in the gene encoding Hog1 comprises a deletion of the adenine at nucleotide position 844 of SEQ ID NO:7.

4. The recombinant yeast of claim 1, wherein the recombinant yeast is of the genus *Saccharomyces*.

5. The recombinant yeast of claim 4, wherein the recombinant yeast is of the species *Saccharomyces cerevisiae*.

6. The recombinant yeast of claim 1, wherein a nucleic acid sequence comprising the disabling mutation in the gene encoding Isu1 is integrated into a chromosome of the recombinant yeast.

7. The recombinant yeast of claim 1, wherein the non-native genes that facilitate xylose fermentation comprise TAL1, XylA and XYL3.

8. A yeast inoculum, comprising: (a) the recombinant yeast of claim 1; and (b) a culture medium.

9. A recombinant yeast that has been genetically engineered to: (a) include non-native genes that facilitate xylose fermentation, and (b) exhibit reduced amounts of functional Isu1 and Hog1 polypeptides, and at least one of functional Gre3, Ira1, and Ira2 polypeptides,
wherein the genetically engineered recombinant yeast is capable of increased anaerobic xylose fermentation relative to a recombinant yeast having the same genetic background of non-native genes that facilitate xylose fermentation but not exhibiting said reduced amounts of functional Isu1 and Hog1 polypeptides, and at least one of functional Gre3, Ira1, and Ira2 polypeptides.

10. The recombinant yeast of claim 9, comprising a disabling mutation in a gene encoding Isu1, a disabling mutation in a gene encoding Hog1, and at least one of a disabling mutation in a gene encoding Gre3, a disabling mutation in a gene encoding Ira1, and a disabling mutation in a gene encoding Ira2.

11. The recombinant yeast of claim 10, wherein a disabling mutation in the gene encoding Isu1 comprises a substitution of a tyrosine for the histidine at amino acid residue position 138 of SEQ ID NO:6; wherein a disabling mutation in the gene encoding Hog1 comprises a deletion of the adenine at nucleotide position 844 of SEQ ID NO:7; wherein a disabling mutation in the gene encoding Gre3 comprises a substitution of a threonine for the alanine at amino acid residue position 46 of SEQ ID NO:4; and wherein a disabling mutation in the gene encoding Ira2 comprises a substitution of a stop codon for the glutamate at amino acid residue at position 2927 of SEQ ID NO:2.

12. The recombinant yeast of claim 10, wherein a nucleic acid sequence comprising the disabling mutations is integrated into a chromosome of the recombinant yeast.

13. The recombinant yeast of claim 9, wherein the recombinant yeast exhibits reduced amounts of functional Isu1, Hog1, Gre3, and Ira2 polypeptides and is capable of increased anaerobic xylose fermentation relative to a recombinant yeast having the same genetic background of non-native genes that facilitate xylose fermentation but not exhibiting said reduced amounts of functional Isu1, Hog1, Gre3, and Ira2 polypeptides.

14. The recombinant yeast of claim 9, wherein the recombinant yeast is of the genus *Saccharomyces*.

15. The recombinant yeast of claim 14, wherein the recombinant yeast is of the species *Saccharomyces cerevisiae*.

16. The recombinant yeast of claim 9, wherein the non-native genes that facilitate xylose fermentation comprise TAL1, XylA and XYL3.

17. A yeast inoculum, comprising: (a) the recombinant yeast of claim 9; and (b) a culture medium.

18. A method of fermenting a hydrolysate having xylose into ethanol, comprising: contacting under ethanol-producing conditions the recombinant yeast of claim 4 or the recombinant yeast of claim 9 to the hydrolysate for a period of time sufficient to allow fermentation of at least a portion of the hydrolysate into ethanol.

19. The method of claim 18, further comprising separating the ethanol from fermented hydrolysate.

20. The method of claim 18, further comprising hydrolyzing a cellulosic material to produce the hydrolysate comprising xylose; and contacting the recombinant yeast to the hydrolysate under conditions that permit fermentation.

21. The method of claim 20, wherein the cellulosic material comprises a lignocellulosic biomass.

22. The method of claim 21, wherein the lignocellulosic biomass comprises at least one material selected from the group consisting of agricultural residues, wood, municipal solid wastes, paper and pulp industry wastes, and herbaceous crops.

* * * * *

SEQUENCE LISTING

```
<160> NUMBER OF SEQ ID NOS: 10

<210> SEQ ID NO 1
<211> LENGTH: 12012
<212> TYPE: DNA
<213> ORGANISM: Saccharomyces cerevisiae
<220> FEATURE:
<221> NAME/KEY: misc_feature
<223> OTHER INFORMATION: IRA2 coding sequence

<400> SEQUENCE: 1
ataccgatac tttccatacg cacttgattt agaggccggc tccactatcg agattgaaaa      60
tcagtatgga gaagtgatct tcttgggcaa gtatggctct tctccaatga ttaacttaag     120
gccaccttca agattatctg cagaaagttt acaggcatcc caagagccat tttactcctt     180
tcaaatcgat acgttaccag aactggatga ctctagtatc atcagtacat ccatttcact     240
ctcttatgac ggtgacgaca atgaaaaagc cctgacttgg gaagaactct aggtcaaact     300
ctatttttat acagcaatga gtacctttc acatacacat aaatatatta aatataataa     360
atacaataaa tataaaataa ccctttcga aactctttac ttcctaaggc ctctcattac     420
ttatcaccta gcatcatgct cttcatacat gccatctact ttcaaacgat atacggctaa     480
ccagaaaagt acggacaatc agggacgagc agggacatga cgccttccgc acagatccca     540
gagaaaagca gggaaacaag aaaataagaa aacaagaaaa acagtagtta cccttgtaag     600
tgtcatccac aacagaacca atactcttac tcttccgctc attcccgca gaatgataga      660 actattctaa atccccttgc cttgcttggc cttgacttgg gttgggactt ggacctctag     720
```

```
aaccgatgtg ccttcaaaca tcttagcgag ataagagtct gccattaatg catcgagcca    780
atatcttgga ctagtacgag gttcacgtag cctttcttgc acggcaccag cgtcccaccc    840
caagttcttt gctatactga ccgccttaca cattttagtg tgattccaac ccaaagtagc    900
tcctcaaaaa gggtcacccg atcggtgaat caatccgcgg cgcagaaatg ttcgtagagc    960
tctcgtttct tctagaacgc tcccttgatg aaacgaaaat ttccatcaca ataaagctcg   1020
cacgcctttt tgaaaacccc aagctttgct gtgtcttctt gtgaaaagtt ttgcccaacg   1080
attatctatt ctacatataa ccggggagtt aagcacatcc tattgcccta cattctctcc   1140
gcttacttca ttgtctagag ctcctgggaa acaaaagacc gaaaaagcga aaacaaaatc   1200
agaacaaggc ttaagtactt tttcaccaat tgtagcaaac atttaaccac atttttagcac  1260
actagcatat agcattgtcc tctgttattc gttttgcttt tctcctttag tgttactttt   1320
cccccaacgt tacaccattt tttgatatca actaaactgt atacattatc tttcttcagg   1380
gagaagcatg tcccagccca ctaagaataa gaagaaagaa cacgggaccg attccaagtc   1440
atcccgcatg actcggacgt tggttaatca tattcttttt gaaagaattc tcccgatcct   1500
tccggtggag tctaatctaa gtacctattc ggaagtggaa gagtattcct cattcatttc   1560
atgcagatct gtgctcatta acgttaccgt ttcccgagat gcaaatgcta tggtggaagg   1620
caccttggag ttgatagaat cgcttcttca agggcacgaa atcatttcag ataagggtag   1680
cagtgacgtt attgaatcaa tactgattat actaagattg ttaagtgatg cgctagagta   1740
taattggcaa aatcaagaaa gccttcatta caacgacatt tcgactcacg tagaacatga   1800
ccaagaacag aagtacagac caaagcttaa cagtattctg cccgactact cgtcgactca   1860
ttccaatggc aacaaacact ttttccacca gagcaaacct caggcactga taccggaact   1920
ggcatcgaaa ttgcttgaga gttgcgcgaa gttgaagttc aatacaagaa ctttgcaaat   1980
tttacaaaat atgatcagtc atgttcatgg aaacattcta acgactttga gttcctcgat   2040
tcttccccgc cacaaatcct atctgacaag gcacaaccat ccttctcatt gtaaaatgat   2100
tgactctact ctaggccata ttctccgatt tgtagcggct tccaatccgt ccgagtattt   2160
tgaatttatc agaaagagtg tgcaagtgcc cgtaacacag acacacacgc attcacactc   2220
ccattcacac tcttttgccat cttccgttta taacagcata gtgccccact ttgatctttt   2280
cagcttcatc tatttaagca agcataattt taagaaatac ttggaactca tcaaaaactt   2340
atcggtgacg ttaaggaaaa cgatttatca ttgcctactt ttgcattaca gcgccaaagc   2400
aataatgttt tggataatgg ctaggcctgc ggaatattat gaactcttca acttattaaa   2460
agataataac aatgaacact cgaaatcctt aaacacgtta aaccatacac ttttcgagga   2520
gatccattcg acttttaatg tgaatagcat gataaccacc aatcaaaatg ctcatcaagg   2580
ctcatcttcc ccttcgtcct cctcgccatc gtcaccacct agctcatcat catcggataa   2640
caacaatcaa aacataatag caaaatcctt aagtcgtcag ctttctcacc accagtcata   2700
cattcaacag cagtctgaaa gaaaactaca ttcttcatgg actacaaact ctcaatcctc   2760
tacttcactg tcatcttcaa cgtctaattc aacaacaact gatttctcta ctcacactca   2820
accaggagaa tatgaccctt ccttaccaga tactcccacg atgtctaaca tcactattag   2880
tgcatcttca ttattatctc aaactccaac tccaacaaca caattgcaac agcggttgaa   2940
ctcagcagct gcagccgccg ccgcagctgc ttcaccatcg aattccaccc caactggata   3000
cacagcagag caacaaagtc gcgcttcata cgatgcacac aaaactggcc atactggtaa   3060
ggattatgac gaacatttttt tgtctgtcac tcgtttggat aatgttttgg agttatacac   3120
```

```
gcactttgat gatactgagg tactaccaca cacatccgta ctgaagtttt taactacttt    3180
gacaatgttc gatattgacc tttttaatga attaaacgct acatcattca aatatattcc    3240
tgattgtact atgcatcgtc caaaagaaag aacaagttct ttcaataata ctgcacacga    3300
gacaggttcc gaaaagactt cgggtataaa acatattaca caaggcttaa agaaattaac    3360
ttctttacct tcctcaacca aaaaaactgt aaaatttgtg aagatgttgc taagaaattt    3420
aaatgggaat caagctgtat cagatgttgc cctcttagat acaatgaggg ccttactatc    3480
attctttaca atgacttctg cggtcttcct cgtggataga aacttaccct cagtacttt     3540 tgccaagaga ctcatcccca taatggggac aaatttaagc gtcggtcaag actggaattc    3600
aaaaataaat aacagtttga tggtttgttt gaaaaaaaac tccaccacgt ttgttcaatt    3660
acaattaata ttcttctctt cagctattca attcgatcat gaattattac tggcacgtct    3720
gagcatcgat acaatggcca acaatttaaa catgcagaag ctatgccttt atactgaagg    3780
attcaggata ttcttcgaca taccaagtaa gaaggaattg cggaaggcaa ttgcggttaa    3840
aatttctaaa ttttttcaaaa cattattctc cattatagca gatattcttt tacaagaatt    3900
tccgtatttt gatgagcaaa tcaccgacat agttgcttcc attcttgacg gtacaattat    3960
caatgagtat ggtacgaaga acatttcaa ggggagctca ccctctttat gttcgacaac    4020
ccggtcaaga tcaggatcta catctcaaag ttcaatgaca ccagtttctc cgctgggact    4080
ggatactgat atatgtccaa tgaacaccct gtctttagtt ggttcaagta cttcaagaaa    4140
ttctgacaac gttaattcat taaacagttc accaagaac ttgtcttctg atccatactt    4200
gtcacatctt gtggccccaa gagcgcgtca tgctttaggt gggccatcta gtattataag    4260
gaataaaata ccgactacat tgacttcacc tccaggaacg gaaaaatctt caccagtaca    4320
acgtccgcaa acgaaagca tcagtgccac accaatggcc ataacaaatt ctactccatt    4380
atcgtcggca gcattcggaa ttcgatcgcc tttgcagaaa ataagaacga ggcgttattc    4440
cgatgaaagt ttaggaaaat tcatgaaatc aacaaataat tacattcaag aacatttgat    4500
accaaaagat ttgaatgaag caactcttca agatgctaga agaataatga ttaatatttt    4560
cagtattttt aagagaccga atagttactt catcattcct cacaatataa actcgaattt    4620
acaatgggtt tcgcaggatt ttagaaatat tatgaaaccg attttcgtcg ccatcgtaag    4680
tccggatgta gatttacaga atactgctca atcattcatg ataccttat tatcgaatgt     4740 tattacttat ggtgaatcag atgagaatat cagtattgaa gggtatcatc ttctttgcag    4800
ttacactgta acattatttg caatgggcct tttcgatttg aaaattaata atgaaaagcg    4860
tcaaattctc ttggatataa ctgtcaagtt tatgaaggtt agatcacatt tagcagggat    4920
cgcggaggcc tcacaccaca tggaatacat aagtgattct gaaaaactca cctttccgct    4980
gattatgggg actgttggta gggccctatt tgtttcatta tactctagtc aacaaaaaat    5040
tgaaaagact ttaaagattg cttacacaga gtatctttct gcaatcaatt ttcatgagag    5100
gaatattgat gatgctgata aaacttgggt tcataatatt gagtttgtag aagcgatgtg    5160
tcatgacaac tacacaactt ctggttcaat tgctttccaa aggaggacaa gaaataatat    5220
tttacgattt gctactattc ctaacgctat cttacttgat tctatgagga tgatctataa    5280
gaagtggcat acttacacac acagtaaaag tttagaaaaa caagaacgga acgacttcag    5340
aaatttcgcg ggtatttta cctctcttgtc gggtatccta ttcatcaata aaagatatt     5400 gcaagaaatg tatccatacc tactcgacac cgttcagaa ttgaaaaaaa atatagactc     5460 tttatctca aaacaatgcc aatggttaaa ctatccggat ttattaacga gagaaaattc    5520
```

-continued

```
aagagatatt ctaagtgtag aactgcatcc tttgtcttttt aacttacttt ttaataattt    5580
gaggctcaag ttaaaagaac ttgcttgttc agacttatca ataccagaaa atgaaagttc    5640
ctatgtttta ttagaacaaa taatcaaaat gctgcggaca atcctaggtc gtgatgatga    5700
caattatgta atgatgcttt tttccacaga gattgtagat cttattgatt tattgacaga    5760
tgaaataaaa aaataccag cctattgtcc aaaatatctc aaggcaatta ttcaaatgac    5820
caaaatgttc agtgccttgc agcactcaga ggttaattta ggtgtcaaaa atcattttca    5880
cgttaaaaat aaatggttga ggcaaatcac tgattggttt caagtgagta ttgcgagaga    5940
gtacgatttc gaaaacttgt caaaacctct aaaagaaatg gatttggtaa aaagagacat    6000
ggatattcta tacatagata cggcaatcga agcttcaacc gctattgcgt acctcacgag    6060
acatactttc ttagagattc cacctgccgc gtcagatccc gaactatctc gatctaggtc    6120
tgtgatattt gggttttatt tcaacatctt aatgaaaggc cttgaaaaaa gtagtgatcg    6180
tgacaattac ccagtattct tgaggcacaa aatgagtgtc ctcaacgaca atgtaatact    6240
ttcattaaca aatcttttcaa acaccaatgt tgatgcgagt ttgcagttca ccttaccgat    6300
gggctattcc ggaaatcgaa acattaggaa tgcattttttg gaggtcttca ttaatatcgt    6360
tacgaactat cggacataca cggctaaaac tgaccttgga aaattagagg cagcagacaa    6420
attttttgcga tatcgattg aacatcccca gctatcgtcc tttggagcag cggtttgtcc    6480
cgctagcgat attgatgctt atgctgctgg cttaataaat gcatttgaaa cgaggaatgc    6540
cacccacatt gtagtggcac agttgattaa aaatgaaatt gaaaaatctt ccagacctac    6600
ggatatcctt agaagaaata gctgtgctac gagatcatta tctatgctag ccaggtccaa    6660
gggtaacgaa tatttgattc gcactttgca accattacta aaaaaaatta ccagaacag    6720
agatttttt gaaattgaga aactaaaacc ggaagattca gatgctgaac gtcaaataga    6780
gctcttcgtt aaatacatga atgaattatt ggaatccata tccaactccg tatcttattt    6840
tccccctcct ttattttata tttgccaaaa catttataaa gttgcgtgtg aaaaatttcc    6900
ggatcacgca attatcgccg ctgggtcttt cgtgttttta cggtttttttt gtcctgcttt    6960
agtcagccct gattctgaaa atatcataga tatttctcac ttgagcgaaa agcgtacctt    7020
catcagcttg gctaaagtta tccaaaatat tgccaatggc tcagaaaatt tctccagatg    7080
gccagctttg tgttcccaaa aggattttct taaggaatgt agcgatagaa ttttcagatt    7140
cctagctgaa ctttgtagaa cagatcgcac gatagacatc caagtgagaa cagacccaac    7200
gccaattgca tttgactatc aattccttca ttcctttgtt tacctttacg gtcttgaggt    7260
gagaaggaat gtgctaaatg aagcaaaaca tgatgatggt gacattgatg gtgacgattt    7320
ctataagacc acatttttac ttattgatga tgttcttggc caattaggcc aacctaaaat    7380
ggaattttcc aatgaaatac caatatacat aagagaacat atggacgact atccggaact    7440
gtatgagttc atgaataggc acgcgttcag aaacattgag acttcaacag cgtacagccc    7500
aagcgttcac gagtccacct caagtgaagg cattccaatt attacgttaa caatgtcaaa    7560
tttctcagac agacatgtgg acattgatac agttgcttac aagttcttgc aaatttatgc    7620
tcgaatctgg accaccaaac actgttttaat aatcgactgt acagaatttg acgagggagg    7680
gcttgatatg aggaaattta tttctttggt tatgggacta ttaccagaag ttgcacccaa    7740
aaattgtata ggctgttact actttaacgt aaacgagaca tttatggata attatgaaa    7800
atgtttggac aaagacaacg tatatgtttc ctcgaaaatt cctcattatt tcattaatag    7860
taactctgat gaaggactta tgaaatctgt gggtataact ggacaagggt tgaaggttct    7920
```

```
gcaagatatt cgtgtctctc tgcatgatat cacgctttat gacgaaaaaa gaaatagatt    7980
tacgccggta tcgttgaaaa taggcgatat ttactttcaa gtcttgcatg aaactcctag    8040
gcaatataaa ataagggaca tgggtacttt attcgacgta aaattcaatg atgtctacga    8100
aattagccga atatttgaag tacatgtttc gtcaataact ggagtggcag ctgaatttac    8160
agtaactttt caggacgaga gaaggttgat ttttagtagt ccgaaatacc ttgaaattgt    8220
gaagatgttc tattacgcac agatccggtt agaaagtgaa tatgaaatgg ataataattc    8280
gagtacctcc tccccaaatt caaacaacaa ggacaaacag cagaaagaga gaacaaaact    8340
attgtgccac ctactgttag tatctcttat tggtctgttt gatgagagta aaaaaatgaa    8400
aaacagttcg tataacctaa tagctgccac tgaggcgtca tttggtttga actttggctc    8460 ccatttcat cgctctcccg aggtgtacgt ccccgaagat actacaacat ttttaggtgt    8520
tattggaaag tctcttgcag agtctaatcc agaactcaca gcctatatgt ttatctatgt    8580
tttggaggca ttgaagaaca acgtaattcc tcacgtttac atccctcata ccatttgcgg    8640
tttgtcttat tggatcccta atttatacca acatgtgtat ttggctgatg atgaagaagg    8700
ccccgaaaac atatctcaca ttttccgaat tcttatcagg ctctctgtga gagagactga    8760 cttttaaagcc gtatacatgc aatatgtttg gttgctactt ttagatgatg ccgcttaac    8820 tgacattatc gttgatgaag ttattaatca tgcgttagaa agagactccg aaaaccgcga    8880
ttggaagaaa acaatatcgt tactgactgt cctacccact actgaggttg ctaataatat    8940
tattcaaaaa atattggcaa aaattagatc attttttaccg tcattgaagt tagaagctat    9000
gacccaaagt tggtctgaac taacaatatt agttaagata agcatccacg ttttttttga    9060
aacttctttg ctggtacaga tgtacttacc agagatcctg tttatcgtat ccttattaat    9120
tgatgttggt ccaagggaac tcagatcatc actacaccag ctattaatga atgtatgcca    9180
ttccttggct attaactcag ctttaccaca agatcataga aataatctag atgaaataag    9240
tgatatattt gcacatcaaa aggtgaagtt tatgtttggg ttcagcgagg acaaaggacg    9300
aattttacag atttttagcg cttcttcttt tgcaagcaag tttaatattc tggatttctt    9360
catcaataat atattattgc tgatggaata ttcttcaacg tacgaagcaa acgtgtggaa    9420
gacaagatac aagaaatatg tcttggaatc tgtgtttaca agtaattctt ttcttcggc    9480 acgttcaatc atgattgttg gtataatggg taaatcttac ataactgaag ggttatgcaa    9540
ggctatgtta attgaaacca tgaaagttat cgccgaacca aagattactg acgagcatct    9600
tttcttagcc atatctcata ttttttactta ttccaaaatt gttgaaggtt tggatcccaa    9660
ccttgactta atgaagcact tattttggtt ttcaacactc ttccttgaat cacgtcaccc    9720
gataattttt gagggtgccc ttctctttgt gtcaaactgt ataaggcgcc tatacatggc    9780
ccagtttgaa aatgaaagcg aaacatcatt gataagtact ttacttaagg ggagaaagtt    9840
tgctcatacc ttttttaagca agatagagaa tcttagtggt attgtttgga atgaagataa    9900
ttttacacac attctgattt tcatcattaa taaaggacta ccaatccttt tcattaagag    9960
tacggctttt gatttcttga agatgatgtt tagaaactcc tactttgagc atcaaatcaa    10020
tcagaaatct gatcattatt tgtgctatat gttcctattg tattttgttt taaactgcaa    10080
tcaatttgag gaacttttag gtgacgttga ttttgaagga gaaatggtta acattgaaaa    10140
caagaacacc attcctaaaa ttttgttaga gtggttgagt tcggataacg aaaatgcaaa    10200 cattccctc tatcaaggtg cgatactgtt caaatgttca gttacggatg aaccaagtag    10260
atttaggttt gcgttgatta ttaggcatct attgacaaag aaacccattt gtgcattgcg    10320
```

-continued

```
ttttttacagt gttattcgta acgaaataag aaaaatatca gcatttgagc aaaattcgga   10380
ttgtgttcca cttgctttcg atattttaaa cttattagtg acgcattcag agtctaattc   10440
gttagaaaaa cttcacgaag aatccattga acgtctaacc aaaagaggtt tatcgattgt   10500
gacttcttct ggtatatttg cgaagaactc cgacatgatg ataccttag atgtaaaacc    10560
tgaagatatc tatgaacgta agagaataat gacaatgatt ttatcaagga tgtcatgttc   10620
tgcttagagg tgttacataa actaatgaaa gaaatatcaa tatctatctg taagcatgaa   10680
tgtacatatc tcatgttagg gttttcttat cgctaatttt tcgcaatttg ttacgtgggt   10740
tgctttttata cagctacaat ttttatatat tctatcgtgt aatgaatggc tcagtaaatt   10800
caagcgccac atagactaat gtacatacca atgcatttta attgtaagaa taaaaggggc   10860
cattcatcta ccgtcttagt tgaaagtgtt tctgtgaatt ttttcaaatt ccgttttttc   10920
cttttatat  aatagcatgg tggcacgagc atcttcgact gaagaatgct caccttcttg   10980
aatggaaatt tttaaaacct ccctggttaa tttctttaag ctgggtgttt tacccttagc   11040
atacaacttc ctgaatggga ggtgtcttga agtgtccctg agtagtgact ttgggtggga   11100
taacatcaat gcttcgagat catgctttaa agcgtgccct acaagaattc taccttccag   11160
aatatccgca gtcttttttt gagcttcttt gaatgtaatg gcattttca tatgctctgg    11220
tttaatacca ctaacccaag ttctccattc tacaactttc tctcttggct taacaaattc   11280
atcgaggacg acatgtccaa ataaatttac gattgatatt ctagctaacg cagactcttt   11340
accctcggga ccaacgccta caaattcaca atccatggcg atgtatttcc caatttcttt   11400
actcttatta ctattaatac gagtatcttc cgaaataccc acttttactg gctctttaat   11460
agtagtacta gtatttgctt tatttgggtt gaattcaaac acttttccct cgagcttgtc   11520
tttctcatgc ttactaatct ccttgttcat gttatatacc atgtccataa ttttactgcc   11580
gttttttgcgc tttcgagggg catattgggt tgtactactg acatttactg ttttgctaac   11640
tttcttaacg tttctgattt tcctatttga ttgcttattc tttccattgg aggtaggatt   11700
gctttcggag gctaatagtg cctgccagtt tgaagagaga gccattaaaa ctgtacgcta   11760
tctactttat taaatctgta aacgtctatg aagcctctag aaccaggctt taaatggatt   11820
gtggttgcga tgaggttagt ttaacttttg aaattttct tttttttagc cgaccttaca    11880
tatcagcccg cgtcaaaaaa tatacggtat aataattctc aatagataca ggctactgaa   11940
caggaaaact aaataaaaca gtgtttgtaa aaccccacc acaccataat aagacgataa    12000
tggacacggt ga                                                      12012
```

<210> SEQ ID NO 2
<211> LENGTH: 3079
<212> TYPE: PRT
<213> ORGANISM: Saccharomyces cerevisiae

<400> SEQUENCE: 2

```
Met Ser Gln Pro Thr Lys Asn Lys Lys Glu His Gly Thr Asp Ser
1               5                   10                  15

Lys Ser Ser Arg Met Thr Arg Thr Leu Val Asn His Ile Leu Phe Glu
            20                  25                  30

Arg Ile Leu Pro Ile Leu Pro Val Glu Ser Asn Leu Ser Thr Tyr Ser
        35                  40                  45

Glu Val Glu Glu Tyr Ser Ser Phe Ile Ser Cys Arg Ser Val Leu Ile
    50                  55                  60
```

-continued

```
Asn Val Thr Val Ser Arg Asp Ala Asn Ala Met Val Glu Gly Thr Leu
 65                  70                  75                  80

Glu Leu Ile Glu Ser Leu Leu Gln Gly His Glu Ile Ile Ser Asp Lys
             85                  90                  95

Gly Ser Ser Asp Val Ile Glu Ser Ile Leu Ile Ile Leu Arg Leu Leu
            100                 105                 110

Ser Asp Ala Leu Glu Tyr Asn Trp Gln Asn Gln Glu Ser Leu His Tyr
            115                 120                 125

Asn Asp Ile Ser Thr His Val Glu His Asp Gln Gln Lys Tyr Arg
130                 135                 140

Pro Lys Leu Asn Ser Ile Leu Pro Asp Tyr Ser Ser Thr His Ser Asn
145                 150                 155                 160

Gly Asn Lys His Phe Phe His Gln Ser Lys Pro Gln Ala Leu Ile Pro
                165                 170                 175

Glu Leu Ala Ser Lys Leu Leu Glu Ser Cys Ala Lys Leu Lys Phe Asn
            180                 185                 190

Thr Arg Thr Leu Gln Ile Leu Gln Asn Met Ile Ser His Val His Gly
            195                 200                 205

Asn Ile Leu Thr Thr Leu Ser Ser Ser Ile Leu Pro Arg His Lys Ser
210                 215                 220

Tyr Leu Thr Arg His Asn His Pro Ser His Cys Lys Met Ile Asp Ser
225                 230                 235                 240

Thr Leu Gly His Ile Leu Arg Phe Val Ala Ala Ser Asn Pro Ser Glu
                245                 250                 255

Tyr Phe Glu Phe Ile Arg Lys Ser Val Gln Val Pro Val Thr Gln Thr
            260                 265                 270

His Thr His Ser His Ser His Ser His Ser Leu Pro Ser Ser Val Tyr
            275                 280                 285

Asn Ser Ile Val Pro His Phe Asp Leu Phe Ser Phe Ile Tyr Leu Ser
            290                 295                 300

Lys His Asn Phe Lys Lys Tyr Leu Glu Leu Ile Lys Asn Leu Ser Val
305                 310                 315                 320

Thr Leu Arg Lys Thr Ile Tyr His Cys Leu Leu Leu His Tyr Ser Ala
            325                 330                 335

Lys Ala Ile Met Phe Trp Ile Met Ala Arg Pro Ala Glu Tyr Tyr Glu
            340                 345                 350

Leu Phe Asn Leu Leu Lys Asp Asn Asn Glu His Ser Lys Ser Leu
            355                 360                 365

Asn Thr Leu Asn His Thr Leu Phe Glu Glu Ile His Ser Thr Phe Asn
370                 375                 380

Val Asn Ser Met Ile Thr Thr Asn Gln Asn Ala His Gln Gly Ser Ser
385                 390                 395                 400

Ser Pro Ser Ser Ser Pro Ser Ser Pro Ser Ser Ser Ser
                405                 410                 415

Asp Asn Asn Asn Gln Asn Ile Ile Ala Lys Ser Leu Ser Arg Gln Leu
            420                 425                 430

Ser His His Gln Ser Tyr Ile Gln Gln Gln Ser Glu Arg Lys Leu His
            435                 440                 445

Ser Ser Trp Thr Thr Asn Ser Gln Ser Ser Ser Leu Ser Ser Ser
450                 455                 460

Thr Ser Asn Ser Thr Thr Thr Asp Phe Ser Thr His Thr Gln Pro Gly
465                 470                 475                 480
```

-continued

```
Glu Tyr Asp Pro Ser Leu Pro Asp Thr Pro Thr Met Ser Asn Ile Thr
                485                 490                 495

Ile Ser Ala Ser Ser Leu Leu Ser Gln Thr Pro Thr Pro Thr Thr Gln
            500                 505                 510

Leu Gln Gln Arg Leu Asn Ser Ala Ala Ala Ala Ala Ala Ala Ala Ala
        515                 520                 525

Ser Pro Ser Asn Ser Thr Pro Thr Gly Tyr Thr Ala Glu Gln Gln Ser
    530                 535                 540

Arg Ala Ser Tyr Asp Ala His Lys Thr Gly His Thr Gly Lys Asp Tyr
545                 550                 555                 560

Asp Glu His Phe Leu Ser Val Thr Arg Leu Asp Asn Val Leu Glu Leu
                565                 570                 575

Tyr Thr His Phe Asp Asp Thr Glu Val Leu Pro His Thr Ser Val Leu
            580                 585                 590

Lys Phe Leu Thr Thr Leu Thr Met Phe Asp Ile Asp Leu Phe Asn Glu
        595                 600                 605

Leu Asn Ala Thr Ser Phe Lys Tyr Ile Pro Asp Cys Thr Met His Arg
    610                 615                 620

Pro Lys Glu Arg Thr Ser Ser Phe Asn Asn Thr Ala His Glu Thr Gly
625                 630                 635                 640

Ser Glu Lys Thr Ser Gly Ile Lys His Ile Thr Gln Gly Leu Lys Lys
                645                 650                 655

Leu Thr Ser Leu Pro Ser Ser Thr Lys Lys Thr Val Lys Phe Val Lys
            660                 665                 670

Met Leu Leu Arg Asn Leu Asn Gly Asn Gln Ala Val Ser Asp Val Ala
        675                 680                 685

Leu Leu Asp Thr Met Arg Ala Leu Leu Ser Phe Phe Thr Met Thr Ser
    690                 695                 700

Ala Val Phe Leu Val Asp Arg Asn Leu Pro Ser Val Leu Phe Ala Lys
705                 710                 715                 720

Arg Leu Ile Pro Ile Met Gly Thr Asn Leu Ser Val Gly Gln Asp Trp
                725                 730                 735

Asn Ser Lys Ile Asn Asn Ser Leu Met Val Cys Leu Lys Lys Asn Ser
            740                 745                 750

Thr Thr Phe Val Gln Leu Gln Leu Ile Phe Phe Ser Ser Ala Ile Gln
        755                 760                 765

Phe Asp His Glu Leu Leu Leu Ala Arg Leu Ser Ile Asp Thr Met Ala
    770                 775                 780

Asn Asn Leu Asn Met Gln Lys Leu Cys Leu Tyr Thr Glu Gly Phe Arg
785                 790                 795                 800

Ile Phe Phe Asp Ile Pro Ser Lys Lys Glu Leu Arg Lys Ala Ile Ala
                805                 810                 815

Val Lys Ile Ser Lys Phe Phe Lys Thr Leu Phe Ser Ile Ile Ala Asp
            820                 825                 830

Ile Leu Leu Gln Glu Phe Pro Tyr Phe Asp Glu Gln Ile Thr Asp Ile
        835                 840                 845

Val Ala Ser Ile Leu Asp Gly Thr Ile Ile Asn Glu Tyr Gly Thr Lys
    850                 855                 860

Lys His Phe Lys Gly Ser Ser Pro Ser Leu Cys Ser Thr Thr Arg Ser
865                 870                 875                 880

Arg Ser Gly Ser Thr Ser Gln Ser Ser Met Thr Pro Val Ser Pro Leu
                885                 890                 895
```

```
Gly Leu Asp Thr Asp Ile Cys Pro Met Asn Thr Leu Ser Leu Val Gly
                900                 905                 910

Ser Ser Thr Ser Arg Asn Ser Asp Asn Val Asn Ser Leu Asn Ser Ser
        915                 920                 925

Pro Lys Asn Leu Ser Ser Asp Pro Tyr Leu Ser His Leu Val Ala Pro
        930                 935                 940

Arg Ala Arg His Ala Leu Gly Gly Pro Ser Ser Ile Ile Arg Asn Lys
945                 950                 955                 960

Ile Pro Thr Thr Leu Thr Ser Pro Pro Gly Thr Glu Lys Ser Ser Pro
                965                 970                 975

Val Gln Arg Pro Gln Thr Glu Ser Ile Ser Ala Thr Pro Met Ala Ile
        980                 985                 990

Thr Asn Ser Thr Pro Leu Ser Ser  Ala Ala Phe Gly Ile  Arg Ser Pro
        995                 1000                1005

Leu Gln  Lys Ile Arg Thr Arg  Arg Tyr Ser Asp Glu  Ser Leu Gly
        1010                1015                1020

Lys Phe  Met Lys Ser Thr Asn  Asn Tyr Ile Gln Glu  His Leu Ile
        1025                1030                1035

Pro Lys  Asp Leu Asn Glu Ala  Thr Leu Gln Asp Ala  Arg Arg Ile
        1040                1045                1050

Met Ile  Asn Ile Phe Ser Ile  Phe Lys Arg Pro Asn  Ser Tyr Phe
        1055                1060                1065

Ile Ile  Pro His Asn Ile Asn  Ser Asn Leu Gln Trp  Val Ser Gln
        1070                1075                1080

Asp Phe  Arg Asn Ile Met Lys  Pro Ile Phe Val Ala  Ile Val Ser
        1085                1090                1095

Pro Asp  Val Asp Leu Gln Asn  Thr Ala Gln Ser Phe  Met Asp Thr
        1100                1105                1110

Leu Leu  Ser Asn Val Ile Thr  Tyr Gly Glu Ser Asp  Glu Asn Ile
        1115                1120                1125

Ser Ile  Glu Gly Tyr His Leu  Leu Cys Ser Tyr Thr  Val Thr Leu
        1130                1135                1140

Phe Ala  Met Gly Leu Phe Asp  Leu Lys Ile Asn Asn  Glu Lys Arg
        1145                1150                1155

Gln Ile  Leu Leu Asp Ile Thr  Val Lys Phe Met Lys  Val Arg Ser
        1160                1165                1170

His Leu  Ala Gly Ile Ala Glu  Ala Ser His His Met  Glu Tyr Ile
        1175                1180                1185

Ser Asp  Ser Glu Lys Leu Thr  Phe Pro Leu Ile Met  Gly Thr Val
        1190                1195                1200

Gly Arg  Ala Leu Phe Val Ser  Leu Tyr Ser Ser Gln  Gln Lys Ile
        1205                1210                1215

Glu Lys  Thr Leu Lys Ile Ala  Tyr Thr Glu Tyr Leu  Ser Ala Ile
        1220                1225                1230

Asn Phe  His Glu Arg Asn Ile  Asp Asp Ala Asp Lys  Thr Trp Val
        1235                1240                1245

His Asn  Ile Glu Phe Val Glu  Ala Met Cys His Asp  Asn Tyr Thr
        1250                1255                1260

Thr Ser  Gly Ser Ile Ala Phe  Gln Arg Arg Thr Arg  Asn Asn Ile
        1265                1270                1275

Leu Arg  Phe Ala Thr Ile Pro  Asn Ala Ile Leu Leu  Asp Ser Met
        1280                1285                1290
```

```
Arg Met Ile Tyr Lys Lys Trp His Thr Tyr Thr His Ser Lys Ser
1295                1300                1305

Leu Glu Lys Gln Glu Arg Asn Asp Phe Arg Asn Phe Ala Gly Ile
1310                1315                1320

Leu Ala Ser Leu Ser Gly Ile Leu Phe Ile Asn Lys Lys Ile Leu
1325                1330                1335

Gln Glu Met Tyr Pro Tyr Leu Leu Asp Thr Val Ser Glu Leu Lys
1340                1345                1350

Lys Asn Ile Asp Ser Phe Ile Ser Lys Gln Cys Gln Trp Leu Asn
1355                1360                1365

Tyr Pro Asp Leu Leu Thr Arg Glu Asn Ser Arg Asp Ile Leu Ser
1370                1375                1380

Val Glu Leu His Pro Leu Ser Phe Asn Leu Leu Phe Asn Asn Leu
1385                1390                1395

Arg Leu Lys Leu Lys Glu Leu Ala Cys Ser Asp Leu Ser Ile Pro
1400                1405                1410

Glu Asn Glu Ser Ser Tyr Val Leu Leu Glu Gln Ile Ile Lys Met
1415                1420                1425

Leu Arg Thr Ile Leu Gly Arg Asp Asp Asp Asn Tyr Val Met Met
1430                1435                1440

Leu Phe Ser Thr Glu Ile Val Asp Leu Ile Asp Leu Leu Thr Asp
1445                1450                1455

Glu Ile Lys Lys Ile Pro Ala Tyr Cys Pro Lys Tyr Leu Lys Ala
1460                1465                1470

Ile Ile Gln Met Thr Lys Met Phe Ser Ala Leu Gln His Ser Glu
1475                1480                1485

Val Asn Leu Gly Val Lys Asn His Phe His Val Lys Asn Lys Trp
1490                1495                1500

Leu Arg Gln Ile Thr Asp Trp Phe Gln Val Ser Ile Ala Arg Glu
1505                1510                1515

Tyr Asp Phe Glu Asn Leu Ser Lys Pro Leu Lys Glu Met Asp Leu
1520                1525                1530

Val Lys Arg Asp Met Asp Ile Leu Tyr Ile Asp Thr Ala Ile Glu
1535                1540                1545

Ala Ser Thr Ala Ile Ala Tyr Leu Thr Arg His Thr Phe Leu Glu
1550                1555                1560

Ile Pro Pro Ala Ala Ser Asp Pro Glu Leu Ser Arg Ser Arg Ser
1565                1570                1575

Val Ile Phe Gly Phe Tyr Phe Asn Ile Leu Met Lys Gly Leu Glu
1580                1585                1590

Lys Ser Ser Asp Arg Asp Asn Tyr Pro Val Phe Leu Arg His Lys
1595                1600                1605

Met Ser Val Leu Asn Asp Asn Val Ile Leu Ser Leu Thr Asn Leu
1610                1615                1620

Ser Asn Thr Asn Val Asp Ala Ser Leu Gln Phe Thr Leu Pro Met
1625                1630                1635

Gly Tyr Ser Gly Asn Arg Asn Ile Arg Asn Ala Phe Leu Glu Val
1640                1645                1650

Phe Ile Asn Ile Val Thr Asn Tyr Arg Thr Tyr Thr Ala Lys Thr
1655                1660                1665

Asp Leu Gly Lys Leu Glu Ala Ala Asp Lys Phe Leu Arg Tyr Thr
1670                1675                1680
```

```
Ile Glu His Pro Gln Leu Ser  Ser Phe Gly Ala Ala  Val Cys Pro
    1685             1690             1695

Ala Ser Asp Ile Asp Ala Tyr  Ala Ala Gly Leu Ile  Asn Ala Phe
    1700             1705             1710

Glu Thr Arg Asn Ala Thr His  Ile Val Val Ala Gln  Leu Ile Lys
    1715             1720             1725

Asn Glu Ile Glu Lys Ser Ser  Arg Pro Thr Asp Ile  Leu Arg Arg
    1730             1735             1740

Asn Ser Cys Ala Thr Arg Ser  Leu Ser Met Leu Ala  Arg Ser Lys
    1745             1750             1755

Gly Asn Glu Tyr Leu Ile Arg  Thr Leu Gln Pro Leu  Leu Lys Lys
    1760             1765             1770

Ile Ile Gln Asn Arg Asp Phe  Phe Glu Ile Glu Lys  Leu Lys Pro
    1775             1780             1785

Glu Asp Ser Asp Ala Glu Arg  Gln Ile Glu Leu Phe  Val Lys Tyr
    1790             1795             1800

Met Asn Glu Leu Leu Glu Ser  Ile Ser Asn Ser Val  Ser Tyr Phe
    1805             1810             1815

Pro Pro Pro Leu Phe Tyr Ile  Cys Gln Asn Ile Tyr  Lys Val Ala
    1820             1825             1830

Cys Glu Lys Phe Pro Asp His  Ala Ile Ile Ala Ala  Gly Ser Phe
    1835             1840             1845

Val Phe Leu Arg Phe Phe Cys  Pro Ala Leu Val Ser  Pro Asp Ser
    1850             1855             1860

Glu Asn Ile Ile Asp Ile Ser  His Leu Ser Glu Lys  Arg Thr Phe
    1865             1870             1875

Ile Ser Leu Ala Lys Val Ile  Gln Asn Ile Ala Asn  Gly Ser Glu
    1880             1885             1890

Asn Phe Ser Arg Trp Pro Ala  Leu Cys Ser Gln Lys  Asp Phe Leu
    1895             1900             1905

Lys Glu Cys Ser Asp Arg Ile  Phe Arg Phe Leu Ala  Glu Leu Cys
    1910             1915             1920

Arg Thr Asp Arg Thr Ile Asp  Ile Gln Val Arg Thr  Asp Pro Thr
    1925             1930             1935

Pro Ile Ala Phe Asp Tyr Gln  Phe Leu His Ser Phe  Val Tyr Leu
    1940             1945             1950

Tyr Gly Leu Glu Val Arg Arg  Asn Val Leu Asn Glu  Ala Lys His
    1955             1960             1965

Asp Asp Gly Asp Ile Asp Gly  Asp Asp Phe Tyr Lys  Thr Thr Phe
    1970             1975             1980

Leu Leu Ile Asp Asp Val Leu  Gly Gln Leu Gly Gln  Pro Lys Met
    1985             1990             1995

Glu Phe Ser Asn Glu Ile Pro  Ile Tyr Ile Arg Glu  His Met Asp
    2000             2005             2010

Asp Tyr Pro Glu Leu Tyr Glu  Phe Met Asn Arg His  Ala Phe Arg
    2015             2020             2025

Asn Ile Glu Thr Ser Thr Ala  Tyr Ser Pro Ser Val  His Glu Ser
    2030             2035             2040

Thr Ser Ser Glu Gly Ile Pro  Ile Ile Thr Leu Thr  Met Ser Asn
    2045             2050             2055

Phe Ser Asp Arg His Val Asp  Ile Asp Thr Val Ala  Tyr Lys Phe
    2060             2065             2070
```

-continued

Leu Gln Ile Tyr Ala Arg Ile Trp Thr Thr Lys His Cys Leu Ile
2075                    2080                2085

Ile Asp Cys Thr Glu Phe Asp Glu Gly Leu Asp Met Arg Lys
2090                2095                2100

Phe Ile Ser Leu Val Met Gly Leu Leu Pro Glu Val Ala Pro Lys
2105                2110                2115

Asn Cys Ile Gly Cys Tyr Tyr Phe Asn Val Asn Glu Thr Phe Met
2120                2125                2130

Asp Asn Tyr Gly Lys Cys Leu Asp Lys Asp Asn Val Tyr Val Ser
2135                2140                2145

Ser Lys Ile Pro His Tyr Phe Ile Asn Ser Asn Ser Asp Glu Gly
2150                2155                2160

Leu Met Lys Ser Val Gly Ile Thr Gly Gln Gly Leu Lys Val Leu
2165                2170                2175

Gln Asp Ile Arg Val Ser Leu His Asp Ile Thr Leu Tyr Asp Glu
2180                2185                2190

Lys Arg Asn Arg Phe Thr Pro Val Ser Leu Lys Ile Gly Asp Ile
2195                2200                2205

Tyr Phe Gln Val Leu His Glu Thr Pro Arg Gln Tyr Lys Ile Arg
2210                2215                2220

Asp Met Gly Thr Leu Phe Asp Val Lys Phe Asn Asp Val Tyr Glu
2225                2230                2235

Ile Ser Arg Ile Phe Glu Val His Val Ser Ser Ile Thr Gly Val
2240                2245                2250

Ala Ala Glu Phe Thr Val Thr Phe Gln Asp Glu Arg Arg Leu Ile
2255                2260                2265

Phe Ser Ser Pro Lys Tyr Leu Glu Ile Val Lys Met Phe Tyr Tyr
2270                2275                2280

Ala Gln Ile Arg Leu Glu Ser Glu Tyr Glu Met Asp Asn Asn Ser
2285                2290                2295

Ser Thr Ser Ser Pro Asn Ser Asn Asn Lys Asp Lys Gln Gln Lys
2300                2305                2310

Glu Arg Thr Lys Leu Leu Cys His Leu Leu Val Ser Leu Ile
2315                2320                2325

Gly Leu Phe Asp Glu Ser Lys Lys Met Lys Asn Ser Ser Tyr Asn
2330                2335                2340

Leu Ile Ala Ala Thr Glu Ala Ser Phe Gly Leu Asn Phe Gly Ser
2345                2350                2355

His Phe His Arg Ser Pro Glu Val Tyr Val Pro Glu Asp Thr Thr
2360                2365                2370

Thr Phe Leu Gly Val Ile Gly Lys Ser Leu Ala Glu Ser Asn Pro
2375                2380                2385

Glu Leu Thr Ala Tyr Met Phe Ile Tyr Val Leu Glu Ala Leu Lys
2390                2395                2400

Asn Asn Val Ile Pro His Val Tyr Ile Pro His Thr Ile Cys Gly
2405                2410                2415

Leu Ser Tyr Trp Ile Pro Asn Leu Tyr Gln His Val Tyr Leu Ala
2420                2425                2430

Asp Asp Glu Glu Gly Pro Glu Asn Ile Ser His Ile Phe Arg Ile
2435                2440                2445

Leu Ile Arg Leu Ser Val Arg Glu Thr Asp Phe Lys Ala Val Tyr
2450                2455                2460

```
Met Gln Tyr Val Trp Leu Leu Leu Leu Asp Asp Gly Arg Leu Thr
2465                2470                2475

Asp Ile Ile Val Asp Glu Val Ile Asn His Ala Leu Glu Arg Asp
2480                2485                2490

Ser Glu Asn Arg Asp Trp Lys Lys Thr Ile Ser Leu Leu Thr Val
2495                2500                2505

Leu Pro Thr Thr Glu Val Ala Asn Asn Ile Ile Gln Lys Ile Leu
2510                2515                2520

Ala Lys Ile Arg Ser Phe Leu Pro Ser Leu Lys Leu Glu Ala Met
2525                2530                2535

Thr Gln Ser Trp Ser Glu Leu Thr Ile Leu Val Lys Ile Ser Ile
2540                2545                2550

His Val Phe Phe Glu Thr Ser Leu Leu Val Gln Met Tyr Leu Pro
2555                2560                2565

Glu Ile Leu Phe Ile Val Ser Leu Leu Ile Asp Val Gly Pro Arg
2570                2575                2580

Glu Leu Arg Ser Ser Leu His Gln Leu Leu Met Asn Val Cys His
2585                2590                2595

Ser Leu Ala Ile Asn Ser Ala Leu Pro Gln Asp His Arg Asn Asn
2600                2605                2610

Leu Asp Glu Ile Ser Asp Ile Phe Ala His Gln Lys Val Lys Phe
2615                2620                2625

Met Phe Gly Phe Ser Glu Asp Lys Gly Arg Ile Leu Gln Ile Phe
2630                2635                2640

Ser Ala Ser Ser Phe Ala Ser Lys Phe Asn Ile Leu Asp Phe Phe
2645                2650                2655

Ile Asn Asn Ile Leu Leu Leu Met Glu Tyr Ser Ser Thr Tyr Glu
2660                2665                2670

Ala Asn Val Trp Lys Thr Arg Tyr Lys Lys Tyr Val Leu Glu Ser
2675                2680                2685

Val Phe Thr Ser Asn Ser Phe Leu Ser Ala Arg Ser Ile Met Ile
2690                2695                2700

Val Gly Ile Met Gly Lys Ser Tyr Ile Thr Glu Gly Leu Cys Lys
2705                2710                2715

Ala Met Leu Ile Glu Thr Met Lys Val Ile Ala Glu Pro Lys Ile
2720                2725                2730

Thr Asp Glu His Leu Phe Leu Ala Ile Ser His Ile Phe Thr Tyr
2735                2740                2745

Ser Lys Ile Val Glu Gly Leu Asp Pro Asn Leu Asp Leu Met Lys
2750                2755                2760

His Leu Phe Trp Phe Ser Thr Leu Phe Leu Glu Ser Arg His Pro
2765                2770                2775

Ile Ile Phe Glu Gly Ala Leu Leu Phe Val Ser Asn Cys Ile Arg
2780                2785                2790

Arg Leu Tyr Met Ala Gln Phe Glu Asn Glu Ser Glu Thr Ser Leu
2795                2800                2805

Ile Ser Thr Leu Leu Lys Gly Arg Lys Phe Ala His Thr Phe Leu
2810                2815                2820

Ser Lys Ile Glu Asn Leu Ser Gly Ile Val Trp Asn Glu Asp Asn
2825                2830                2835

Phe Thr His Ile Leu Ile Phe Ile Ile Asn Lys Gly Leu Ser Asn
2840                2845                2850
```

| | | | | | | | | | | | |
|---|---|---|---|---|---|---|---|---|---|---|---|
|Pro|Phe|Ile|Lys|Ser|Thr|Ala|Phe|Asp|Phe|Leu|Lys|Met|Met|Phe|
| |2855| | | |2860| | | |2865| | | | | |

Arg Asn Ser Tyr Phe Glu His Gln Ile Asn Gln Lys Ser Asp His
2870                    2875                    2880

Tyr Leu Cys Tyr Met Phe Leu Leu Tyr Phe Val Leu Asn Cys Asn
2885                    2890                    2895

Gln Phe Glu Glu Leu Leu Gly Asp Val Asp Phe Glu Gly Glu Met
2900                    2905                    2910

Val Asn Ile Glu Asn Lys Asn Thr Ile Pro Lys Ile Leu Leu Glu
2915                    2920                    2925

Trp Leu Ser Ser Asp Asn Glu Asn Ala Asn Ile Thr Leu Tyr Gln
2930                    2935                    2940

Gly Ala Ile Leu Phe Lys Cys Ser Val Thr Asp Glu Pro Ser Arg
2945                    2950                    2955

Phe Arg Phe Ala Leu Ile Ile Arg His Leu Leu Thr Lys Lys Pro
2960                    2965                    2970

Ile Cys Ala Leu Arg Phe Tyr Ser Val Ile Arg Asn Glu Ile Arg
2975                    2980                    2985

Lys Ile Ser Ala Phe Glu Gln Asn Ser Asp Cys Val Pro Leu Ala
2990                    2995                    3000

Phe Asp Ile Leu Asn Leu Leu Val Thr His Ser Glu Ser Asn Ser
3005                    3010                    3015

Leu Glu Lys Leu His Glu Glu Ser Ile Glu Arg Leu Thr Lys Arg
3020                    3025                    3030

Gly Leu Ser Ile Val Thr Ser Ser Gly Ile Phe Ala Lys Asn Ser
3035                    3040                    3045

Asp Met Met Ile Pro Leu Asp Val Lys Pro Glu Asp Ile Tyr Glu
3050                    3055                    3060

Arg Lys Arg Ile Met Thr Met Ile Leu Ser Arg Met Ser Cys Ser
3065                    3070                    3075

Ala

<210> SEQ ID NO 3
<211> LENGTH: 1278
<212> TYPE: DNA
<213> ORGANISM: Saccharomyces cerevisiae
<220> FEATURE:
<221> NAME/KEY: misc_feature
<223> OTHER INFORMATION: GRE3 coding sequence

<400> SEQUENCE: 3

```
cttctagggg gcctatcaag taaattactc ctggtacact gaagtatata agggatatag    60
aagcaaatag ttgtcagtgc aatccttcaa gacgattggg aaaatactgt aatataaatc   120
gtaaaggaaa attggaaatt ttttaaagat gtcttcactg ttactctta ataacggtct    180
gaaaatgccc ctagtcggct tagggtgctg gaaaattgac aaaaaagtct gtgcgaatca   240
aatttatgaa gctatcaaat taggctaccg tttattcgat ggtgcttgcg actacggcaa   300
cgaaaaggaa gttggtgaag gtatcaggaa agccatctcc gaaggtcttg tttctagaaa   360
ggatatattt gttgtttcaa agttatgaa caatttttcac catcctgatc atgtaaaatt   420
agctttaaag aagaccttaa gcgatatggg acttgattat ttagacctgt attatattca   480
cttcccaatc gccttcaaat atgttccatt tgaagagaaa taccctccag gattctatac   540
gggcgcagat gacgagaaga aaggtcacat caccgaagca catgtaccaa tcatagatac   600
gtaccgggct ctggaagaat gtgttgatga aggcttgatt aagtctattg gtgtttccaa   660
```

-continued

```
ctttcaggga agcttgattc aagatttatt acgtggttgt agaatcaagc ccgtggcttt      720
gcaaattgaa caccatcctt atttgactca agaacaccta gttgagtttt gtaaattaca      780
cgatatccaa gtagttgctt actcctcctt cggtcctcaa tcattcattg agatggactt      840
acagttggca aaaccacgc caactctgtt cgagaatgat gtaatcaaga aggtctcaca       900
aaaccatcca ggcagtacca cttcccaagt attgcttaga tgggcaactc agagaggcat     960
tgccgtcatt ccaaaatctt ccaagaagga aaggttactt ggcaacctag aaatcgaaaa     1020
aaagttcact ttaacggagc aagaattgaa ggatatttct gcactaaatg ccaacatcag     1080
atttaatgat ccatggacct ggttggatgg taaattcccc acttttgcct gatccagcca     1140
gtaaaatcca tactcaacga cgatatgaac aaatttccct cattccgatg ctgtatatgt     1200
gtataaattt ttacatgctc ttctgtttag acacagaaca gctttaaata aaatgttgga     1260 tatactttttt ctgcctgt                                                  1278
```

<210> SEQ ID NO 4
<211> LENGTH: 327
<212> TYPE: PRT
<213> ORGANISM: Saccharomyces cerevisiae

<400> SEQUENCE: 4

```
Met Ser Ser Leu Val Thr Leu Asn Asn Gly Leu Lys Met Pro Leu Val
1               5                   10                  15

Gly Leu Gly Cys Trp Lys Ile Asp Lys Lys Val Cys Ala Asn Gln Ile
            20                  25                  30

Tyr Glu Ala Ile Lys Leu Gly Tyr Arg Leu Phe Asp Gly Ala Cys Asp
        35                  40                  45

Tyr Gly Asn Glu Lys Glu Val Gly Glu Gly Ile Arg Lys Ala Ile Ser
    50                  55                  60

Glu Gly Leu Val Ser Arg Lys Asp Ile Phe Val Val Ser Lys Leu Trp
65                  70                  75                  80

Asn Asn Phe His His Pro Asp His Val Lys Leu Ala Leu Lys Lys Thr
                85                  90                  95

Leu Ser Asp Met Gly Leu Asp Tyr Leu Asp Leu Tyr Tyr Ile His Phe
            100                 105                 110

Pro Ile Ala Phe Lys Tyr Val Pro Phe Glu Glu Lys Tyr Pro Pro Gly
        115                 120                 125

Phe Tyr Thr Gly Ala Asp Asp Glu Lys Lys Gly His Ile Thr Glu Ala
    130                 135                 140

His Val Pro Ile Ile Asp Thr Tyr Arg Ala Leu Glu Glu Cys Val Asp
145                 150                 155                 160

Glu Gly Leu Ile Lys Ser Ile Gly Val Ser Asn Phe Gln Gly Ser Leu
                165                 170                 175

Ile Gln Asp Leu Leu Arg Gly Cys Arg Ile Lys Pro Val Ala Leu Gln
            180                 185                 190

Ile Glu His His Pro Tyr Leu Thr Gln Glu His Leu Val Glu Phe Cys
        195                 200                 205

Lys Leu His Asp Ile Gln Val Val Ala Tyr Ser Ser Phe Gly Pro Gln
    210                 215                 220

Ser Phe Ile Glu Met Asp Leu Gln Leu Ala Lys Thr Thr Pro Thr Leu
225                 230                 235                 240

Phe Glu Asn Asp Val Ile Lys Lys Val Ser Gln Asn His Pro Gly Ser
                245                 250                 255
```

Thr Thr Ser Gln Val Leu Leu Arg Trp Ala Thr Gln Arg Gly Ile Ala
            260                 265                 270

Val Ile Pro Lys Ser Ser Lys Lys Glu Arg Leu Leu Gly Asn Leu Glu
        275                 280                 285

Ile Glu Lys Lys Phe Thr Leu Thr Glu Gln Glu Leu Lys Asp Ile Ser
    290                 295                 300

Ala Leu Asn Ala Asn Ile Arg Phe Asn Asp Pro Trp Thr Trp Leu Asp
305                 310                 315                 320

Gly Lys Phe Pro Thr Phe Ala
            325

<210> SEQ ID NO 5
<211> LENGTH: 648
<212> TYPE: DNA
<213> ORGANISM: Saccharomyces cerevisiae
<220> FEATURE:
<221> NAME/KEY: misc_feature
<223> OTHER INFORMATION: ISU1 coding sequence

<400> SEQUENCE: 5
tcttaaatcc ataagaacat cccttcatat aacaattgaa taaggaaaac acaacacata      60
acacatattt aacctgatgc ttcctgttat aacgagattt gcaaggcctg ctctgatggc     120
catcagacct gtgaatgcca tgggggtttt gagagcgtcc agcataacga aaaggcttta     180
tcatcccaag gtcatagagc attatacaca tccaagaaac gtcggctcat tagataaaaa     240
attgcccaac gtcggcactg gtctagtggg tgcgccagcg tgcggtgatg tgatgaggtt     300
gcagatcaaa gtcaacgact ctactggcgt tattgaagat gtcaaattca aaacttttgg     360
atgtggctcc gccattgcct cctcttcata tatgactgaa ttggtacagg ggatgacctt     420
ggacgatgcg gcaaaaatta agaacactga aattgctaag gagttgagct tgcccccagt     480
caagttgcat tgctctatgt tagcggaaga tgcgatcaag gcagctatta aggactacaa     540
atctaagaga aacactccaa ccatgttatc gtaatgaata agaagataac cgggacaaga     600
acaagatcaa accctcacta atcaacaagt tggacttaat ttgtgcaa                  648

<210> SEQ ID NO 6
<211> LENGTH: 165
<212> TYPE: PRT
<213> ORGANISM: Saccharomyces cerevisiae

<400> SEQUENCE: 6

Met Leu Pro Val Ile Thr Arg Phe Ala Arg Pro Ala Leu Met Ala Ile
1               5                   10                  15

Arg Pro Val Asn Ala Met Gly Val Leu Arg Ala Ser Ser Ile Thr Lys
            20                  25                  30

Arg Leu Tyr His Pro Lys Val Ile Glu His Tyr Thr His Pro Arg Asn
        35                  40                  45

Val Gly Ser Leu Asp Lys Lys Leu Pro Asn Val Gly Thr Gly Leu Val
    50                  55                  60

Gly Ala Pro Ala Cys Gly Asp Val Met Arg Leu Gln Ile Lys Val Asn
65                  70                  75                  80

Asp Ser Thr Gly Val Ile Glu Asp Val Lys Phe Lys Thr Phe Gly Cys
            85                  90                  95

Gly Ser Ala Ile Ala Ser Ser Ser Tyr Met Thr Glu Leu Val Gln Gly
        100                 105                 110

Met Thr Leu Asp Asp Ala Ala Lys Ile Lys Asn Thr Glu Ile Ala Lys
    115                 120                 125

```
Glu Leu Ser Leu Pro Pro Val Lys Leu His Cys Ser Met Leu Ala Glu
            130                 135                 140

Asp Ala Ile Lys Ala Ala Ile Lys Asp Tyr Lys Ser Lys Arg Asn Thr
145                 150                 155                 160

Pro Thr Met Leu Ser
                165

<210> SEQ ID NO 7
<211> LENGTH: 1308
<212> TYPE: DNA
<213> ORGANISM: Saccharomyces cerevisiae
<220> FEATURE:
<221> NAME/KEY: misc_feature
<223> OTHER INFORMATION: HOG1 coding sequence

<400> SEQUENCE: 7
atgaccacta acgaggaatt cattaggaca cagatattcg gtacagtttt cgagatcaca        60
aatagataca atgatttaaa ccccgttggg atgggggcat ttgggttggt ttgctcagcc       120
acggacactt tgacatctca gccagttgcc attaagaaaa tcatgaaacc tttttccact       180
gcagtgctgg ccaaaaggac atatcgtgaa ctaaaactac taaaacatct aagacacgag       240
aacttgattt gccttcagga catatttctt tctccattgg aagatatata ttttgtcacg       300
gaattacaag gaacagattt acatagactc ttgcaaacaa gacccttgga aaagcaattt       360
gttcagtatt tcctatacca aattctaagg ggtttaaaat acgttcactc cgcgggcgtc       420
attcatagag atttgaaacc gagcaacatt ctgattaatg aaaactgtga tttgaagatt       480
tgcgatttcg gtctagcaag aattcaagac cctcaaatga caggctatgt ttccactaga       540
tactacaggg cacctgaaat catgctaacg tggcaaaaat atgacgtcga ggtcgacatt       600
tggtccgctg gttgtatttt tgccgaaatg attgaaggta agcctttgtt ccctgggaaa       660
gatcatgttc accaattttc gatcatcact gacttgttgg gatctccgcc aaaggatgtg       720
ataaatacta tttgttccga aaatactcta aaatttgtta cttcgttacc acacagagat       780
ccaattccat tttctgaaag atttaaaaca gtcgaacctg atgccgtaga cctttttgga       840
aaaatgctgg tttttgatcc taagaagaga atcactgcgg cggatgcctt ggctcatcct       900
tattcggctc cttaccacga tccaacggat gaaccagtag ccgatgccaa gttcgattgg       960
cactttaatg acgctgatct gcctgtcgat acctggcgtg ttatgatgta ctcagaaatc      1020
ctagacttcc ataagattgg tggcagtgat ggacagattg atatatctgc cacgtttgat      1080
gaccaagttg ctgcagccac cgctgccgcg gcgcaggcac aggctcaggc tcaggctcaa      1140
gttcagttaa acatggctgc gcattcgcat aatggcgctg gcactactgg aaatgatcac      1200
tcagatatag ctggtggaaa caaagtcagc gatcatgtag ctgcaaatga caccattacg      1260
gactacggta accaggccat acagtacgct aatgagttcc aacagtaa               1308

<210> SEQ ID NO 8
<211> LENGTH: 435
<212> TYPE: PRT
<213> ORGANISM: Saccharomyces cerevisiae

<400> SEQUENCE: 8

Met Thr Thr Asn Glu Glu Phe Ile Arg Thr Gln Ile Phe Gly Thr Val
1               5                   10                  15

Phe Glu Ile Thr Asn Arg Tyr Asn Asp Leu Asn Pro Val Gly Met Gly
                20                  25                  30
```

```
Ala Phe Gly Leu Val Cys Ser Ala Thr Asp Thr Leu Thr Ser Gln Pro
             35                  40                  45

Val Ala Ile Lys Lys Ile Met Lys Pro Phe Ser Thr Ala Val Leu Ala
 50                  55                  60

Lys Arg Thr Tyr Arg Glu Leu Lys Leu Leu Lys His Leu Arg His Glu
 65                  70                  75                  80

Asn Leu Ile Cys Leu Gln Asp Ile Phe Leu Ser Pro Leu Glu Asp Ile
                 85                  90                  95

Tyr Phe Val Thr Glu Leu Gln Gly Thr Asp Leu His Arg Leu Leu Gln
            100                 105                 110

Thr Arg Pro Leu Glu Lys Gln Phe Val Gln Tyr Phe Leu Tyr Gln Ile
            115                 120                 125

Leu Arg Gly Leu Lys Tyr Val His Ser Ala Gly Val Ile His Arg Asp
130                 135                 140

Leu Lys Pro Ser Asn Ile Leu Ile Asn Glu Asn Cys Asp Leu Lys Ile
145                 150                 155                 160

Cys Asp Phe Gly Leu Ala Arg Ile Gln Asp Pro Gln Met Thr Gly Tyr
                165                 170                 175

Val Ser Thr Arg Tyr Tyr Arg Ala Pro Glu Ile Met Leu Thr Trp Gln
            180                 185                 190

Lys Tyr Asp Val Glu Val Asp Ile Trp Ser Ala Gly Cys Ile Phe Ala
            195                 200                 205

Glu Met Ile Glu Gly Lys Pro Leu Phe Pro Gly Lys Asp His Val His
            210                 215                 220

Gln Phe Ser Ile Ile Thr Asp Leu Leu Gly Ser Pro Pro Lys Asp Val
225                 230                 235                 240

Ile Asn Thr Ile Cys Ser Glu Asn Thr Leu Lys Phe Val Thr Ser Leu
                245                 250                 255

Pro His Arg Asp Pro Ile Pro Phe Ser Glu Arg Phe Lys Thr Val Glu
            260                 265                 270

Pro Asp Ala Val Asp Leu Leu Glu Lys Met Leu Val Phe Asp Pro Lys
            275                 280                 285

Lys Arg Ile Thr Ala Ala Asp Ala Leu Ala His Pro Tyr Ser Ala Pro
            290                 295                 300

Tyr His Asp Pro Thr Asp Glu Pro Val Ala Asp Ala Lys Phe Asp Trp
305                 310                 315                 320

His Phe Asn Asp Ala Asp Leu Pro Val Asp Thr Trp Arg Val Met Met
                325                 330                 335

Tyr Ser Glu Ile Leu Asp Phe His Lys Ile Gly Gly Ser Asp Gly Gln
            340                 345                 350

Ile Asp Ile Ser Ala Thr Phe Asp Asp Gln Val Ala Ala Ala Thr Ala
            355                 360                 365

Ala Ala Ala Gln Ala Gln Ala Gln Ala Gln Val Gln Leu Asn
            370                 375                 380

Met Ala Ala His Ser His Asn Gly Ala Gly Thr Thr Gly Asn Asp His
385                 390                 395                 400

Ser Asp Ile Ala Gly Gly Asn Lys Val Ser Asp His Val Ala Ala Asn
                405                 410                 415

Asp Thr Ile Thr Asp Tyr Gly Asn Gln Ala Ile Gln Tyr Ala Asn Glu
            420                 425                 430

Phe Gln Gln
        435
```

<210> SEQ ID NO 9
<211> LENGTH: 9279
<212> TYPE: DNA
<213> ORGANISM: Saccharomyces cerevisiae

<400> SEQUENCE: 9

| | | | | | |
|---|---|---|---|---|---|
| atgaatcaaa | gcgatccgca | agacaaaaaa | aatttcccaa | tggaatactc | tttgaccaag | 60 |
| catctttttt | ttgataggct | tctacttgtt | cttcccatag | aatctaattt | gaaaacatat | 120 |
| gctgatgtgg | aggcagattc | agttttcaat | tcgtgtcggt | ccatcatttt | gaatatagcc | 180 |
| atcactaagg | acttgaaccc | gattatcgaa | aacacattag | gtttaattga | cttgattgtg | 240 |
| caagatgaag | aaattacgtc | tgacaatatt | acagatgata | ttgcccattc | tatattggtt | 300 |
| cttttgagat | tactgagtga | tgttttgag | tattactggg | atcaaaacaa | tgacttcaag | 360 |
| aaaattagaa | acgataatta | caaaccggga | ttttcaagtc | acaggccaaa | cttccataca | 420 |
| tctaggccaa | agcacacgag | aatcaatcca | gctttggcga | cgatgttact | atgtaaaatt | 480 |
| tctaagctga | agttcaatac | aagaactta | aaggttttac | agaacatgtc | tcaccatctt | 540 |
| tctggcagcg | ctactatctc | aaaatcgagt | attttacccg | attcacagga | attttacaa | 600 |
| aagagaaact | atccagcata | taccgagaaa | atagatttaa | caatagatta | tatccagaga | 660 |
| ttcatatctg | cttccaatca | tgttgaattc | acaaagtgtg | tcaaaacaaa | agttgttgca | 720 |
| cctttattga | tatcacacac | ctcaaccgaa | ttgggcgtag | taaaccactt | ggatttattt | 780 |
| ggttgtgagt | atttgactga | taagaatctg | ctagcatatc | tggacatact | acaacacctg | 840 |
| tcaagttaca | tgaagaggac | catttttcat | tcgcttttgt | tatattatgc | ttccaaagct | 900 |
| tttttatttt | ggataatggc | aaggccaaaa | gaatacgtca | aaatttataa | caatctaata | 960 |
| tcatcagatt | ataatagtcc | gtcttcttca | tctgataatg | gtggttcgaa | taattctgat | 1020 |
| aaaacgtcta | tatcccaact | agtctcactg | ttattcgatg | acgtttattc | cacttttagt | 1080 |
| gtatcatcat | tattaacaaa | tgtcaataat | gaccaccact | accatcttca | tcattcatct | 1140 |
| tcttcatcaa | agacgaccaa | cactaatagt | ccaaactcta | tatcaaaaac | gtcgataaag | 1200 |
| cagtcgagtg | tgaatgcttc | tggcaatgtt | tctccgtctc | agttttctac | tgggaatgat | 1260 |
| gcatcgccta | cttcccctat | ggcatcattg | agttcaccct | taaacacgaa | catcctaggg | 1320 |
| tatccgttat | ctccaatcac | ttcaacacta | ggacaggcga | atacttccac | atcgactacg | 1380 |
| gctgcaacta | ccaaaacaga | tgcagatacg | ccctctacta | tgaatactaa | caacaataat | 1440 |
| aacaataaca | acagcgctaa | tcttaataat | attccacaac | gcatatttc | cttagatgac | 1500 |
| atttcatcct | ttaactcgag | tagaaaatca | ctcaatctag | atgatagtaa | ctccttgttt | 1560 |
| ctttgggata | cttctcagca | ttctaatgca | tcgatgacaa | atacaaatat | gcatgcagga | 1620 |
| gttaataatt | ctcagtctca | gaacgatcag | tcttctttaa | actatatgga | aaatattatg | 1680 |
| gagctgtatt | ccaactatac | cggatcagaa | ctatcctccc | atactgccat | attaaggttt | 1740 |
| ttggtggttc | tgaccttatt | agacagtgaa | gtatatgatg | agatgaactc | aaattcgtat | 1800 |
| agaaaaattt | cggaaccgat | aatgaatatt | atccgaaggg | actctaatac | ttcaagttgg | 1860 |
| ggctcagcat | ccaaaaaccc | aagtatcagg | cacctcaccc | atggcttaaa | aaaacttact | 1920 |
| ttacagcaag | gcaggaaacg | taacgttaaa | tttttgacat | atttgattag | aaatttgaat | 1980 |
| gggggacagt | tcgtttcaga | tgtttccttg | attgactcta | tcaggtccat | tctattctta | 2040 |
| atgacaatga | cgtcttctat | atcccaaatc | gattcaaata | ttgcttctgt | tatttttcg | 2100 |
| aagagattct | acaacttgtt | gggtcaaaat | ttagaggtcg | gcaccaattg | gaattctgcc | 2160 |

-continued

```
actgcaaata cttttatttc tcattgtgtt gaaaggaatc cccttacaca taggcgttta    2220
caattagagt tttttgcaag cggtttacag ctggattctg atttatttt aagacattta     2280
caactggaaa aagaactcaa tcacatagac cttcccaaaa tatcgttata cactgaagga    2340
tttagggtat tttttcacct agtaagcacc aaaaaacttc atgaggatat tgcagaaaaa    2400
acctcctctg tgttaaagag acttttctgc ataattgctg atattttgtt gaaagcaacg    2460
ccttattttg acgataatgt aaccaagatt attgcttcta tattggatgg catattttta    2520
gatcaatttg acgctgcgcg aacactttct aatgatgatc atgtcagttt tgatgctgcc    2580
acaagcgttt acactgagcc aaccgaaatt attcataact catcggatgc ctcgttagtc    2640
tcttcacttt cccaatcacc cttatcaatt aactcaggaa gcaatatcac caatacgcgc    2700
acctgggata ttcaatcaat cttaccaacc ttatcgaaca gatcaagtgc ttctgatttg    2760
agcttgtcta acattttgac taatccgttg gaggcacaac aaaataataa tgcaaacttg    2820
ttagcccata gattatctgg ggttcctact actaagagat acgcttcacc gaacgactct    2880
gaaagatcac gacaaagtcc atattcttct ccgccgcaat gcaacaaag tgacttgcct     2940
tctccgctct cagtcctctc gtcaagtgca ggattttctt ctaatcattc gattacggca    3000
accccaacta ttttgaaaaa catcaaatct ccaaaaccaa acaaaacaaa aaaaattgct    3060
gatgataaac aattgaaaca gccttcttat tcaagagtaa tactgagtga caatgatgaa    3120
gcaagaaaga ttatgatgaa cattttcagc attttcaaaa gaatgaccaa ctggtttata    3180
cgcccagatg ctaatacaga attcccgaag acttttacgg atattataaa accactttt    3240
gtctctatat tggattctaa tcaaagacta caagttacag cgcgggcttt tattgaaatc    3300
ccattaagtt atatagctac ttttgaagac attgataatg atcttgaccc aagagtactg    3360
aatgaccatt atttgttatg tacatatgcc gttactttgt ttgcttcatc attgtttgat    3420
ttgaagttag aaaatgcgaa gagagagatg ctactagaca ttattgttaa atttcaacga    3480
gtccgttctt atttatcaaa tttagcagaa aaacacaacc tagtccaggc aataattacg    3540
acggagaggt tgacgctgcc attattagtt ggtgctgtag aagtggaat tttcatttca     3600
ttatactgca gtcgtggaaa tacgccacgc ttaataaaaa tttcatgttg tgaatttcta    3660
cgatccttga gattttatca aaaatacgta ggcgctttgg atcaatattc catttacaat    3720
attgatttca tagatgctat ggcccaggac aatttcactg cctcaggatc agtggctttg    3780
caacggcgtc taagaaataa tattttaact tatatcaaag gatccgactc aatccttttg    3840
gattcaatgg acgtgattta caagaagtgg ttttacttca gctgttcgaa atcagttacg    3900
caagaggaac tagtagattt tagaagcttg gcaggcattc tagcttctat gtcaggtatt    3960
ctgtctgata tgcaagagtt ggaaaaaagc aagagcgctc cagataatga aggagacagc    4020
ttatcatttg agtcacgaaa tcccgcttat gaggtgcaca aaagtcttaa actcgagtta    4080
acgaaaaaaa tgaatttctt tatttcaaaa caatgtcaat ggttgaataa tccaaatcta    4140
ttaacaagag aaaattcgag agatatatta agtattgagt tgcatcctct atctttaac    4200
ttattgttta acaacctagg actgaaaata gatgaactga tgtcaattga tctttcaaag    4260
tcacatgagg attcatcgtt tgttttacta gagcagataa taattataat aagaactata    4320
ctaaagaggg atgatgatga aagataatg ctactctttt cgacggactt gcttgatgcg     4380
gtcgataagt tgatcgaaat agtggagaaa atttccatca agtcctccaa atattataag    4440
ggaattatcc aaatgtcgaa aatgtttaga gcatttgagc actctgaaaa gaacctgggc    4500
atttcaaatc atttccattt aaagaataaa tggttgaagt tagttattgg ttggttcaaa    4560
```

```
ctatctatta ataaggatta tgattttgaa aacctgtcaa gaccattaag ggaaatggat    4620
ttgcagaaaa gggacgaaga ttttttgtat atcgacactt ctattgaatc tgcaaaagca    4680
ttggcttacc taacacataa tgttccttta gaaataccgc cttcaagctc aaaagaagat    4740
tggaacagat cttctacagt atcatttggc aatcacttta ctattttgtt aaaaggtctg    4800
gagaaaagcg cggacctgaa tcagtttcca gtttcattaa ggcataagat cagtatactt    4860
aatgaaaatg taataatagc gctaacgaac ttatctaatg ccaatgtcaa cgtttcttta    4920
aaattcactt taccaatggg ttattctcca aataaagata tcagaatcgc cttttttaaga   4980 gttttcatcg acatagtaac caactatcca gttaaccctg agaaacatga aatggataaa    5040
atgctagcta tagacgactt cctgaaatat ataatcaaga acccaatatt agcattttc     5100 ggaagtttag cgtgttctcc tgctgatgtt gatttatatg ctggtggatt cttaaacgcc    5160
tttgacacta gaaatgcgtc tcatatcctt gttactgagc tccttaaaca agaaatcaaa    5220
cgggccgcaa gatcagacga tattctcaga gaaatagtt gtgcaacaag ggctttgtca    5280
ctttacacta gatctagagg taacaaatat ttgataaaaa ctttgagacc cgttttgcaa    5340
gggatagtgg ataacaagga gtcttttgaa attgataaga tgaaaccagg atccgaaaac    5400
tccgaaaaga tgttagactt attgagaag tacatgacaa gattaattga cgcaattaca    5460
agttctattg atgatttccc aatagaatta gttgatatct gtaaaacaat ttacaatgct    5520
gctagtgtaa attttccaga atacgcatat attgccgttg ggtcattcgt tttcttgagg    5580
tttatcgggc ctgctttagt tagtcctgat tcggaaaata tcattattgt tacgcacgcc    5640
catgacagaa agcccttat tacactagct aaagttattc aaagtttagc taatggcagg    5700
gaaaatatat tcaagaaaga tatcttagtt tcaaaagaag agttttttgaa aacctgtagt   5760 gataaaatat tcaattttt gtctgaattg tgcaagatac cgactaacaa tttcaccgtc    5820
aatgtaagag aagatccgac accaataagc tttgactact catttttgca taaattcttt    5880
tacctcaatg agtttaccat aagaaaagaa attattaatg aatccaaatt accaggggag    5940
ttcagctttt tgaaaaatac tgttatgctc aacgacaaaa ttcttggtgt attgggacaa    6000
cctagcatgg aaataaaaaa tgaaattcct ccttttgtag tcgagaatcg ggaaaaatat    6060
ccttcattgt atgaattcat gagtcgctat gccttcaaaa aagtggacat gaaagaagaa    6120
gaagaggata atgcgccatt tgtacatgaa gcaatgacat tggatggcat acaaatcatt    6180
gtcgtaactt ttaccaattg cgagtacaat aattttgtaa tggactcact ggtctataaa    6240
gttctgcaga tatatgcaag aatgtggtgc tctaaacatt atgtagttat cgattgtacc    6300
accttttatg ggggtaaggc taatttccaa aaattgacta ctctattttt cagtttgata    6360
ccagagcaag catcaagtaa ttgtatggga tgttattact tcaacgtcaa caaatcattt    6420
atggaccaat gggcctcatc atatactgta gaaaatccgt acttggtcac tacaattccc    6480
cgttgtttca tcaacagcaa tactgaccaa agtttgataa agtccttagg attgagtggt    6540
aggagtttgg aagttttgaa agatgtaaga gttactttgc atgatattac cctttatgac    6600
aaggaaaaaa agaagttttg tcccgtgtcc ttgaagatag gaaacaaata cttccaagtt    6660
ttacatgaga ttccgcagtt gtacaaggtt accgtatcaa acaggacatt cagcatcaaa    6720
ttcaacaatg tttacaagat atcaaattta atttcagtcg atgtctctaa caccacaggc    6780
gtttcctcgg aatttacgtt aagtcttgat aatgaagaaa agttggtatt ttgcagtccg    6840
aagtacctag aaattgtgaa aatgtttat tatgcccagt taaagatgga agaagacttt    6900
ggtacggatt tttcgaacga tatttcattt tcaacatcct cttcagcagt taatgcttct    6960
```

```
tactgcaatg ttaaagaagt tggtgaaatt atatcacatt tgtcattggt gatccttgta    7020
ggtttattca atgaggatga tctcgtcaaa aacatatcat acaaccttct cgtggcaacg    7080
caagaagcat ttaatttaga ttttgggaca aggcttcaca aatccccaga gacatatgta    7140
cccgatgata ccaccacgtt cttggcccta attttcaagg cttttcaga atcttcaacg     7200
gaactaactc catatatatg gaaatatatg ctggatggcc ttgaaaacga cgtgattcct    7260
caagaacata ttcctacggt tgtctgttca ttgtcatact gggtaccaaa cttatatgaa    7320
catgtatatt tggcaaatga cgaagaggga ccagaggcga tttcacgtat aatctatagc    7380
ttaatcaggt tgacggtcaa agagccaaat ttcacgacag cttaccttca acagatttgg    7440
tttttactgg cattggatgg tcgtctcacg aacgtgatag ttgaagaaat agtaagtcat    7500
gcgctggata gagattcaga aaacagagac tggatgaaag ctgtgtcaat actaaccagt    7560
tttccaacga cagagattgc ttgtcaggta atagagaagc taataaatat gatcaaatct    7620
tttctacctt ctctagcagt tgaggcttcc gcacacagtt ggtctgagct tactatttta    7680
tcaaaaatta gtgtgtcaat tttctttgaa tcacccttac tttcccagat gtatttaccg    7740
gagattcttt tcgctgtgtc tctgttaatt gatgtcggtc cttcggaaat aagagtctca    7800
ttgtacgagt tgttgatgaa tgtttgtcat tcttaacca acaatgagtc cttacctgaa     7860
aggaatagga aaaatttgga tatcgtctgt gcaacattcg cacgtcaaaa gttgaacttt    7920
atctccggtt ttagccaaga aaaaggtaga gttttaccaa attttgccgc ttcctccttc    7980
tccagtaaat tcggaacatt agatctcttc actaaaaaca ttatgctatt gatggaatat    8040
ggttctattt cagagggtgc acaatgggag gcaaaatata agaaatattt gatggatgcg    8100
attttggcc atcggtcgtt cttctctgcg agagctatga tgattctagg tataatgagt    8160
aagtcgcaca cgtccctttt cctttgtaaa gaacttttag ttgaaaccat gaaggtcttc    8220
gcagagccag ttgtggatga tgaacaaatg ttcatcatta tagctcatgt ctttacttac    8280
agcaaaattg tcgaagggtt agatccttct tcagaattaa tgaaagagct atttttggctt   8340
gctacaatat gtgttgaatc ccctcatcct ttactctttg aaggtggtct cctgttcatg    8400
gtaaattgtt tgaagcgact gtacacggtc catcttcaac ttggattcga tggcaaatcg    8460
ctagccaaaa aattaatgga atctagaaat tttgctgcta cgcttttggc taagttagag    8520
tcatacaatg gatgcatatg gaacgaagat aattttcctc atattatttt aggtttcatt    8580
gcaaacggtt tatccattcc tgtcgtaaaa ggagccgcat tagattgtct acaggccctt    8640
ttcaagaata catattacga aagaaagtcc aacccaaaat cctccgatta tctttgttac    8700
cttttcttac tccatttggt cttaagtcct gaacaacttt ctaccttgtt acttgaagtc    8760
ggcttcgaag atgaactggt acctttaaat aatacactaa aagtgccact tactttgatc    8820
aactggctaa gttcagactc agataaatct aatatagtct tataccaagg agcacttttg    8880
tttagctgtg ttatgtcaga cgaaccatgt aaattccgtt ttgctctatt gatgaggtat    8940
ttgctcaaag tcaaccctat ttgtgtattc aggttctata cgctgactag aaaggaattc    9000
aggaggttat caaccctaga acaatcatct gaagcggttg ctgtctcttt tgaattgatt    9060
gggatgcttg ttacacacag tgagtttaat tacctagagg aatttaatga tgaaatggtc    9120
gaacttttaa aaaagagagg cttgtcagtt gtgaagcctc tggatatttt tgatcaggaa    9180
catatagaaa agttaaaagg agagggtgaa catcaagtgg caatttatga gagaaaaaga    9240
ttagcaacaa tgatactggc aagaatgtcg tgctcctaa                           9279
```

```
<210> SEQ ID NO 10
<211> LENGTH: 3092
<212> TYPE: PRT
<213> ORGANISM: Saccharomyces cerevisiae

<400> SEQUENCE: 10

Met Asn Gln Ser Asp Pro Gln Asp Lys Lys Asn Phe Pro Met Glu Tyr
1               5                   10                  15

Ser Leu Thr Lys His Leu Phe Phe Asp Arg Leu Leu Leu Val Leu Pro
            20                  25                  30

Ile Glu Ser Asn Leu Lys Thr Tyr Ala Asp Val Glu Ala Asp Ser Val
        35                  40                  45

Phe Asn Ser Cys Arg Ser Ile Ile Leu Asn Ile Ala Ile Thr Lys Asp
50                  55                  60

Leu Asn Pro Ile Ile Glu Asn Thr Leu Gly Leu Ile Asp Leu Ile Val
65                  70                  75                  80

Gln Asp Glu Glu Ile Thr Ser Asp Asn Ile Thr Asp Ile Ala His
                    85                  90                  95

Ser Ile Leu Val Leu Leu Arg Leu Leu Ser Asp Val Phe Glu Tyr Tyr
            100                 105                 110

Trp Asp Gln Asn Asn Asp Phe Lys Lys Ile Arg Asn Asp Asn Tyr Lys
        115                 120                 125

Pro Gly Phe Ser Ser His Arg Pro Asn Phe His Thr Ser Arg Pro Lys
130                 135                 140

His Thr Arg Ile Asn Pro Ala Leu Ala Thr Met Leu Leu Cys Lys Ile
145                 150                 155                 160

Ser Lys Leu Lys Phe Asn Thr Arg Thr Leu Lys Val Leu Gln Asn Met
                    165                 170                 175

Ser His His Leu Ser Gly Ser Ala Thr Ile Ser Lys Ser Ser Ile Leu
            180                 185                 190

Pro Asp Ser Gln Glu Phe Leu Gln Lys Arg Asn Tyr Pro Ala Tyr Thr
        195                 200                 205

Glu Lys Ile Asp Leu Thr Ile Asp Tyr Ile Gln Arg Phe Ile Ser Ala
210                 215                 220

Ser Asn His Val Glu Phe Thr Lys Cys Val Lys Thr Lys Val Val Ala
225                 230                 235                 240

Pro Leu Leu Ile Ser His Thr Ser Thr Glu Leu Gly Val Val Asn His
                    245                 250                 255

Leu Asp Leu Phe Gly Cys Glu Tyr Leu Thr Asp Lys Asn Leu Leu Ala
            260                 265                 270

Tyr Leu Asp Ile Leu Gln His Leu Ser Ser Tyr Met Lys Arg Thr Ile
        275                 280                 285

Phe His Ser Leu Leu Leu Tyr Tyr Ala Ser Lys Ala Phe Leu Phe Trp
290                 295                 300

Ile Met Ala Arg Pro Lys Glu Tyr Val Lys Ile Tyr Asn Asn Leu Ile
305                 310                 315                 320

Ser Ser Asp Tyr Asn Ser Pro Ser Ser Ser Asp Asn Gly Gly Ser
                    325                 330                 335

Asn Asn Ser Asp Lys Thr Ser Ile Ser Gln Leu Val Ser Leu Leu Phe
            340                 345                 350

Asp Asp Val Tyr Ser Thr Phe Ser Val Ser Leu Leu Thr Asn Val
        355                 360                 365

Asn Asn Asp His His Tyr His Leu His His Ser Ser Ser Ser Ser Lys
370                 375                 380
```

```
Thr Thr Asn Thr Asn Ser Pro Asn Ser Ile Ser Lys Thr Ser Ile Lys
385                 390                 395                 400

Gln Ser Ser Val Asn Ala Ser Gly Asn Val Ser Pro Ser Gln Phe Ser
            405                 410                 415

Thr Gly Asn Asp Ala Ser Pro Thr Ser Pro Met Ala Ser Leu Ser Ser
            420                 425                 430

Pro Leu Asn Thr Asn Ile Leu Gly Tyr Pro Leu Ser Pro Ile Thr Ser
            435                 440                 445

Thr Leu Gly Gln Ala Asn Thr Ser Thr Ser Thr Thr Ala Ala Thr Thr
    450                 455                 460

Lys Thr Asp Ala Asp Thr Pro Ser Thr Met Asn Thr Asn Asn Asn Asn
465                 470                 475                 480

Asn Asn Asn Asn Ser Ala Asn Leu Asn Asn Ile Pro Gln Arg Ile Phe
            485                 490                 495

Ser Leu Asp Asp Ile Ser Ser Phe Asn Ser Ser Arg Lys Ser Leu Asn
            500                 505                 510

Leu Asp Asp Ser Asn Ser Leu Phe Leu Trp Asp Thr Ser Gln His Ser
    515                 520                 525

Asn Ala Ser Met Thr Asn Thr Asn Met His Ala Gly Val Asn Asn Ser
530                 535                 540

Gln Ser Gln Asn Asp Gln Ser Ser Leu Asn Tyr Met Glu Asn Ile Met
545                 550                 555                 560

Glu Leu Tyr Ser Asn Tyr Thr Gly Ser Glu Leu Ser Ser His Thr Ala
            565                 570                 575

Ile Leu Arg Phe Leu Val Val Leu Thr Leu Leu Asp Ser Glu Val Tyr
            580                 585                 590

Asp Glu Met Asn Ser Asn Ser Tyr Arg Lys Ile Ser Glu Pro Ile Met
        595                 600                 605

Asn Ile Asn Pro Lys Asp Ser Asn Thr Ser Ser Trp Gly Ser Ala Ser
    610                 615                 620

Lys Asn Pro Ser Ile Arg His Leu Thr His Gly Leu Lys Lys Leu Thr
625                 630                 635                 640

Leu Gln Gln Gly Arg Lys Arg Asn Val Lys Phe Leu Thr Tyr Leu Ile
            645                 650                 655

Arg Asn Leu Asn Gly Gly Gln Phe Val Ser Asp Val Ser Leu Ile Asp
            660                 665                 670

Ser Ile Arg Ser Ile Leu Phe Leu Met Thr Met Thr Ser Ser Ile Ser
            675                 680                 685

Gln Ile Asp Ser Asn Ile Ala Ser Val Ile Phe Ser Lys Arg Phe Tyr
    690                 695                 700

Asn Leu Leu Gly Gln Asn Leu Glu Val Gly Thr Asn Trp Asn Ser Ala
705                 710                 715                 720

Thr Ala Asn Thr Phe Ile Ser His Cys Val Glu Arg Asn Pro Leu Thr
            725                 730                 735

His Arg Arg Leu Gln Leu Glu Phe Phe Ala Ser Gly Leu Gln Leu Asp
            740                 745                 750

Ser Asp Leu Phe Leu Arg His Leu Gln Leu Glu Lys Glu Leu Asn His
    755                 760                 765

Ile Asp Leu Pro Lys Ile Ser Leu Tyr Thr Glu Gly Phe Arg Val Phe
    770                 775                 780

Phe His Leu Val Ser Thr Lys Lys Leu His Glu Asp Ile Ala Glu Lys
785                 790                 795                 800
```

```
Thr Ser Ser Val Leu Lys Arg Leu Phe Cys Ile Ile Ala Asp Ile Leu
                805                 810                 815

Leu Lys Ala Thr Pro Tyr Phe Asp Asp Asn Val Thr Lys Ile Ile Ala
            820                 825                 830

Ser Ile Leu Asp Gly His Ile Leu Asp Gln Phe Asp Ala Ala Arg Thr
            835                 840                 845

Leu Ser Asn Asp Asp His Val Ser Phe Asp Ala Ala Thr Ser Val Tyr
850                 855                 860

Thr Glu Pro Thr Glu Ile Ile His Asn Ser Ser Asp Ala Ser Leu Val
865                 870                 875                 880

Ser Ser Leu Ser Gln Ser Pro Leu Ser Ile Asn Ser Gly Ser Asn Ile
            885                 890                 895

Thr Asn Thr Arg Thr Trp Asp Ile Gln Ser Ile Leu Pro Thr Leu Ser
            900                 905                 910

Asn Arg Ser Ser Ala Ser Asp Leu Ser Leu Ser Asn Ile Leu Thr Asn
            915                 920                 925

Pro Leu Glu Ala Gln Gln Asn Asn Asn Ala Asn Leu Leu Ala His Arg
            930                 935                 940

Leu Ser Gly Val Pro Thr Thr Lys Arg Tyr Ala Ser Pro Asn Asp Ser
945                 950                 955                 960

Glu Arg Ser Arg Gln Ser Pro Tyr Ser Pro Pro Gln Leu Gln Gln
                965                 970                 975

Ser Asp Leu Pro Ser Pro Leu Ser Val Leu Ser Ser Ala Gly Phe
            980                 985                 990

Ser Ser Asn His Ser Ile Thr Ala Thr Pro Thr Ile Leu Lys Asn Ile
            995                 1000                1005

Lys Ser Pro Lys Pro Asn Lys Thr Lys Lys Ile Ala Asp Asp Lys
    1010            1015                1020

Gln Leu Lys Gln Pro Ser Tyr Ser Arg Val Ile Leu Ser Asp Asn
    1025            1030                1035

Asp Glu Ala Arg Lys Ile Met Met Asn Ile Phe Ser Ile Phe Lys
    1040            1045                1050

Arg Met Thr Asn Trp Phe Ile Arg Pro Asp Ala Asn Thr Glu Phe
    1055            1060                1065

Pro Lys Thr Phe Thr Asp Ile Ile Lys Pro Leu Phe Val Ser Ile
    1070            1075                1080

Leu Asp Ser Asn Gln Arg Leu Gln Val Thr Ala Arg Ala Phe Ile
    1085            1090                1095

Glu Ile Pro Leu Ser Tyr Ile Ala Thr Phe Glu Asp Ile Asp Asn
    1100            1105                1110

Asp Leu Asp Pro Arg Val Leu Asn Asp His Tyr Leu Leu Cys Thr
    1115            1120                1125

Tyr Ala Val Thr Leu Phe Ala Ser Ser Leu Phe Asp Leu Lys Leu
    1130            1135                1140

Glu Asn Ala Lys Arg Glu Met Leu Leu Asp Ile Ile Val Lys Phe
    1145            1150                1155

Gln Arg Val Arg Ser Tyr Leu Ser Asn Leu Ala Glu Lys His Asn
    1160            1165                1170

Leu Val Gln Ala Ile Ile Thr Thr Glu Arg Leu Thr Leu Pro Leu
    1175            1180                1185

Leu Val Gly Ala Val Gly Ser Gly Ile Phe Ile Ser Leu Tyr Cys
    1190            1195                1200
```

```
Ser Arg Gly Asn Thr Pro Arg Leu Ile Lys Ile Ser Cys Cys Glu
1205                1210                1215

Phe Leu Arg Ser Leu Arg Phe Tyr Gln Lys Tyr Val Gly Ala Leu
1220                1225                1230

Asp Gln Tyr Ser Ile Tyr Asn Ile Asp Phe Ile Asp Ala Met Ala
1235                1240                1245

Gln Asp Asn Phe Thr Ala Ser Gly Ser Val Ala Leu Gln Arg Arg
1250                1255                1260

Leu Arg Asn Asn Ile Leu Thr Tyr Ile Lys Gly Ser Asp Ser Ile
1265                1270                1275

Leu Leu Asp Ser Met Asp Val Ile Tyr Lys Lys Trp Phe Tyr Phe
1280                1285                1290

Ser Cys Ser Lys Ser Val Thr Gln Glu Glu Leu Val Asp Phe Arg
1295                1300                1305

Ser Leu Ala Gly Ile Leu Ala Ser Met Ser Gly Ile Leu Ser Asp
1310                1315                1320

Met Gln Glu Leu Glu Lys Ser Lys Ser Ala Pro Asp Asn Glu Gly
1325                1330                1335

Asp Ser Leu Ser Phe Glu Ser Arg Asn Pro Ala Tyr Glu Val His
1340                1345                1350

Lys Ser Leu Lys Leu Glu Leu Thr Lys Lys Met Asn Phe Phe Ile
1355                1360                1365

Ser Lys Gln Cys Gln Trp Leu Asn Asn Pro Asn Leu Leu Thr Arg
1370                1375                1380

Glu Asn Ser Arg Asp Ile Leu Ser Ile Glu Leu His Pro Leu Ser
1385                1390                1395

Phe Asn Leu Leu Phe Asn Asn Leu Gly Leu Lys Ile Asp Glu Leu
1400                1405                1410

Met Ser Ile Asp Leu Ser Lys Ser His Glu Asp Ser Ser Phe Val
1415                1420                1425

Leu Leu Glu Gln Ile Ile Ile Ile Arg Thr Ile Leu Lys Arg
1430                1435                1440

Asp Asp Asp Glu Lys Ile Met Leu Leu Phe Ser Thr Asp Leu Leu
1445                1450                1455

Asp Ala Val Asp Lys Leu Ile Glu Ile Val Glu Lys Ile Ser Ile
1460                1465                1470

Lys Ser Ser Lys Tyr Tyr Lys Gly Ile Ile Gln Met Ser Lys Met
1475                1480                1485

Phe Arg Ala Phe Glu His Ser Glu Lys Asn Leu Gly Ile Ser Asn
1490                1495                1500

His Phe His Leu Lys Asn Lys Trp Leu Lys Leu Val Ile Gly Trp
1505                1510                1515

Phe Lys Leu Ser Ile Asn Lys Asp Tyr Asp Phe Glu Asn Leu Ser
1520                1525                1530

Arg Pro Leu Arg Glu Met Asp Leu Gln Lys Arg Asp Glu Asp Phe
1535                1540                1545

Leu Tyr Ile Asp Thr Ser Ile Glu Ser Ala Lys Ala Leu Ala Tyr
1550                1555                1560

Leu Thr His Asn Val Pro Leu Glu Ile Pro Pro Ser Ser Ser Lys
1565                1570                1575

Glu Asp Trp Asn Arg Ser Ser Thr Val Ser Phe Gly Asn His Phe
1580                1585                1590
```

-continued

Thr Ile Leu Leu Lys Gly Leu Glu Lys Ser Ala Asp Leu Asn Gln
1595                1600                1605

Phe Pro Val Ser Leu Arg His Lys Ile Ser Ile Leu Asn Glu Asn
1610                1615                1620

Val Ile Ile Ala Leu Thr Asn Leu Ser Asn Ala Asn Val Asn Val
1625                1630                1635

Ser Leu Lys Phe Thr Leu Pro Met Gly Tyr Ser Pro Asn Lys Asp
1640                1645                1650

Ile Arg Ile Ala Phe Leu Arg Val Phe Ile Asp Ile Val Thr Asn
1655                1660                1665

Tyr Pro Val Asn Pro Glu Lys His Glu Met Asp Lys Met Leu Ala
1670                1675                1680

Ile Asp Asp Phe Leu Lys Tyr Ile Ile Lys Asn Pro Ile Leu Ala
1685                1690                1695

Phe Phe Gly Ser Leu Ala Cys Ser Pro Ala Asp Val Asp Leu Tyr
1700                1705                1710

Ala Gly Gly Phe Leu Asn Ala Phe Asp Thr Arg Asn Ala Ser His
1715                1720                1725

Ile Leu Val Thr Glu Leu Leu Lys Gln Glu Ile Lys Arg Ala Ala
1730                1735                1740

Arg Ser Asp Asp Ile Leu Arg Arg Asn Ser Cys Ala Thr Arg Ala
1745                1750                1755

Leu Ser Leu Tyr Thr Arg Ser Arg Gly Asn Lys Tyr Leu Ile Lys
1760                1765                1770

Thr Leu Arg Pro Val Leu Gln Gly Ile Val Asp Asn Lys Glu Ser
1775                1780                1785

Phe Glu Ile Asp Lys Met Lys Pro Gly Ser Glu Asn Ser Glu Lys
1790                1795                1800

Met Leu Asp Leu Phe Glu Lys Tyr Met Thr Arg Leu Ile Asp Ala
1805                1810                1815

Ile Thr Ser Ser Ile Asp Asp Phe Pro Ile Glu Leu Val Asp Ile
1820                1825                1830

Cys Lys Thr Ile Tyr Asn Ala Ala Ser Val Asn Phe Pro Glu Tyr
1835                1840                1845

Ala Tyr Ile Ala Val Gly Ser Phe Val Phe Leu Arg Phe Ile Gly
1850                1855                1860

Pro Ala Leu Val Ser Pro Asp Ser Glu Asn Ile Ile Ile Val Thr
1865                1870                1875

His Ala His Asp Arg Lys Pro Phe Ile Thr Leu Ala Lys Val Ile
1880                1885                1890

Gln Ser Leu Ala Asn Gly Arg Glu Asn Ile Phe Lys Lys Asp Ile
1895                1900                1905

Leu Val Ser Lys Glu Glu Phe Leu Lys Thr Cys Ser Asp Lys Ile
1910                1915                1920

Phe Asn Phe Leu Ser Glu Leu Cys Lys Ile Pro Thr Asn Asn Phe
1925                1930                1935

Thr Val Asn Val Arg Glu Asp Pro Thr Pro Ile Ser Phe Asp Tyr
1940                1945                1950

Ser Phe Leu His Lys Phe Phe Tyr Leu Asn Glu Phe Thr Ile Arg
1955                1960                1965

Lys Glu Ile Ile Asn Glu Ser Lys Leu Pro Gly Glu Phe Ser Phe
1970                1975                1980

```
Leu Lys Asn Thr Val Met Leu Asn Asp Lys Ile Leu Gly Val Leu
1985                    1990                1995

Gly Gln Pro Ser Met Glu Ile Lys Asn Glu Ile Pro Pro Phe Val
2000                    2005                2010

Val Glu Asn Arg Glu Lys Tyr Pro Ser Leu Tyr Glu Phe Met Ser
2015                    2020                2025

Arg Tyr Ala Phe Lys Lys Val Asp Met Lys Glu Glu Glu Glu Asp
2030                    2035                2040

Asn Ala Pro Phe Val His Glu Ala Met Thr Leu Asp Gly Ile Gln
2045                    2050                2055

Ile Ile Val Val Thr Phe Thr Asn Cys Glu Tyr Asn Asn Phe Val
2060                    2065                2070

Met Asp Ser Leu Val Tyr Lys Val Leu Gln Ile Tyr Ala Arg Met
2075                    2080                2085

Trp Cys Ser Lys His Tyr Val Val Ile Asp Cys Thr Thr Phe Tyr
2090                    2095                2100

Gly Gly Lys Ala Asn Phe Gln Lys Leu Thr Thr Leu Phe Phe Ser
2105                    2110                2115

Leu Ile Pro Glu Gln Ala Ser Ser Asn Cys Met Gly Cys Tyr Tyr
2120                    2125                2130

Phe Asn Val Asn Lys Ser Phe Met Asp Gln Trp Ala Ser Ser Tyr
2135                    2140                2145

Thr Val Glu Asn Pro Tyr Leu Val Thr Thr Ile Pro Arg Cys Phe
2150                    2155                2160

Ile Asn Ser Asn Thr Asp Gln Ser Leu Ile Lys Ser Leu Gly Leu
2165                    2170                2175

Ser Gly Arg Ser Leu Glu Val Leu Lys Asp Val Arg Val Thr Leu
2180                    2185                2190

His Asp Ile Thr Leu Tyr Asp Lys Glu Lys Lys Phe Cys Pro
2195                    2200                2205

Val Ser Leu Lys Ile Gly Asn Lys Tyr Phe Gln Val Leu His Glu
2210                    2215                2220

Ile Pro Gln Leu Tyr Lys Val Thr Val Ser Asn Arg Thr Phe Ser
2225                    2230                2235

Ile Lys Phe Asn Asn Val Tyr Lys Ile Ser Asn Leu Ile Ser Val
2240                    2245                2250

Asp Val Ser Asn Thr Thr Gly Val Ser Ser Glu Phe Thr Leu Ser
2255                    2260                2265

Leu Asp Asn Glu Glu Lys Leu Val Phe Cys Ser Pro Lys Tyr Leu
2270                    2275                2280

Glu Ile Val Lys Met Phe Tyr Tyr Ala Gln Leu Lys Met Glu Glu
2285                    2290                2295

Asp Phe Gly Thr Asp Phe Ser Asn Asp Ile Ser Phe Ser Thr Ser
2300                    2305                2310

Ser Ser Ala Val Asn Ala Ser Tyr Cys Asn Val Lys Glu Val Gly
2315                    2320                2325

Glu Ile Ile Ser His Leu Ser Leu Val Ile Leu Val Gly Leu Phe
2330                    2335                2340

Asn Glu Asp Asp Leu Val Lys Asn Ile Ser Tyr Asn Leu Leu Val
2345                    2350                2355

Ala Thr Gln Glu Ala Phe Asn Leu Asp Phe Gly Thr Arg Leu His
2360                    2365                2370
```

-continued

Lys Ser Pro Glu Thr Tyr Val Pro Asp Asp Thr Thr Thr Phe Leu
2375            2380                2385

Ala Leu Ile Phe Lys Ala Phe Ser Glu Ser Ser Thr Glu Leu Thr
2390            2395                2400

Pro Tyr Ile Trp Lys Tyr Met Leu Asp Gly Leu Glu Asn Asp Val
2405            2410                2415

Ile Pro Gln Glu His Ile Pro Thr Val Val Cys Ser Leu Ser Tyr
2420            2425                2430

Trp Val Pro Asn Leu Tyr Glu His Val Tyr Leu Ala Asn Asp Glu
2435            2440                2445

Glu Gly Pro Glu Ala Ile Ser Arg Ile Ile Tyr Ser Leu Ile Arg
2450            2455                2460

Leu Thr Val Lys Glu Pro Asn Phe Thr Thr Ala Tyr Leu Gln Gln
2465            2470                2475

Ile Trp Phe Leu Leu Ala Leu Asp Gly Arg Leu Thr Asn Val Ile
2480            2485                2490

Val Glu Glu Ile Val Ser His Ala Leu Asp Arg Asp Ser Glu Asn
2495            2500                2505

Arg Asp Trp Met Lys Ala Val Ser Ile Leu Thr Ser Phe Pro Thr
2510            2515                2520

Thr Glu Ile Ala Cys Gln Val Ile Glu Lys Leu Ile Asn Met Ile
2525            2530                2535

Lys Ser Phe Leu Pro Ser Leu Ala Val Glu Ala Ser Ala His Ser
2540            2545                2550

Trp Ser Glu Leu Thr Ile Leu Ser Lys Ile Ser Val Ser Ile Phe
2555            2560                2565

Phe Glu Ser Pro Leu Leu Ser Gln Met Tyr Leu Pro Glu Ile Leu
2570            2575                2580

Phe Ala Val Ser Leu Leu Ile Asp Val Gly Pro Ser Glu Ile Arg
2585            2590                2595

Val Ser Leu Tyr Glu Leu Leu Met Asn Val Cys His Ser Leu Thr
2600            2605                2610

Asn Asn Glu Ser Leu Pro Glu Arg Asn Arg Lys Asn Leu Asp Ile
2615            2620                2625

Val Cys Ala Thr Phe Ala Arg Gln Lys Leu Asn Phe Ile Ser Gly
2630            2635                2640

Phe Ser Gln Glu Lys Gly Arg Val Leu Pro Asn Phe Ala Ala Ser
2645            2650                2655

Ser Phe Ser Ser Lys Phe Gly Thr Leu Asp Leu Phe Thr Lys Asn
2660            2665                2670

Ile Met Leu Leu Met Glu Tyr Gly Ser Ile Ser Glu Gly Ala Gln
2675            2680                2685

Trp Glu Ala Lys Tyr Lys Lys Tyr Leu Met Asp Ala Ile Phe Gly
2690            2695                2700

His Arg Ser Phe Phe Ser Ala Arg Ala Met Met Ile Leu Gly Ile
2705            2710                2715

Met Ser Lys Ser His Thr Ser Leu Phe Leu Cys Lys Glu Leu Leu
2720            2725                2730

Val Glu Thr Met Lys Val Phe Ala Glu Pro Val Val Asp Asp Glu
2735            2740                2745

Gln Met Phe Ile Ile Ile Ala His Val Phe Thr Tyr Ser Lys Ile
2750            2755                2760

```
Val Glu Gly Leu Asp Pro Ser Ser Glu Leu Met Lys Glu Leu Phe
    2765            2770            2775
Trp Leu Ala Thr Ile Cys Val Glu Ser Pro His Pro Leu Leu Phe
    2780            2785            2790
Glu Gly Gly Leu Leu Phe Met Val Asn Cys Leu Lys Arg Leu Tyr
    2795            2800            2805
Thr Val His Leu Gln Leu Gly Phe Asp Gly Lys Ser Leu Ala Lys
    2810            2815            2820
Lys Leu Met Glu Ser Arg Asn Phe Ala Ala Thr Leu Leu Ala Lys
    2825            2830            2835
Leu Glu Ser Tyr Asn Gly Cys Ile Trp Asn Glu Asp Asn Phe Pro
    2840            2845            2850
His Ile Ile Leu Gly Phe Ile Ala Asn Gly Leu Ser Ile Pro Val
    2855            2860            2865
Val Lys Gly Ala Ala Leu Asp Cys Leu Gln Ala Leu Phe Lys Asn
    2870            2875            2880
Thr Tyr Tyr Glu Arg Lys Ser Asn Pro Lys Ser Ser Asp Tyr Leu
    2885            2890            2895
Cys Tyr Leu Phe Leu Leu His Leu Val Leu Ser Pro Glu Gln Leu
    2900            2905            2910
Ser Thr Leu Leu Leu Glu Val Gly Phe Glu Asp Glu Leu Val Pro
    2915            2920            2925
Leu Asn Asn Thr Leu Lys Val Pro Leu Thr Leu Ile Asn Trp Leu
    2930            2935            2940
Ser Ser Asp Ser Asp Lys Ser Asn Ile Val Leu Tyr Gln Gly Ala
    2945            2950            2955
Leu Leu Phe Ser Cys Val Met Ser Asp Glu Pro Cys Lys Phe Arg
    2960            2965            2970
Phe Ala Leu Leu Met Arg Tyr Leu Leu Lys Val Asn Pro Ile Cys
    2975            2980            2985
Val Phe Arg Phe Tyr Thr Leu Thr Arg Lys Glu Phe Arg Arg Leu
    2990            2995            3000
Ser Thr Leu Glu Gln Ser Ser Glu Ala Val Ala Val Ser Phe Glu
    3005            3010            3015
Leu Ile Gly Met Leu Val Thr His Ser Glu Phe Asn Tyr Leu Glu
    3020            3025            3030
Glu Phe Asn Asp Glu Met Val Glu Leu Leu Lys Lys Arg Gly Leu
    3035            3040            3045
Ser Val Val Lys Pro Leu Asp Ile Phe Asp Gln Glu His Ile Glu
    3050            3055            3060
Lys Leu Lys Gly Glu Gly Glu His Gln Val Ala Ile Tyr Glu Arg
    3065            3070            3075
Lys Arg Leu Ala Thr Met Ile Leu Ala Arg Met Ser Cys Ser
    3080            3085            3090
```